United States Patent [19]

Enomoto et al.

[11] Patent Number: 5,266,556
[45] Date of Patent: Nov. 30, 1993

[54] ARYLINDAZOLE DERIVATIVES AND THEIR USE

[75] Inventors: Masayuki Enomoto, Nishinomiya; Susumu Takemura, Takarazuka; Masaharu Sakaki, Toyonaka; Satoru Kizawa, Takarazuka, all of Japan; Eiki Nagano, Raleigh, N.C.

[73] Assignee: Sumitomo Chemical Company, Limited, Osaka, Japan

[21] Appl. No.: 980,215

[22] Filed: Nov. 23, 1992

[30] Foreign Application Priority Data

Nov. 25, 1991 [JP] Japan ................................. 3-309041

[51] Int. Cl.$^5$ ..................... A01N 43/38; C07D 237/26
[52] U.S. Cl. ..................................... 504/281; 504/253; 504/261; 548/361.1; 548/257; 546/271
[58] Field of Search ..................... 548/361.1; 504/281

[56] References Cited

U.S. PATENT DOCUMENTS

| | | | |
|---|---|---|---|
| 3,625,970 | 12/1971 | Ambrus | 548/361.5 |
| 4,124,374 | 11/1978 | Wolf | 548/369 |
| 5,006,148 | 4/1991 | Fischer et al. | 548/375 |
| 5,115,337 | 5/1992 | Okazaki et al. | 548/361.1 |

FOREIGN PATENT DOCUMENTS

| | | |
|---|---|---|
| 0105721 | 9/1983 | European Pat. Off. . |
| 0287851 | 3/1988 | European Pat. Off. . |
| 0370332 | 11/1989 | European Pat. Off. . |
| 347382 | 12/1989 | European Pat. Off. . |
| 3338903 | 5/1985 | Fed. Rep. of Germany . |

OTHER PUBLICATIONS

Pervozvanskaya et al., CA 88:104506c, 1978.
Portal et al., CA 75:35872m, 1971.
Tsuge et al., CA 78:97612x, 1973.
V. P. Arya et al., Indian Journal of Chemistry, vol. 15B, Jul. 1977; pp. 625-628.

Primary Examiner—Jane T. Fan
Attorney, Agent, or Firm—Birch, Stewart, Kolasch & Birch

[57] ABSTRACT

There are disclosed novel arylindazole derivatives of the formula:

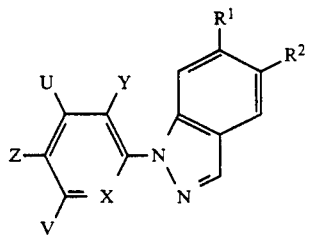

and agrochemically acceptable salts thereof. Also disclosed are a herbicidal composition including the above arylindazole derivative as an active ingredient and a method for exterminating undesired weeds by the application of a herbicidally effective amount of the above arylindazole derivative to an area where the undesired weeds grow or will grow.

36 Claims, No Drawings

ARYLINDAZOLE DERIVATIVES AND THEIR USE

FIELD OF THE INVENTION

The present invention relates to novel arylindazole derivatives and their use, particularly as a

BACKGROUND OF THE INVENTION

Certain kinds of arylindazole derivatives have hitherto been known in the art, for example, from U.S. Pat. No. 3,625,970 and Indian. J. Chem., 15, 625 (1977). These publications make no mention that the arylindazole derivatives disclosed therein have a herbicidal activity.

SUMMARY OF THE INVENTION

The present inventors have intensively studied various compounds and found that particular arylindazole derivatives have an excellent herbicidal activity, thereby completing the present invention.

According to the present invention, there are provided arylindazole derivatives of the formula:

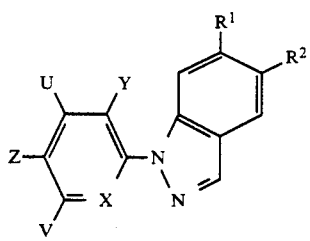

wherein X is nitrogen, CH, CCl or CF; Y is hydrogen or halogen; Z is $C_1$-$C_2$ perfluoroalkyl; U and V are the same or different and each is hydrogen, halogen or $C_1$-$C_2$ alkyl optionally substituted with halogen; $R^1$ is hydrogen, halogen, nitro, cyano, $C_1$-$C_5$ hydroxyalkyl, —$QB^1$ [wherein Q is oxygen or sulfur, and $B^1$ is hydrogen, $C_1$-$C_5$ alkyl, $C_2$-$C_4$ alkenyl, $C_3$-$C_5$ alkynyl, $C_3$-$C_6$ cycloalkyl, cyanomethyl, $C_1$-$C_4$ haloalkyl, $C_1$-$C_4$ alkylcarbonyl, $C_1$-$C_4$ alkoxycarbonyl, $C_1$-$C_4$ hydroxyalkyl, $C_1$-$C_3$ alkoxy($C_1$-$C_2$)- alkyl or —$CHB^{21}CO_2B^{22}$ (wherein $B^{21}$ is hydrogen, halogen, $C_1$-$C_3$ alkyl or methoxy, and $B^{22}$ is hydrogen, $C_1$-$C_5$ alkyl, $C_2$-$C_4$ alkenyl, $C_3$-$C_5$ alkynyl, $C_3$-$C_6$ cycloalkyl, $C_1$-$C_3$ haloalkyl or $C_1$-$C_3$ alkoxy($C_1$-$C_2$)alkyl)], —$CO_2B^{22}$ [wherein $B^{22}$ is as defined above], —$ND^1D^2$ [wherein $D^1$ and $D^2$ are the same or different and each is hydrogen, $C_1$-$C_5$ alkyl, $C_2$-$C_4$ alkenyl, $C_3$-$C_5$ alkynyl, $C_3$-$C_6$ cycloalkyl, cyanomethyl, $C_1$-$C_4$ haloalkyl, $C_1$-$C_4$ hydroxyalkyl, $C_1$-$C_3$ alkoxy($C_1$-$C_2$)alkyl, —$(CH_2)_nCHB^{21}CO_2B^{22}$ (wherein n is an integer of 0, 1 or 2, and $B^{21}$ and $B^{22}$ are each as defined above) or —$SO_2B^{23}$ (wherein $B^{23}$ is $C_1$-$C_5$ alkyl optionally substituted with halogen) or —$COD^{21}$ [wherein $D^{21}$ is hydrogen, $C_1$-$C_4$ alkyl or $C_1$-$C_3$ alkoxy($C_1$-$C_2$)alkyl]; and $R^2$ is hydrogen, halogen, nitro, cyano or amino; or $R^1$ and $R^2$ are taken together to form —N=N—$NB^1$— [wherein $B^1$ is as defined above]; and agrochemically acceptable salts thereof.

The present invention also provides a herbicidal composition comprising the compound (1) as an active ingredient and a method for exterminating undesired weeds, which comprises applying a herbicidally effective amount of the compound (1) to an area where the undesired weeds grow or will grow.

Among the compounds (1), preferred are those wherein $R^1$ is —$OB^1$. Among the compounds (1) wherein $R^1$ is —$OB^1$, more preferred are those wherein $B^1$ is $C_1$-$C_5$ alkyl, $C_2$-$C_4$ alkenyl, $C_3$-$C_5$ alkynyl or $CHB^{21}CO_2B^{22}$. Among the above compounds wherein $B^1$ is $CHB^{21}CO_2B^{22}$, particularly preferred are those wherein $B^{21}$ is methyl, and further more preferred are those wherein $B^{22}$ is $C_1$-$C_5$ alkyl. Among the above more preferred compounds wherein $B^1$ is $C_1$-$C_5$ alkyl, $C_2$-$C_4$ alkenyl, $C_3$-$C_5$ alkynyl, particularly preferred are those wherein $R^2$ is nitro. Among the compounds (1) wherein $R^1$ is $OB^1$, more preferred are those wherein $R^2$ is hydrogen or nitro. Among the compounds (1) wherein $R^1$ is $OCH(CH_3)CO_2B^{22}$, particularly preferred are those wherein $R^2$ is hydrogen. Among the compounds (1) wherein $R^1$ is $OB^1$, more preferred are those wherein X is nitrogen, CCl or CF, Y is chlorine or fluorine, Z is trifluoromethyl, and U and V are hydrogen.

The compound (1) of the present invention may be converted into a salt, particularly into an agrochemically acceptable salt, such as sodium salt, potassium salt and ammonium salt, when $B^{22}$ is hydrogen. To obtain a desirable salt of the compound (1), the compound (1) wherein $B^{22}$ is hydrogen may be allowed to react with the corresponding hydroxide.

DETAILED DESCRIPTION OF THE INVENTION

The compound (I) can be produced by reacting a compound of the formula

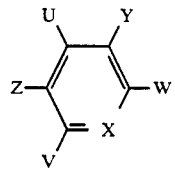

wherein W is halogen, and X, Y, Z, U and V are each as defined above with a compound of the formula:

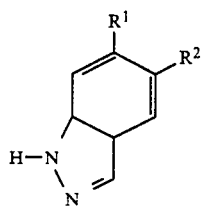

wherein $R^1$ and $R^2$ are each as defined above. The reaction is usually carried out in the presence of a base in a solvent at a temperature of $-20°$ C. to $300°$ C. for a period 0.5 to 20 hours. The compound (3) and the base are used in the respective amounts of 1.0 to 1.5 equivalents to one equivalent of the compound (2).

Examples of the solvent are aromatic hydrocarbons (e.g., benzene, toluene, xylene), halogenated hydrocarbons (e.g., chloroform, carbon tetrachloride, dichloroethane, chlorobenzene, dichlorobenzene), ethers (e.g., diethyl ether, diisopropyl ether, dioxane, tetrahydrofuran, diethylene glycol dimethyl ether), ketones (e.g., acetone, methyl ethyl ketone, methyl isobutyl ketone, isophorone, cyclohexanone), nitriles (e.g., acetonitrile, isobutyronitrile), tertiary amines (e.g., pyridine, triethylamine, N,N-diethylaniline, tributylamine, N-methylmorpholine), acid amides (e.g., formamide, N,N-dimethylformamide, acetamide), sulfur compounds (e.g., dimethylsulfoxide, sulphorane) and aqueous ammonia. These solvents may be used solely or in any combination.

As the base, there may be used an organic base (e.g., pyridine, triethylamine, N,N-diethylaniline), an inorganic base (e.g., sodium hydroxide, potassium hydroxide, sodium carbonate, potassium carbonate, sodium hydride), an alkali metal alkoxide (e.g., sodium methoxide, sodium ethoxide), an organometallic compound (e.g., butyl lithium, lithium diisopropyl amine) or the like.

After completion of the reaction, the reaction mixture is subjected to ordinary post-treatment. For example, the reaction mixture is poured into water and the precipitated crystals are collected by filtration, or extracted with an organic solvent and concentrated. Any purification technique such as chromatography, distillation or recrystallization may be applied to the resulting product, if necessary.

The compound (1) of the present invention wherein $R^1$ or $R^2$ is nitro can be converted into a certain compound having various substituents according to the following scheme:

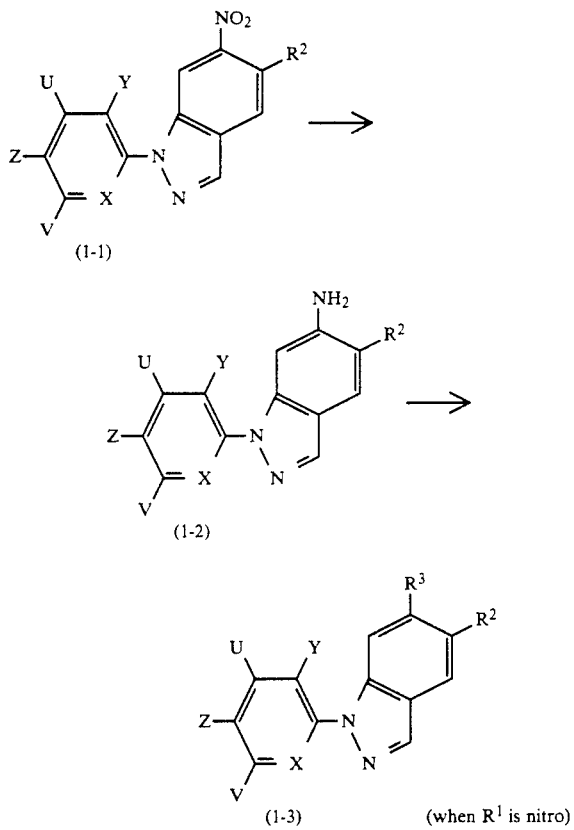

wherein $R^3$ is chlorine, bromine or cyano, X, Y, Z, U, V and $R^2$ are each as defined above. The reaction in the above scheme can be carried out according to the method as described, for example, in Organic Synthesis, 1514 (1941); Organic Synthesis, III, 185 (1955); Organic Synthesis, III, 295 (1955); or J. Org. Chem., 49, 2657 (1984).

Among the compounds of the present invention, the compound of the formula:

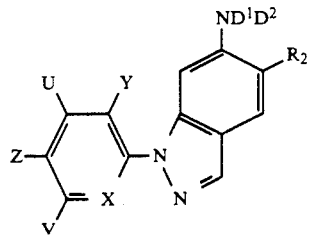

wherein X, Y, Z, U, V, $D^1$, $D^2$ and $R^2$ are each as defined above can also be produced from the compound (1-2) according to the method as described in WO 92/11244.

Among the compounds of the present invention, the compound wherein $R^1$ is a group of $-OB^1$ can also be produced according to the following scheme:

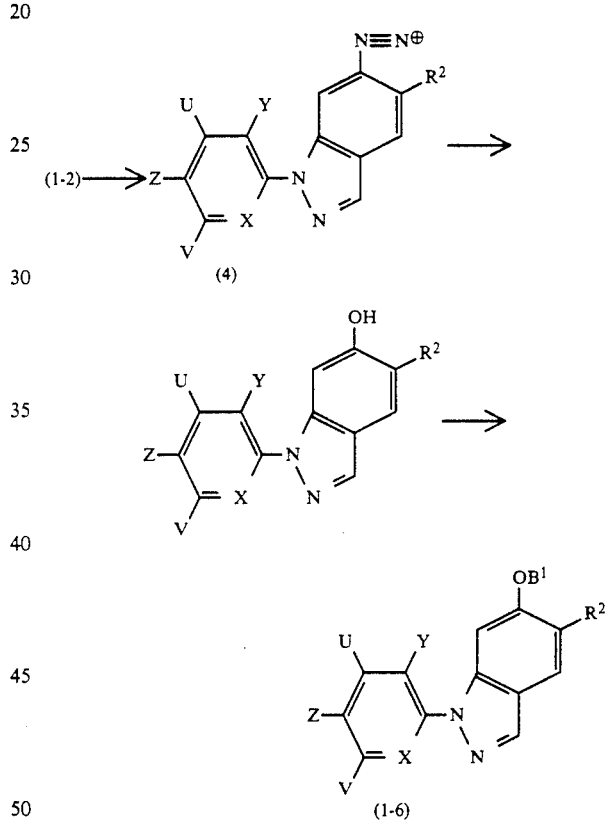

wherein X, Y, Z, U, V, $B^1$ and $R^2$ are each as defined above.

The compound (1-5) can be produced by reacting the compound (1-2) with sodium nitrite to obtain the compound as a diazo compound according to the method as described in Organic Synthesis, III, 130 (1955), and then allowing the diazo compound to decompose in diluted sulfuric acid.

The compound (1-6) can be produced by reacting a compound (1-5) with a compound of the formula:

$$W-B^1 \qquad (5)$$

wherein W and $B^1$ are each as defined above. The reaction is usually carried out in the presence of a base in a solvent at a temperature of 0° C. to 100° C. for a period of 0.5 to 20 hours. The compound (5) and the base are used in the respective amounts of 1.0 to 1.5 equivalents to one equivalent of the compound (1-5). Examples of the solvent are dimethylformamide, tetrahydrofuran and diethyl ether. Examples of the base are sodium hydride, potassium carbonate and pyridine.

Some of the compounds of the present invention may also be produced according to the following scheme:

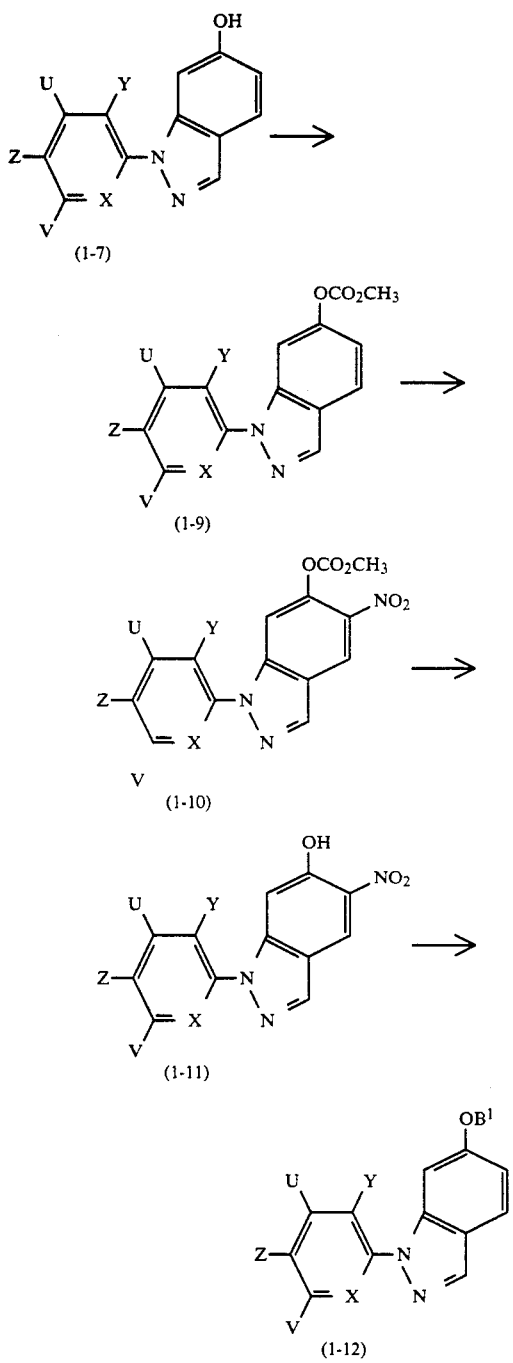

wherein X, Y, Z, U, V and $B^1$ are each as defined above.

The compound (1-9) can be produced by reacting the compound (1-7) with methoxycarbonyl chloride in the presence of a base (e.g., triethylamine) in a solvent (e.g., dichloromethane, tetrahydrofuran) at a temperature of 0° C. to 100° C. for a period of 0.5 to 10 hours. The methoxycarbonyl chloride and the base are used in an amount of 1.0 to 2.0 equivalents and in an amount of 1.0 to 5 equivalents, respectively, to one equivalent of the compound (1-7).

The compound (1-10) can be produced by reacting the compound (1-9) with nitric acid in sulfuric acid at a temperature of 0° C. to 40° C. for a period of 0.5 to 10 hours. The nitric acid are used in an amount of 1.0 to 1.2 equivalents to one equivalent of the compound (1-9).

The compound (1-11) can be produced by hydrolysis of the compound (1-10) under reflux in dilute sulfuric acid.

The compound (1-12) can be produced by reacting the compound (1-11) with the compound (5). The reaction is usually carried out in the presence of a base (e.g., sodium hydride, potassium carbonate) in a solvent (e.g., dimethyl formamide, acetone, tetrahydrofuran) at a temperature of 0° C. to 100° C. for a period of 0.5 to 10 hours. The compound (5) and the base are used in an amount of 1.0 to 10 equivalents and in an amount of 1.0 to 3.0 equivalents, respectively, to one equivalent of the compound (1-11).

Some of the compounds of the present invention may also be produced according to the following scheme:

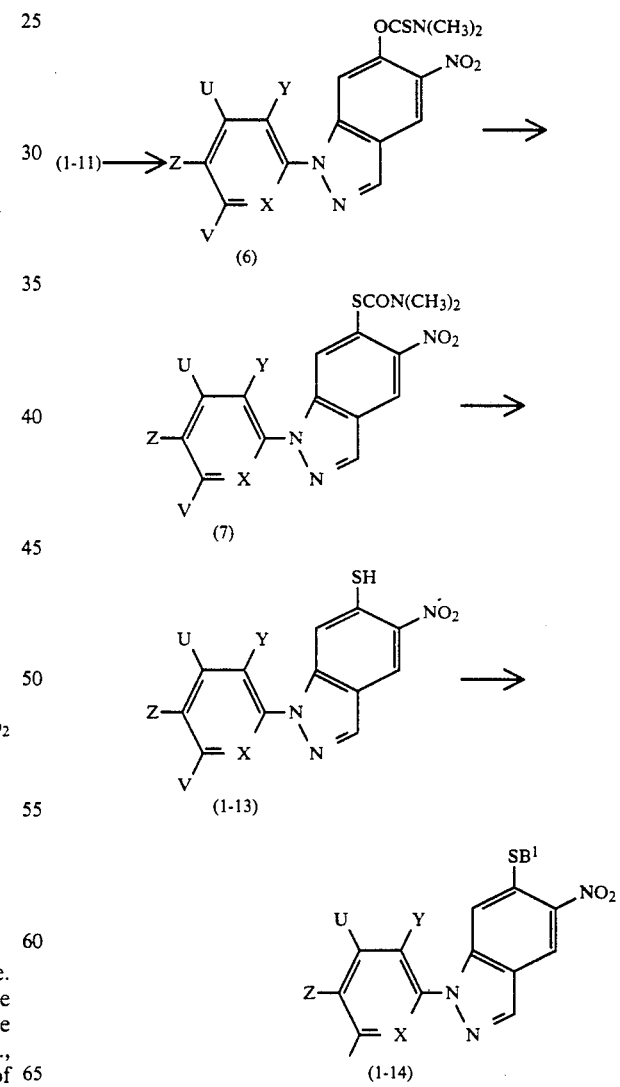

The compound (6) can be produced by reacting the compound (1-11) with N,N-dimethylthiocarbamoyl chloride. The reaction is usually carried out in the presence of a base (e.g., 1,4-diazabicyclo[2.2.2.]octane) in a solvent (e.g., N,N-dimethylformamide) at a temperature of 0° C. to 50° C. for a period of 0.5 to 10 hours. The N,N-dimethylthiocarbamoyl chloride and the base are used in an amount of 1.0 to 1.5 equivalents and in an amount of 1.0 to 3.0 equivalents, respectively, to one equivalent of the compound (1-11).

The compound (7) can be produced by thermal rearrangement of the compound (6) in a solvent (e.g., o-dichlorobenzene) at a temperature of 100° C. to 200° C. for a period of 0.5 to 24 hours.

The compound (1-13) can be produced by hydrolysis of the compound (7) under reflux in dilute sulfuric acid.

The compound (1-14) can be produced by reacting the compound (1-13) with the compound (5). The reaction is usually carried out in the presence of a base (e.g., sodium hydride, potassium carbonate) in a solvent (e.g., N,N-dimethylformamide, acetone, tetrahydrofuran) at a temperature of 0° C. to 100° C. for a period of 0.5 to 10 hours. The compound (5) and the base are used in amounts of 1.0 to equivalents and in amounts of 1.0 to 3.0 equivalents, respectively, to one equivalent of the compound (1-13).

Some of the compounds of the present invention may also be produced according to the following scheme:

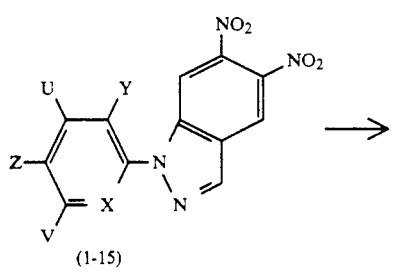
(1-15)

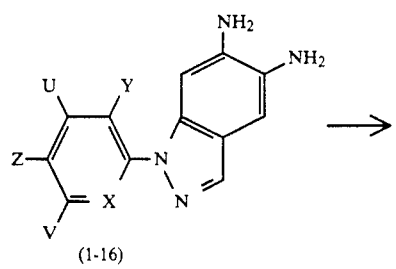
(1-16)

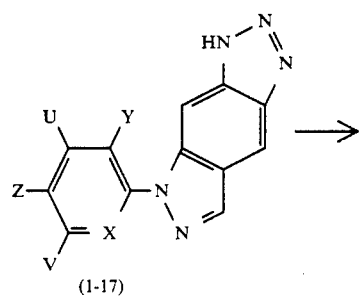
(1-17)

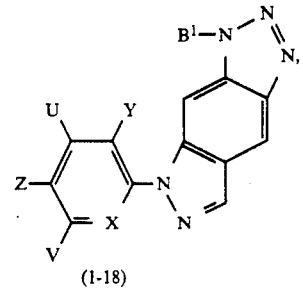
(1-18)

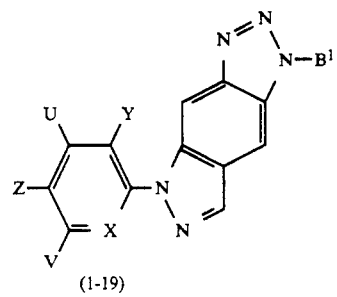
(1-19)

wherein X, Y, Z, U, V and $B^1$ are each as defined above.

The compound (1-16) can be produced by catalytic reduction of the compound (1-15) with hydrogen gas. The reaction is usually carried out in the presence of a catalyst (e.g., palladium carbon) in a solvent (e.g., ethyl acetate) at a temperature of 0° C. to 200° C. for a period of 0.5 to 20 hours. The hydrogen gas is used in an amount of 6 equivalents to one equivalent of the compound (1-15).

The compound (1-17) can be produced by reacting the compound (1-16) with sodium nitrite. The reaction is usually carried out in a solvent (e.g., acetic acid) at a temperature of 0° C. to 40° C. for a period of 0.5 to 10 hours. The sodium nitrite is used in an amount of 1.0 to 1.2 equivalents to one equivalent of the compound (1-16).

The compounds (1-18) and (1-19) can be produced by reacting the compound (1-17) with the compound (5). The reaction is usually carried out in the presence of a base (e.g., potassium carbonate) in a solvent (e.g., N,N-dimethylformamide) at a temperature of 0° C. to 100° C. for a period of 0.5 to 5 hours. The compound (5) and the base are used in the respective amounts of 1.0 to 2 equivalents to one equivalent of the compound (1-17).

Some of the compounds of the present invention may also be produced according to the following scheme:

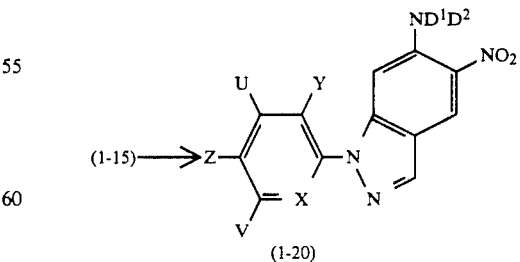
(1-20)

wherein X, Y, Z, U, V, $D^1$ and $D^2$ are each as defined above.

The compound (1-20) can be produced by reacting the compound (1-15) with a compound of the formula:

HND¹D² (8)

wherein D¹ and D² are each as defined above. The reaction is usually carried out in the presence of a base (e.g., triethylamine) in a solvent (e.g., acetonitrile, dichloromethane, N,N-dimethylformamide) at a temperature of 10° C. to 100° C. for a period of 0.5 to 20 hours. The compound (8) and the base are used in an amount of 1.0 to 2.0 equivalents and in an amount of 1.0 to 3.0 equivalents, respectively, to one equivalent of the compound (1-15).

Some of the compounds of the present invention may also be produced according to the following scheme:

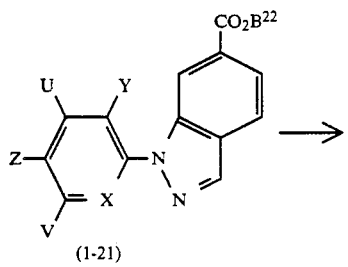
(1-21)

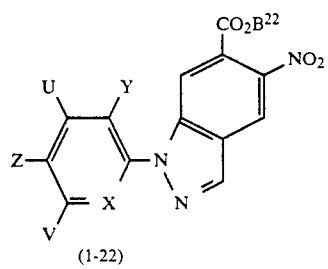
(1-22)

wherein X, Y, Z, U, V and B²² are each as defined above.

The compound (1-22) can be produced by reacting the compound (1-21) with nitric acid. The reaction is usually carried out in a solvent (e.g., sulfuric acid, acetic acid) at a temperature of 0° C. to 50° C. for a period of 0.5 to 5 hours. The nitric acid is used in an amount of 1.0 to 1.2 equivalents to one equivalent of the compound (1-21).

Some of the compounds of the present invention may also be produced according to the following scheme:

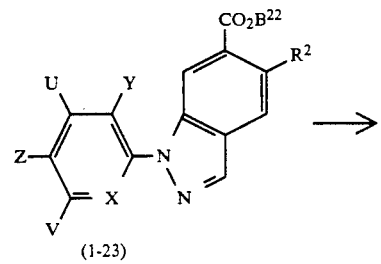
(1-23)

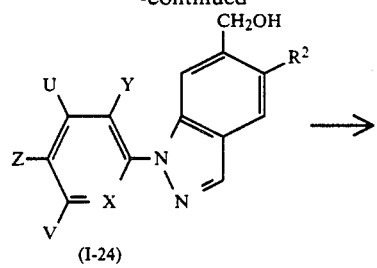
(1-24)

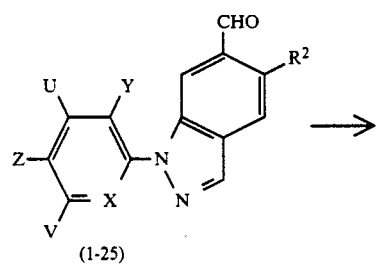
(1-25)

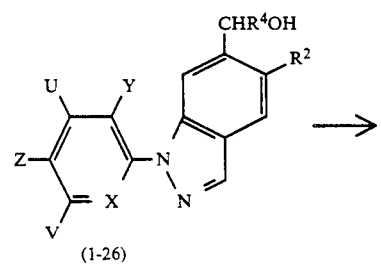
(1-26)

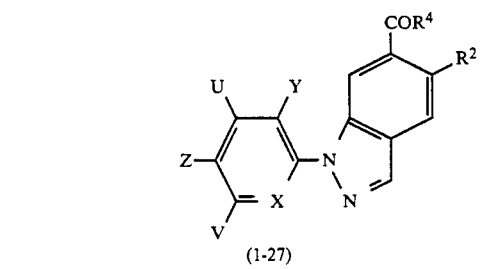
(1-27)

wherein $R^4$ is $C_1-C_4$ alkyl, and X, Y, Z, U, V, $B^{22}$ and $R^2$ are each as defined above.

The compound (1-24) can be produced by reduction of the compound (1-23) with a reducing agent (e.g., lithium aluminium hydride). The reaction is usually carried out in a solvent (e.g., diethyl ether, tetrahydrofuran) at a temperature of −70° C. to 50° C. for a period of 0.5 to 10 hours. The reducing agent is used in an amount of 1.0 to 1.2 equivalents to one equivalent of the compound (1-23).

The compound (1-25) can be produced by oxidation of the compound (1-24) with an oxidizing agent (e.g., pyridinium chlorochromate). The reaction is usually carried out in a solvent (e.g., dichloromethane) at a temperature of −70° C. to 50° C. for a period of 0.5 to 10 hours. The oxidizing agent is used in an amount of 1.0 to 1.2 equivalents to one equivalent of the compound (1-24).

The compound (1-26) can be produced by reacting the compound (1-25) with an alkylating agent (e.g., lithium alkyl). The reaction is usually carried out in a solvent (e.g., diethyl ether, tetrahydrofuran) at a temperature of −70° C. to 50° C. for a period of 0.5 to 10 hours. The alkylating agent is used in an amount of 1.0 to 1.2 equivalents of the compound (1-25).

The compound (1-27) can be produced by oxidation of the compound (1-26) with an oxidizing agent (e.g., pyridinium chlorochromate). The reaction is usually carried out in a solvent (e.g., dichloromethane) at a temperature of −70° C. to 50° C. for a period of 0.5 to 10 hours. The oxidizing agent is used in an amount of 1.0 to 3.0 equivalents to one equivalent of the compound (1-26)

Some of the compounds of the present invention may also be produced according to the following scheme:

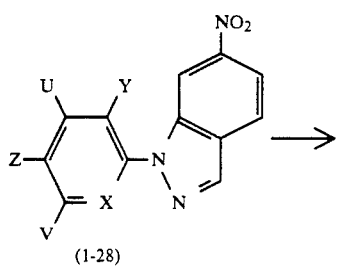

(1-28)

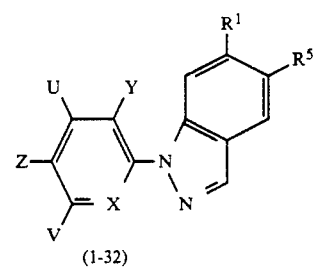

(1-29)

The compound (1-29) can be produced by reacting the compound (1-28) with a nitric acid. The reaction is usually carried out in sulfuric acid at a temperature of −10° C. to 100° C. for a period of 0.5 to 10 hours. The nitric acid is used in an amount of 1.0 to 1.5 equivalents to one equivalent of the compound (1-28).

Some of the compounds of the present invention may also be produced according to the following scheme.

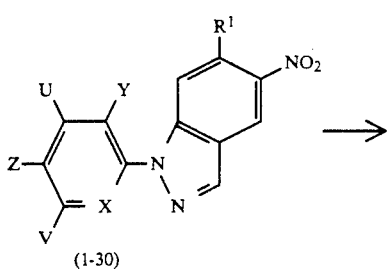

(1-30)

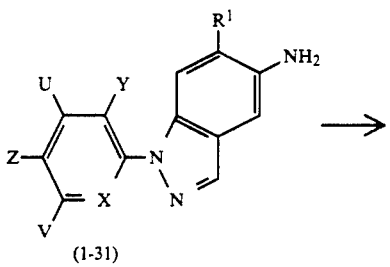

(1-31)

(9)

(1-32)

wherein $R^5$ is chloride, bromine or iodine, and X, Y, Z, U, V and $R^1$ are each as defined above.

The compound (1-31) can be produced by reduction of compound (1-30) with iron powder and water. The reduction is carried out in a solvent (e.g., acetic acid) at a temperature of 0° C. to 120° C. for a period of 0.5 to 10 hours. The iron powder and the water are used in the respective amounts of 3 to 10 equivalents to one equivalent of the compound (1-30).

The compound (9) can be produced by reacting the compound (1-31) with sodium nitrite. The reaction is usually carried out in a mineral acid of the formula:

$$HR^5 \qquad (10)$$

wherein $R^5$ is as defined above at a temperature of 0° C. to 20° C. for a period of 0.5 to 10 hours. The sodium nitrite is used in an amount of 1.0 to 2.0 equivalents to one equivalent of the compound (1-31).

The above solution of compound (9) can be used to react with a compound of the formula:

$$CuR^5 \qquad (11)$$

wherein $R^5$ is as defined above to obtain the compound (1-32). The reaction is usually carried out at a temperature of 0° C. to 100° C. for a period of 0.5 to 10 hours. The compound (11) is used in an amount of 1.0 to 3.0 equivalents to one equivalent of the compound (9).

According to the above procedures, the compounds (1) as shown in Table 1 are obtained.

TABLE 1

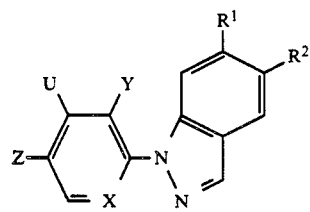

| X | Y | Z | U | V | R¹ | R² |
|---|---|---|---|---|----|----|
| N | Cl | $CF_3$ | H | H | H | Cl |
| N | Cl | $CF_3$ | H | H | H | Br |
| N | Cl | $CF_3$ | H | H | H | F |
| N | Cl | $CF_3$ | H | H | H | CN |
| N | Cl | $CF_3$ | H | H | H | $NO_2$ |
| CCl | Cl | $CF_3$ | H | H | H | Cl |
| CCl | Cl | $CF_3$ | H | H | H | Br |
| CCl | Cl | $CF_3$ | H | H | H | F |
| CCl | Cl | $CF_3$ | H | H | H | CN |
| CCl | Cl | $CF_3$ | H | H | H | $NO_2$ |
| CCl | F | $CF_3$ | H | H | H | Cl |
| CCl | F | $CF_3$ | H | H | H | Br |
| CCl | F | $CF_3$ | H | H | H | F |
| CCl | F | $CF_3$ | H | H | H | CN |
| CCl | F | $CF_3$ | H | H | H | $NO_2$ |
| CF | F | $CF_3$ | H | H | H | Cl |
| CF | F | $CF_3$ | H | H | H | Br |
| CF | F | $CF_3$ | H | H | H | F |
| CF | F | $CF_3$ | H | H | H | CN |
| CF | F | $CF_3$ | H | H | H | $NO_2$ |
| N | Cl | $CF_3$ | H | H | $OCH(CH_3)CO_2CH_3$ | H |
| N | Cl | $CF_3$ | H | H | $OCH(CH_3)CO_2C_2H_5$ | H |
| N | Cl | $CF_3$ | H | H | $OCH(CH_3)CO_2C_3H_7$ | H |
| N | Cl | $CF_3$ | H | H | $OCH(CH_3)CO_2C_4H_9$ | H |
| N | Cl | $CF_3$ | H | H | $OCH(CH_3)CO_2C_5H_{11}$ | H |
| N | Cl | $CF_3$ | H | H | $OCH(CH_3)CO_2H$ | H |
| N | Cl | $CF_3$ | H | H | $OCH(CH_3)CO_2K$ | H |
| N | Cl | $CF_3$ | H | H | $OCH(CH_3)CO_2Na$ | H |
| N | Cl | $CF_3$ | H | H | $OCH(CH_3)CO_2NH_4$ | H |
| N | Cl | $CF_3$ | H | H | $OCH(CH_3)CO_2CH_2CH=CH_2$ | H |
| N | Cl | $CF_3$ | H | H | $OCH(CH_3)CO_2CH_2C\equiv CH$ | H |
| N | Cl | $CF_3$ | H | H | $OCH(CH_3)CO_2CH_2OCH_3$ | H |
| N | Cl | $CF_3$ | H | H | $OCH(CH_3)CO_2$-cyclopentyl | H |
| N | Cl | $CF_3$ | H | H | $OCH(CH_3)CO_2$-cyclohexyl | H |
| N | Cl | $CF_3$ | H | H | $OCH(CH_3)CO_2CH_2F$ | H |
| N | Cl | $CF_3$ | H | H | $SCH(CH_3)CO_2CH_3$ | H |
| N | Cl | $CF_3$ | H | H | $SCH(CH_3)CO_2C_5H_{11}$ | H |
| N | Cl | $CF_3$ | H | H | $SCH(CH_3)CO_2H$ | H |
| N | Cl | $CF_3$ | H | H | $OCH_2CO_2H$ | H |
| N | Cl | $CF_3$ | H | H | $OCH_2CO_2CH_3$ | H |
| N | Cl | $CF_3$ | H | H | $OCH_2CO_2C_5H_{11}$ | H |
| N | Cl | $CF_3$ | H | H | $OCH_3$ | H |
| N | Cl | $CF_3$ | H | H | $OC_2H_5$ | H |
| N | Cl | $CF_3$ | H | H | $OC_3H_7$ | H |
| N | Cl | $CF_3$ | H | H | $OC_4H_9$ | H |
| N | Cl | $CF_3$ | H | H | $OC_5H_{11}$ | H |
| N | Cl | $CF_3$ | H | H | $OCH_2CH=CH_2$ | H |
| N | Cl | $CF_3$ | H | H | $OCH_2C\equiv CH$ | H |
| N | Cl | $CF_3$ | H | H | $OCH_2OCH_3$ | H |
| N | Cl | $CF_3$ | H | H | O-cyclopentyl | H |

TABLE 1-continued

| X | Y | Z | U | V | R¹ | R² |
|---|---|---|---|---|---|---|
| N | Cl | CF₃ | H | H | O-cyclohexyl | H |
| N | Cl | CF₃ | H | H | OCOCH₃ | H |
| N | Cl | CF₃ | H | H | OCOC₄H₉ | H |
| N | Cl | CF₃ | H | H | OCO₂CH₃ | H |
| N | Cl | CF₃ | H | H | OCO₂C₂H₅ | H |
| N | Cl | CF₃ | H | H | OCO₂C₃H₇ | H |
| N | Cl | CF₃ | H | H | OCH(CH₃)CH₂OH | H |
| N | Cl | CF₃ | H | H | OCH₂CH₂OH | H |
| N | Cl | CF₃ | H | H | SCH₂CH=CH₂ | H |
| H | Cl | CF₃ | H | H | SCH₂C≡CH | H |
| N | Cl | CF₃ | H | H | SCH₂CO₂CH₃ | H |
| N | Cl | CF₃ | H | H | SCH₂CO₂C₅H₁₁ | H |
| N | Cl | CF₃ | H | H | NHCH(CH₃)CO₂CH₃ | H |
| N | Cl | CF₃ | H | H | NHCH(CH₃)CO₂C₃H₇ | H |
| N | Cl | CF₃ | H | H | NHCH(CH₃)CO₂C₄H₉ | H |
| N | Cl | CF₃ | H | H | NHCH(CH₃)CO₂C₅H₁₁ | H |
| N | Cl | CF₃ | H | H | NHCH(CH₃)CO₂H | H |
| N | Cl | CF₃ | H | H | NHCH(CH₃)CO₂CH₂CH=CH₂ | H |
| N | Cl | CF₃ | H | H | NHCH(CH₃)CO₂CH₂C≡CH | H |
| N | Cl | CF₃ | H | H | NHCH(CH₃)CO₂-cyclopentyl | H |
| N | Cl | CF₃ | H | H | NHCH(CH₃)CO₂-cyclohexyl | H |
| N | Cl | CF₃ | H | H | NHCH₃ | H |
| N | Cl | CF₃ | H | H | NHC₂H₅ | H |
| N | Cl | CF₃ | H | H | NHC₃H₇ | H |
| N | Cl | CF₃ | H | H | NHC₄H₉ | H |
| N | Cl | CF₃ | H | H | NHC₅H₁₁ | H |
| N | Cl | CF₃ | H | H | NHCH₂CH=CH₂ | H |
| N | Cl | CF₃ | H | H | NHCH₂C≡CH | H |
| N | Cl | CF₃ | H | H | NHCH₂OCH₃ | H |
| N | Cl | CF₃ | H | H | NHCH₂CH₂F | H |
| N | Cl | CF₃ | H | H | NH-cyclopentyl | H |
| N | Cl | CF₃ | H | H | NH-cyclohexyl | H |
| N | Cl | CF₃ | H | H | NHCH(OCH₃)CO₂CH₃ | H |
| N | Cl | CF₃ | H | H | NHCH(OCH₃)CO₂C₅H₁₁ | H |
| N | Cl | CF₃ | H | H | NHCH₂CO₂H | H |
| N | Cl | CF₃ | H | H | NHCH₂CO₂CH₃ | H |
| N | Cl | CF₃ | H | H | NHCH₂CO₂C₂H₅ | H |
| N | Cl | CF₃ | H | H | NHCH₂CO₂C₃H₇ | H |
| N | Cl | CF₃ | H | H | NHCH₂CO₂C₄H₉ | H |
| N | Cl | CF₃ | H | H | NHSO₂CH₃ | H |
| N | Cl | CF₃ | H | H | NHSO₂C₂H₅ | H |
| N | Cl | CF₃ | H | H | NHSO₂C₃H₇ | H |
| N | Cl | CF₃ | H | H | NHSO₂C₄H₉ | H |

TABLE 1-continued

| X | Y | Z | U | V | R$^1$ | R$^2$ |
|---|---|---|---|---|---|---|
| N | Cl | CF$_3$ | H | H | NHSO$_2$CH$_2$Cl | H |
| N | Cl | CF$_3$ | H | H | NHSO$_2$CH$_2$CH$_2$CH$_2$Cl | H |
| N | Cl | CF$_3$ | H | H | NCH(CH$_3$)CO$_2$C$_2$H$_5$ \| SO$_2$CH$_3$ | H |
| N | Cl | CF$_3$ | H | H | NCH$_2$CH=CH$_2$ \| SO$_2$CH$_3$ | H |
| N | Cl | CF$_3$ | H | H | NCH$_2$C≡CH \| SO$_2$CH$_3$ | H |
| N | Cl | CF$_3$ | H | H | NCH(OCH$_3$)CO$_2$CH$_3$ \| SO$_2$CH$_3$ | H |
| N | Cl | CF$_3$ | H | H | N(SO$_2$CH$_3$)$_2$ | H |
| N | Cl | CF$_3$ | H | H | CO$_2$H | H |
| N | Cl | CF$_3$ | H | H | CO$_2$CH$_3$ | H |
| N | Cl | CF$_3$ | H | H | CO$_2$C$_2$H$_5$ | H |
| N | Cl | CF$_3$ | H | H | CO$_2$C$_3$H$_7$ | H |
| N | Cl | CF$_3$ | H | H | CO$_2$C$_4$H$_9$ | H |
| N | Cl | CF$_3$ | H | H | CO$_2$C$_5$H$_{11}$ | H |
| N | Cl | CF$_3$ | H | H | CO$_2$CH$_2$CH=CH$_2$ | H |
| N | Cl | CF$_3$ | H | H | CO$_2$CH$_2$C≡CH | H |
| N | Cl | CF$_3$ | H | H | CO$_2$CH$_2$OCH$_3$ | H |
| N | Cl | CF$_3$ | H | H | CO$_2$-cyclopentyl | H |
| N | Cl | CF$_3$ | H | H | CO$_2$-cyclohexyl | H |
| N | Cl | CF$_3$ | H | H | CO$_2$CH$_2$CH$_2$F | H |
| N | Cl | CF$_3$ | H | H | CHO | H |
| N | Cl | CF$_3$ | H | H | COCH$_3$ | H |
| N | Cl | CF$_3$ | H | H | COCH$_2$OCH$_3$ | H |
| N | Cl | CF$_3$ | H | H | CH$_2$OH | H |
| N | Cl | CF$_3$ | H | H | CH(OH)CH$_3$ | H |
| N | Cl | CF$_3$ | H | H | OCH(CH$_3$)CO$_2$CH$_3$ | NO$_2$ |
| N | Cl | CF$_3$ | H | H | OCH(CH$_3$)CO$_2$C$_2$H$_5$ | NO$_2$ |
| N | Cl | CF$_3$ | H | H | OCH(CH$_3$)CO$_2$C$_3$H$_7$ | NO$_2$ |
| N | Cl | CF$_3$ | H | H | OCH(CH$_3$)CO$_2$C$_4$H$_9$ | NO$_2$ |
| N | Cl | CF$_3$ | H | H | OCH(CH$_3$)CO$_2$C$_5$H$_{11}$ | NO$_2$ |
| N | Cl | CF$_3$ | H | H | OCH(CH$_3$)CO$_2$H | NO$_2$ |
| N | Cl | CF$_3$ | H | H | OCH(CH$_3$)CO$_2$K | NO$_2$ |
| N | Cl | CF$_3$ | H | H | OCH(CH$_3$)CO$_2$Na | NO$_2$ |
| N | Cl | CF$_3$ | H | H | OCH(CH$_3$)CO$_2$NH$_4$ | NO$_2$ |
| N | Cl | CF$_3$ | H | H | OCH(CH$_3$)CO$_2$CH$_2$CH=CH$_2$ | NO$_2$ |
| N | Cl | CF$_3$ | H | H | OCH(CH$_3$)CO$_2$CH$_2$C≡CH | NO$_2$ |
| N | Cl | CF$_3$ | H | H | OCH(CH$_3$)CO$_2$CH$_2$OCH$_3$ | NO$_2$ |
| N | Cl | CF$_3$ | H | H | OCH(CH$_3$)CO$_2$-cyclopentyl | NO$_2$ |

TABLE 1-continued

| X | Y | Z | U | V | R¹ | R² |
|---|---|---|---|---|-----|-----|
| N | Cl | CF₃ | H | H | OCH(CH₃)CO₂-cyclohexyl | NO₂ |
| N | Cl | CF₃ | H | H | OCH(CH₃)CO₂CH₂F | NO₂ |
| N | Cl | CF₃ | H | H | SCH(CH₃)CO₂CH₃ | NO₂ |
| N | Cl | CF₃ | H | H | SCH(CH₃)CO₂C₅H₁₁ | NO₂ |
| N | Cl | CF₃ | H | H | SCH(CH₃)CO₂H | NO₂ |
| N | Cl | CF₃ | H | H | OCH₂CO₂H | NO₂ |
| N | Cl | CF₃ | H | H | OCH₂CO₂CH₃ | NO₂ |
| N | Cl | CF₃ | H | H | OCH₂CO₂C₅H₁₁ | NO₂ |
| N | Cl | CF₃ | H | H | OCH₃ | NO₂ |
| N | Cl | CF₃ | H | H | OC₂H₅ | NO₂ |
| N | Cl | CF₃ | H | H | OC₃H₇ | NO₂ |
| N | Cl | CF₃ | H | H | OC₄H₉ | NO₂ |
| N | Cl | CF₃ | H | H | OC₅H₁₁ | NO₂ |
| N | Cl | CF₃ | H | H | OCH₂CH=CH₂ | NO₂ |
| N | Cl | CF₃ | H | H | OCH₂C≡CH | NO₂ |
| N | Cl | CF₃ | H | H | OCH₂OCH₃ | NO₂ |
| N | Cl | CF₃ | H | H | O-cyclopentyl | NO₂ |
| N | Cl | CF₃ | H | H | O-cyclohexyl | NO₂ |
| N | Cl | CF₃ | H | H | OCOCH₃ | NO₂ |
| N | Cl | CF₃ | H | H | OCOC₄H₉ | NO₂ |
| N | Cl | CF₃ | H | H | OCO₂CH₃ | NO₂ |
| N | Cl | CF₃ | H | H | OCO₂C₂H₅ | NO₂ |
| N | Cl | CF₃ | H | H | OCO₂C₃H₇ | NO₂ |
| N | Cl | CF₃ | H | H | OCH(CH₃)CH₂OH | NO₂ |
| N | Cl | CF₃ | H | H | OCH₂CH₂OH | NO₂ |
| N | Cl | CF₃ | H | H | SCH₂CH=CH₂ | NO₂ |
| H | Cl | CF₃ | H | H | SCH₂C≡CH | NO₂ |
| N | Cl | CF₃ | H | H | SCH₂CO₂CH₃ | NO₂ |
| N | Cl | CF₃ | H | H | SCH₂CO₂C₅H₁₁ | NO₂ |
| N | Cl | CF₃ | H | H | NHCH(CH₃)CO₂CH₃ | NO₂ |
| N | Cl | CF₃ | H | H | NHCH(CH₃)CO₂C₂H₅ | NO₂ |
| N | Cl | CF₃ | H | H | NHCH(CH₃)CO₂C₃H₇ | NO₂ |
| N | Cl | CF₃ | H | H | NHCH(CH₃)CO₂C₄H₉ | NO₂ |
| N | Cl | CF₃ | H | H | NHCH(CH₃)CO₂C₅H₁₁ | NO₂ |
| N | Cl | CF₃ | H | H | NHCH(CH₃)CO₂H | NO₂ |
| N | Cl | CF₃ | H | H | NHCH(CH₃)CO₂CH₂CH=CH₂ | NO₂ |
| N | Cl | CF₃ | H | H | NHCH(CH₃)CO₂CH₂C≡CH | NO₂ |
| N | Cl | CF₃ | H | H | NHCH(CH₃)CO₂-cyclopentyl | NO₂ |
| N | Cl | CF₃ | H | H | NHCH(CH₃)CO₂-cyclohexyl | NO₂ |
| N | Cl | CF₃ | H | H | NHCH₃ | NO₂ |
| N | Cl | CF₃ | H | H | NHC₂H₅ | NO₂ |
| N | Cl | CF₃ | H | H | NHC₃H₇ | NO₂ |
| N | Cl | CF₃ | H | H | NHC₄H₉ | NO₂ |

TABLE 1-continued

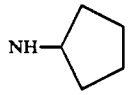

| X | Y | Z | U | V | R¹ | R² |
|---|---|---|---|---|---|---|
| N | Cl | $CF_3$ | H | H | $NHC_5H_{11}$ | $NO_2$ |
| N | Cl | $CF_3$ | H | H | $NHCH_2CH=CH_2$ | $NO_2$ |
| N | Cl | $CF_3$ | H | H | $NHCH_2C\equiv CH$ | $NO_2$ |
| N | Cl | $CF_3$ | H | H | $NHCH_2OCH_3$ | $NO_2$ |
| N | Cl | $CF_3$ | H | H | $NHCH_2CH_2F$ | $NO_2$ |
| N | Cl | $CF_3$ | H | H | 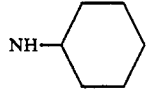 | $NO_2$ |
| N | Cl | $CF_3$ | H | H | 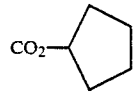 | $NO_2$ |
| N | Cl | $CF_3$ | H | H | $NHCH(OCH_3)CO_2CH_3$ | $NO_2$ |
| N | Cl | $CF_3$ | H | H | $NHCH(OCH_3)CO_2C_5H_{11}$ | $NO_2$ |
| N | Cl | $CF_3$ | H | H | $NHCH_2CO_2H$ | $NO_2$ |
| N | Cl | $CF_3$ | H | H | $NHCH_2CO_2CH_3$ | $NO_2$ |
| N | Cl | $CF_3$ | H | H | $NHCH_2CO_2C_2H_5$ | $NO_2$ |
| N | Cl | $CF_3$ | H | H | $NHCH_2CO_2C_3H_7$ | $NO_2$ |
| N | Cl | $CF_3$ | H | H | $NHCH_2CO_2C_4H_9$ | $NO_2$ |
| N | Cl | $CF_3$ | H | H | $NHSO_2CH_3$ | $NO_2$ |
| N | Cl | $CF_3$ | H | H | $NHSO_2C_2H_5$ | $NO_2$ |
| N | Cl | $CF_3$ | H | H | $NHSO_2C_3H_7$ | $NO_2$ |
| N | Cl | $CF_3$ | H | H | $NHSO_2C_4H_9$ | $NO_2$ |
| N | Cl | $CF_3$ | H | H | $NHSO_2CH_2Cl$ | $NO_2$ |
| N | Cl | $CF_3$ | H | H | $NHSO_2CH_2CH_2Cl$ | $NO_2$ |
| N | Cl | $CF_3$ | H | H | $NHSO_2CH_2CH_2CH_2Cl$ | $NO_2$ |
| N | Cl | $CF_3$ | H | H | $NCH(CH_3)CO_2C_2H_5$<br>\|<br>$SO_2CH_3$ | $NO_2$ |
| N | Cl | $CF_3$ | H | H | $NCH_2CH=CH_2$<br>\|<br>$SO_2CH_3$ | $NO_2$ |
| N | Cl | $CF_3$ | H | H | $NCH_2C\equiv CH$<br>\|<br>$SO_2CH_3$ | $NO_2$ |
| N | Cl | $CF_3$ | H | H | $NCH(OCH_3)CO_2CH_3$<br>\|<br>$SO_2CH_3$ | $NO_2$ |
| N | Cl | $CF_3$ | H | H | $N(SO_2CH_3)_2$ | $NO_2$ |
| N | Cl | $CF_3$ | H | H | $CO_2H$ | $NO_2$ |
| N | Cl | $CF_3$ | H | H | $CO_2CH_3$ | $NO_2$ |
| N | Cl | $CF_3$ | H | H | $CO_2C_2H_5$ | $NO_2$ |
| N | Cl | $CF_3$ | H | H | $CO_2C_3H_7$ | $NO_2$ |
| N | Cl | $CF_3$ | H | H | $CO_2C_4H_9$ | $NO_2$ |
| N | Cl | $CF_3$ | H | H | $CO_2C_5H_{11}$ | $NO_2$ |
| N | Cl | $CF_3$ | H | H | $CO_2CH_2CH=CH_2$ | $NO_2$ |
| N | Cl | $CF_3$ | H | H | $CO_2CH_2C\equiv CH$ | $NO_2$ |
| N | Cl | $CF_3$ | H | H | $CO_2CH_2OCH_3$ | $NO_2$ |
| N | Cl | $CF_3$ | H | H |  | $NO_2$ |

TABLE 1-continued

| X | Y | Z | U | V | R¹ | R² |
|---|---|---|---|---|---|---|
| N | Cl | CF₃ | H | H | CO₂-cyclohexyl | NO₂ |
| N | Cl | CF₃ | H | H | CO₂CH₂CH₂F | NO₂ |
| N | Cl | CF₃ | H | H | CHO | NO₂ |
| N | Cl | CF₃ | H | H | COCH₃ | NO₂ |
| N | Cl | CF₃ | H | H | COCH₂OCH₃ | NO₂ |
| N | Cl | CF₃ | H | H | CH₂OH | NO₂ |
| N | Cl | CF₃ | H | H | CH(OH)CH₃ | NO₂ |
| N | Cl | CF₃ | H | H | OCH₃ | CN |
| N | Cl | CF₃ | H | H | OC₂H₅ | CN |
| N | Cl | CF₃ | H | H | OC₃H₇ | CN |
| N | Cl | CF₃ | H | H | OCH₃ | Cl |
| N | Cl | CF₃ | H | H | OC₂H₅ | Cl |
| N | Cl | CF₃ | H | H | OC₃H₇ | Cl |
| N | Cl | CF₃ | H | H | OCH₃ | Br |
| N | Cl | CF₃ | H | H | OCH₃ | F |
| N | Cl | CF₃ | H | H | OCH₂CH=CH₂ | CN |
| N | Cl | CF₃ | H | H | OCH₂CH=CH₂ | Cl |
| N | Cl | CF₃ | H | H | OCH₂CH=CH₂ | Br |
| N | Cl | CF₃ | H | H | OCH₂CH=CH₂ | F |
| N | Cl | CF₃ | H | H | OCH₂C≡CH | CN |
| N | Cl | CF₃ | H | H | OCH₂C≡CH | Cl |
| N | Cl | CF₃ | H | H | OCH₂C≡CH | Br |
| N | Cl | CF₃ | H | H | OCH₂C≡CH | F |
| N | Cl | CF₃ | H | H | OCH(CH₃)CO₂C₂H₅ | CN |
| N | Cl | CF₃ | H | H | OCH(CH₃)CO₂C₂H₅ | Cl |
| N | Cl | CF₃ | H | H | OCH(CH₃)CO₂C₂H₅ | Br |
| N | Cl | CF₃ | H | H | OCH(CH₃)CO₂C₂H₅ | F |
| N | Cl | CF₃ | H | H | NHCH₂CH=CH₂ | CN |
| N | Cl | CF₃ | H | H | NHCH₂C≡CH | Br |
| N | Cl | CF₃ | H | H | NHCH₂C≡CH | Cl |
| N | Cl | CF₃ | H | H | NHCH₂C≡CH | F |
| N | Cl | CF₃ | H | H | NHCH(CH₃)CO₂CH₃ | CN |
| N | Cl | CF₃ | H | H | NHCH(CH₃)CO₂CH₃ | Cl |
| N | Cl | CF₃ | H | H | NHCH(CH₃)CO₂CH₃ | Br |
| N | Cl | CF₃ | H | H | NHCH(CH₃)CO₂CH₃ | F |
| N | Cl | CF₃ | H | H | NHSO₂CH₃ | CN |
| N | Cl | CF₃ | H | H | NHSO₂CH₃ | Cl |
| N | Cl | CF₃ | H | H | NHSO₂CH₃ | Br |
| N | Cl | CF₃ | H | H | NHSO₂CH₃ | F |
| N | Cl | CF₃ | H | H | SCH(CH₃)CO₂C₂H₅ | CN |
| N | Cl | CF₃ | H | H | SCH(CH₃)CO₂C₂H₅ | Cl |
| N | Cl | CF₃ | H | H | SCH(CH₃)CO₂C₂H₅ | Br |
| N | Cl | CF₃ | H | H | SCH(CH₃)CO₂C₂H₅ | F |
| N | Cl | CF₃ | H | H | CO₂C₂H₅ | CN |
| N | Cl | CF₃ | H | H | CO₂C₂H₅ | Br |
| N | Cl | CF₃ | H | H | CO₂C₂H₅ | Cl |
| N | Cl | CF₃ | H | H | CO₂C₂H₅ | F |
| N | Cl | CF₃ | H | H | NO₂ | NO₂ |
| N | Cl | CF₃ | H | H | CN | NO₂ |
| CCl | Cl | CF₃ | H | H | OCH(CH₃)CO₂CH₃ | H |
| CCl | Cl | CF₃ | H | H | OCH(CH₃)CO₂C₂H₅ | H |
| CCl | Cl | CF₃ | H | H | OCH(CH₃)CO₂C₃H₇ | H |
| CCl | Cl | CF₃ | H | H | OCH(CH₃)CO₂C₄H₉ | H |
| CCl | Cl | CF₃ | H | H | OCH(CH₃)CO₂C₅H₁₁ | H |
| CCl | Cl | CF₃ | H | H | OCH(CH₃)CO₂H | H |
| CCl | Cl | CF₃ | H | H | OCH(CH₃)CO₂K | H |
| CCl | Cl | CF₃ | H | H | OCH(CH₃)CO₂Na | H |
| CCl | Cl | CF₃ | H | H | OCH(CH₃)CO₂NH₄ | H |
| CCl | Cl | CF₃ | H | H | OCH(CH₃)CO₂CH₂CH=CH₂ | H |
| CCl | Cl | CF₃ | H | H | OCH(CH₃)CO₂CH₂C≡CH | H |
| CCl | Cl | CF₃ | H | H | OCH(CH₃)CO₂CH₂OCH₃ | H |

TABLE 1-continued

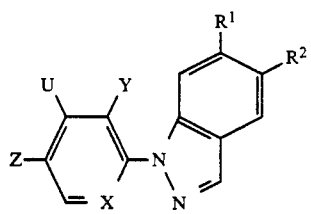

| X | Y | Z | U | V | R¹ | R² |
|---|---|---|---|---|---|---|
| CCl | Cl | CF₃ | H | H | OCH(CH₃)CO₂-cyclopentyl | H |
| CCl | Cl | CF₃ | H | H | OCH(CH₃)CO₂-cyclohexyl | H |
| CCl | Cl | CF₃ | H | H | OCH(CH₃)CO₂CH₂F | H |
| CCl | Cl | CF₃ | H | H | SCH(CH₃)CO₂CH₃ | H |
| CCl | Cl | CF₃ | H | H | SCH(CH₃)CO₂C₅H₁₁ | H |
| CCl | Cl | CF₃ | H | H | SCH(CH₃)CO₂H | H |
| CCl | Cl | CF₃ | H | H | OCH₂CO₂H | H |
| CCl | Cl | CF₃ | H | H | OCH₂CO₂CH₃ | H |
| CCl | Cl | CF₃ | H | H | OCH₂CO₂C₅H₁₁ | H |
| CCl | Cl | CF₃ | H | H | OCH₃ | H |
| CCl | Cl | CF₃ | H | H | OC₂H₅ | H |
| CCl | Cl | CF₃ | H | H | OC₃H₇ | H |
| CCl | Cl | CF₃ | H | H | OC₄H₉ | H |
| CCl | Cl | CF₃ | H | H | OC₅H₁₁ | H |
| CCl | Cl | CF₃ | H | H | OCH₂CH=CH₂ | H |
| CCl | Cl | CF₃ | H | H | OCH₂C≡CH | H |
| CCl | Cl | CF₃ | H | H | OCH₂OCH₃ | H |
| CCl | Cl | CF₃ | H | H | O-cyclopentyl | H |
| CCl | Cl | CF₃ | H | H | O-cyclohexyl | H |
| CCl | Cl | CF₃ | H | H | OCOCH₃ | H |
| CCl | Cl | CF₃ | H | H | OCOC₄H₉ | H |
| CCl | Cl | CF₃ | H | H | OCO₂CH₃ | H |
| CCl | Cl | CF₃ | H | H | OCO₂C₂H₅ | H |
| CCl | Cl | CF₃ | H | H | OCO₂C₃H₇ | H |
| CCl | Cl | CF₃ | H | H | OCH(CH₃)CH₂OH | H |
| CCl | Cl | CF₃ | H | H | OCH₂CH₂OH | H |
| CCl | Cl | CF₃ | H | H | SCH₂CH=CH₂ | H |
| CCl | Cl | CF₃ | H | H | SCH₂C≡CH | H |
| CCl | Cl | CF₃ | H | H | SCH₂CO₂CH₃ | H |
| CCl | Cl | CF₃ | H | H | SCH₂CO₂C₅H₁₁ | H |
| CCl | Cl | CF₃ | H | H | NHCH(CH₃)CO₂CH₃ | H |
| CCl | Cl | CF₃ | H | H | NHCH(CH₃)CO₂C₂H₅ | H |
| CCl | Cl | CF₃ | H | H | NHCH(CH₃)CO₂C₃H₇ | H |
| CCl | Cl | CF₃ | H | H | NHCH(CH₃)CO₂C₄H₉ | H |
| CCl | Cl | CF₃ | H | H | NHCH(CH₃)CO₂C₅H₁₁ | H |
| CCl | Cl | CF₃ | H | H | NHCH(CH₃)CO₂H | H |
| CCl | Cl | CF₃ | H | H | NHCH(CH₃)CO₂CH₂CH=CH₂ | H |
| CCl | Cl | CF₃ | H | H | NHCH(CH₃)CO₂CH₂C≡CH | H |
| CCl | Cl | CF₃ | H | H | NHCH(CH₃)CO₂-cyclopentyl | H |

TABLE 1-continued

| X | Y | Z | U | V | R¹ | R² |
|---|---|---|---|---|---|---|
| CCl | Cl | CF$_3$ | H | H | NHCH(CH$_3$)CO$_2$— 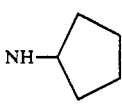 | H |
| CCl | Cl | CF$_3$ | H | H | NHCH$_3$ | H |
| CCl | Cl | CF$_3$ | H | H | NHC$_2$H$_5$ | H |
| CCl | Cl | CF$_3$ | H | H | NHC$_3$H$_7$ | H |
| CCl | Cl | CF$_3$ | H | H | NHC$_4$H$_9$ | H |
| CCl | Cl | CF$_3$ | H | H | NHC$_5$H$_{11}$ | H |
| CCl | Cl | CF$_3$ | H | H | NHCH$_2$CH=CH$_2$ | H |
| CCl | Cl | CF$_3$ | H | H | NHCH$_2$C≡CH | H |
| CCl | Cl | CF$_3$ | H | H | NHCH$_2$OCH$_3$ | H |
| CCl | Cl | CF$_3$ | H | H | NHCH$_2$CH$_2$F | H |
| CCl | Cl | CF$_3$ | H | H | NH-cyclopentyl | H |
| CCl | Cl | CF$_3$ | H | H | NH-cyclohexyl 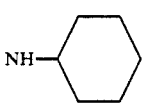 | H |
| CCl | Cl | CF$_3$ | H | H | NHCH(OCH$_3$)CO$_2$CH$_3$ | H |
| CCl | Cl | CF$_3$ | H | H | NHCH(OCH$_3$)CO$_2$C$_5$H$_{11}$ | H |
| CCl | Cl | CF$_3$ | H | H | NHCH$_2$CO$_2$H | H |
| CCl | Cl | CF$_3$ | H | H | NHCH$_2$CO$_2$CH$_3$ | H |
| CCl | Cl | CF$_3$ | H | H | NHCH$_2$CO$_2$C$_2$H$_5$ | H |
| CCl | Cl | CF$_3$ | H | H | NHCH$_2$CO$_2$C$_3$H$_7$ | H |
| CCl | Cl | CF$_3$ | H | H | NHCH$_2$CO$_2$C$_4$H$_9$ | H |
| CCl | Cl | CF$_3$ | H | H | NHSO$_2$CH$_3$ | H |
| CCl | Cl | CF$_3$ | H | H | NHSO$_2$C$_2$H$_5$ | H |
| CCl | Cl | CF$_3$ | H | H | NHSO$_2$C$_3$H$_7$ | H |
| CCl | Cl | CF$_3$ | H | H | NHSO$_2$C$_4$H$_9$ | H |
| CCl | Cl | CF$_3$ | H | H | NHSO$_2$CH$_2$Cl | H |
| CCl | Cl | CF$_3$ | H | H | NHSO$_2$CH$_2$CH$_2$Cl | H |
| CCl | Cl | CF$_3$ | H | H | NHSO$_2$CH$_2$CH$_2$CH$_2$Cl | H |
| CCl | Cl | CF$_3$ | H | H | N(CH(CH$_3$)CO$_2$C$_2$H$_5$)(SO$_2$CH$_3$) | H |
| CCl | Cl | CF$_3$ | H | H | N(CH$_2$CH=CH$_2$)(SO$_2$CH$_3$) | H |
| CCl | Cl | CF$_3$ | H | H | N(CH$_2$C≡CH)(SO$_2$CH$_3$) | H |
| CCl | Cl | CF$_3$ | H | H | N(CH(OCH$_3$)CO$_2$CH$_3$)(SO$_2$CH$_3$) | H |
| CCl | Cl | CF$_3$ | H | H | N(SO$_2$CH$_3$)$_2$ | H |
| CCl | Cl | CF$_3$ | H | H | CO$_2$H | H |
| CCl | Cl | CF$_3$ | H | H | CO$_2$CH$_3$ | H |
| CCl | Cl | CF$_3$ | H | H | CO$_2$C$_2$H$_5$ | H |
| CCl | Cl | CF$_3$ | H | H | CO$_2$C$_3$H$_7$ | H |
| CCl | Cl | CF$_3$ | H | H | CO$_2$C$_4$H$_9$ | H |
| CCl | Cl | CF$_3$ | H | H | CO$_2$C$_5$H$_{11}$ | H |
| CCl | Cl | CF$_3$ | H | H | CO$_2$CH$_2$CH=CH$_2$ | H |
| CCl | Cl | CF$_3$ | H | H | CO$_2$CH$_2$C≡CH | H |
| CCl | Cl | CF$_3$ | H | H | CO$_2$CH$_2$OCH$_3$ | H |

TABLE 1-continued

| X | Y | Z | U | V | R¹ | R² |
|---|---|---|---|---|---|---|
| CCl | Cl | CF₃ | H | H | CO₂-cyclopentyl | H |
| CCl | Cl | CF₃ | H | H | CO₂-cyclohexyl | H |
| CCl | Cl | CF₃ | H | H | CO₂CH₂CH₂F | H |
| CCl | Cl | CF₃ | H | H | CHO | H |
| CCl | Cl | CF₃ | H | H | COCH₃ | H |
| CCl | Cl | CF₃ | H | H | COCH₂OCH₃ | H |
| CCl | Cl | CF₃ | H | H | CH₂OH | H |
| CCl | Cl | CF₃ | H | H | CH(OH)CH₃ | H |
| CCl | Cl | CF₃ | H | H | OCH(CH₃)CO₂CH₃ | NO₂ |
| CCl | Cl | CF₃ | H | H | OCH(CH₃)CO₂C₂H₅ | NO₂ |
| CCl | Cl | CF₃ | H | H | OCH(CH₃)CO₂C₃H₇ | NO₂ |
| CCl | Cl | CF₃ | H | H | OCH(CH₃)CO₂C₄H₉ | NO₂ |
| CCl | Cl | CF₃ | H | H | OCH(CH₃)CO₂C₅H₁₁ | NO₂ |
| CCl | Cl | CF₃ | H | H | OCH(CH₃)CO₂H | NO₂ |
| CCl | Cl | CF₃ | H | H | OCH(CH₃)CO₂K | NO₂ |
| CCl | Cl | CF₃ | H | H | OCH(CH₃)CO₂Na | NO₂ |
| CCl | Cl | CF₃ | H | H | OCH(CH₃)CO₂NH₄ | NO₂ |
| CCl | Cl | CF₃ | H | H | OCH(CH₃)CO₂CH₂CH=CH₂ | NO₂ |
| CCl | Cl | CF₃ | H | H | OCH(CH₃)CO₂CH₂C≡CH | NO₂ |
| CCl | Cl | CF₃ | H | H | OCH(CH₃)CO₂CH₂OCH₃ | NO₂ |
| CCl | Cl | CF₃ | H | H | OCH(CH₃)CO₂-cyclopentyl | NO₂ |
| CCl | Cl | CF₃ | H | H | OCH(CH₃)CO₂-cyclohexyl | NO₂ |
| CCl | Cl | CF₃ | H | H | OCH(CH₃)CO₂CH₂F | NO₂ |
| CCl | Cl | CF₃ | H | H | SCH(CH₃)CO₂CH₃ | NO₂ |
| CCl | Cl | CF₃ | H | H | SCH(CH₃)CO₂C₅H₁₁ | NO₂ |
| CCl | Cl | CF₃ | H | H | SCH(CH₃)CO₂H | NO₂ |
| CCl | Cl | CF₃ | H | H | OCH₂CO₂H | NO₂ |
| CCl | Cl | CF₃ | H | H | OCH₂CO₂CH₃ | NO₂ |
| CCl | Cl | CF₃ | H | H | OCH₂CO₂C₅H₁₁ | NO₂ |
| CCl | Cl | CF₃ | H | H | OCH₃ | NO₂ |
| CCl | Cl | CF₃ | H | H | OC₂H₅ | NO₂ |
| CCl | Cl | CF₃ | H | H | OC₃H₇ | NO₂ |
| CCl | Cl | CF₃ | H | H | OC₄H₉ | NO₂ |
| CCl | Cl | CF₃ | H | H | OC₅H₁₁ | NO₂ |
| CCl | Cl | CF₃ | H | H | OCH₂CH=CH₂ | NO₂ |
| CCl | Cl | CF₃ | H | H | OCH₂C≡CH | NO₂ |
| CCl | Cl | CF₃ | H | H | OCH₂OCH₃ | NO₂ |
| CCl | Cl | CF₃ | H | H | O-cyclopentyl | NO₂ |

TABLE 1-continued

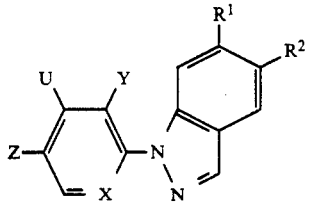

| X | Y | Z | U | V | R¹ | R² |
|---|---|---|---|---|---|---|
| CCl | Cl | CF₃ | H | H | 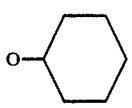 | NO₂ |
| CCl | Cl | CF₃ | H | H | OCOCH₃ | NO₂ |
| CCl | Cl | CF₃ | H | H | OCOC₄H₉ | NO₂ |
| CCl | Cl | CF₃ | H | H | OCO₂CH₃ | NO₂ |
| CCl | Cl | CF₃ | H | H | OCO₂C₂H₅ | NO₂ |
| CCl | Cl | CF₃ | H | H | OCO₂C₃H₇ | NO₂ |
| CCl | Cl | CF₃ | H | H | OCH(CH₃)CH₂OH | NO₂ |
| CCl | Cl | CF₃ | H | H | OCH₂CH₂OH | NO₂ |
| CCl | Cl | CF₃ | H | H | SCH₂CH=CH₂ | NO₂ |
| CCl | Cl | CF₃ | H | H | SCH₂C≡CH | NO₂ |
| CCl | Cl | CF₃ | H | H | SCH₂CO₂CH₃ | NO₂ |
| CCl | Cl | CF₃ | H | H | SCH₂CO₂C₅H₁₁ | NO₂ |
| CCl | Cl | CF₃ | H | H | NHCH(CH₃)CO₂CH₃ | NO₂ |
| CCl | Cl | CF₃ | H | H | NHCH(CH₃)CO₂C₂H₅ | NO₂ |
| CCl | Cl | CF₃ | H | H | NHCH(CH₃)CO₂C₃H₇ | NO₂ |
| CCl | Cl | CF₃ | H | H | NHCH(CH₃)CO₂C₄H₉ | NO₂ |
| CCl | Cl | CF₃ | H | H | NHCH(CH₃)CO₂C₅H₁₁ | NO₂ |
| CCl | Cl | CF₃ | H | H | NHCH(CH₃)CO₂H | NO₂ |
| CCl | Cl | CF₃ | H | H | NHCH(CH₃)CO₂CH₂CH=CH₂ | NO₂ |
| CCl | Cl | CF₃ | H | H | NHCH(CH₃)CO₂CH₂C≡CH | NO₂ |
| CCl | Cl | CF₃ | H | H | 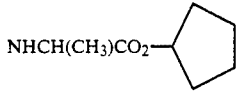 | NO₂ |
| CCl | Cl | CF₃ | H | H | 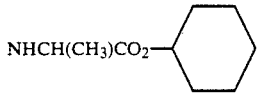 | NO₂ |
| CCl | Cl | CF₃ | H | H | NHCH₃ | NO₂ |
| CCl | Cl | CF₃ | H | H | NHC₂H₅ | NO₂ |
| CCl | Cl | CF₃ | H | H | NHC₃H₇ | NO₂ |
| CCl | Cl | CF₃ | H | H | NHC₄H₉ | NO₂ |
| CCl | Cl | CF₃ | H | H | NHC₅H₁₁ | NO₂ |
| CCl | Cl | CF₃ | H | H | NHCH₂CH=CH₂ | NO₂ |
| CCl | Cl | CF₃ | H | H | NHCH₂C≡CH | NO₂ |
| CCl | Cl | CF₃ | H | H | NHCH₂OCH₃ | NO₂ |
| CCl | Cl | CF₃ | H | H | NHCH₂CH₂F | NO₂ |
| CCl | Cl | CF₃ | H | H | 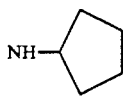 | NO₂ |
| CCl | Cl | CF₃ | H | H | 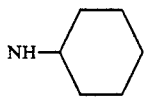 | NO₂ |
| CCl | Cl | CF₃ | H | H | NHCH(OCH₃)CO₂CH₃ | NO₂ |
| CCl | Cl | CF₃ | H | H | NHCH(OCH₃)CO₂C₅H₁₁ | NO₂ |
| CCl | Cl | CF₃ | H | H | NHCH₂CO₂H | NO₂ |
| CCl | Cl | CF₃ | H | H | NHCH₂CO₂CH₃ | NO₂ |
| CCl | Cl | CF₃ | H | H | NHCH₂CO₂C₂H₅ | NO₂ |
| CCl | Cl | CF₃ | H | H | NHCH₂CO₂C₃H₇ | NO₂ |
| CCl | Cl | CF₃ | H | H | NHCH₂CO₂C₄H₉ | NO₂ |
| CCl | Cl | CF₃ | H | H | NHSO₂CH₃ | NO₂ |
| CCl | Cl | CF₃ | H | H | NHSO₂C₂H₅ | NO₂ |
| CCl | Cl | CF₃ | H | H | NHSO₂C₃H₇ | NO₂ |

TABLE 1-continued

| X | Y | Z | U | V | R¹ | R² |
|---|---|---|---|---|---|---|
| CCl | Cl | CF₃ | H | H | NHSO₂C₄H₉ | NO₂ |
| CCl | Cl | CF₃ | H | H | NHSO₂CH₂Cl | NO₂ |
| CCl | Cl | CF₃ | H | H | NHSO₂CH₂CH₂Cl | NO₂ |
| CCl | Cl | CF₃ | H | H | NHSO₂CH₂CH₂CH₂Cl | NO₂ |
| CCl | Cl | CF₃ | H | H | NCH(CH₃)CO₂C₂H₅ / SO₂CH₃ | NO₂ |
| CCl | Cl | CF₃ | H | H | NCH₂CH=CH₂ / SO₂CH₃ | NO₂ |
| CCl | Cl | CF₃ | H | H | NCH₂C≡CH / SO₂CH₃ | NO₂ |
| CCl | Cl | CF₃ | H | H | NCH(OCH₃)CO₂CH₃ / SO₂CH₃ | NO₂ |
| CCl | Cl | CF₃ | H | H | N(SO₂CH₃)₂ | NO₂ |
| CCl | Cl | CF₃ | H | H | CO₂H | NO₂ |
| CCl | Cl | CF₃ | H | H | CO₂CH₃ | NO₂ |
| CCl | Cl | CF₃ | H | H | CO₂C₂H₅ | NO₂ |
| CCl | Cl | CF₃ | H | H | CO₂C₃H₇ | NO₂ |
| CCl | Cl | CF₃ | H | H | CO₂C₄H₉ | NO₂ |
| CCl | Cl | CF₃ | H | H | CO₂C₅H₁₁ | NO₂ |
| CCl | Cl | CF₃ | H | H | CO₂CH₂CH=CH₂ | NO₂ |
| CCl | Cl | CF₃ | H | H | CO₂CH₂C≡CH | NO₂ |
| CCl | Cl | CF₃ | H | H | CO₂CH₂OCH₃ | NO₂ |
| CCl | Cl | CF₃ | H | H | CO₂-cyclopentyl | NO₂ |
| CCl | Cl | CF₃ | H | H | CO₂-cyclohexyl | NO₂ |
| CCl | Cl | CF₃ | H | H | CO₂CH₂CH₂F | NO₂ |
| CCl | Cl | CF₃ | H | H | CHO | NO₂ |
| CCl | Cl | CF₃ | H | H | COCH₃ | NO₂ |
| CCl | Cl | CF₃ | H | H | COCH₂OCH₃ | NO₂ |
| CCl | Cl | CF₃ | H | H | CH₂OH | NO₂ |
| CCl | Cl | CF₃ | H | H | CH(OH)CH₃ | NO₂ |
| CCl | Cl | CF₃ | H | H | Cl | CN |
| CCl | Cl | CF₃ | H | H | OCH₃ | CN |
| CCl | Cl | CF₃ | H | H | OC₂H₅ | CN |
| CCl | Cl | CF₃ | H | H | OC₃H₇ | CN |
| CCl | Cl | CF₃ | H | H | OCH₃ | Cl |
| CCl | Cl | CF₃ | H | H | OC₂H₅ | Cl |
| CCl | Cl | CF₃ | H | H | OC₃H₇ | Cl |
| CCl | Cl | CF₃ | H | H | OCH₃ | Br |
| CCl | Cl | CF₃ | H | H | OCH₃ | F |
| CCl | Cl | CF₃ | H | H | OCH₂CH=CH₂ | CN |
| CCl | Cl | CF₃ | H | H | OCH₂CH=CH₂ | Cl |
| CCl | Cl | CF₃ | H | H | OCH₂CH=CH₂ | Br |
| CCl | Cl | CF₃ | H | H | OCH₂CH=CH₂ | F |
| CCl | Cl | CF₃ | H | H | OCH₂C≡CH | CN |
| CCl | Cl | CF₃ | H | H | OCH₂C≡CH | Cl |
| CCl | Cl | CF₃ | H | H | OCH₂C≡CH | Br |
| CCl | Cl | CF₃ | H | H | OCH₂C≡CH | F |
| CCl | Cl | CF₃ | H | H | OCH(CH₃)CO₂C₂H₅ | CN |
| CCl | Cl | CF₃ | H | H | OCH(CH₃)CO₂C₂H₅ | Cl |

TABLE 1-continued

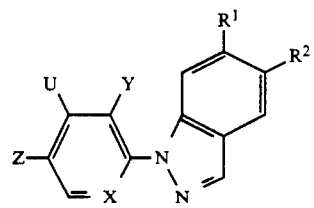

| X | Y | Z | U | V | R¹ | R² |
|---|---|---|---|---|----|----|
| CCl | Cl | CF$_3$ | H | H | OCH(CH$_3$)CO$_2$C$_2$H$_5$ | Br |
| CCl | Cl | CF$_3$ | H | H | OCH(CH$_3$)CO$_2$C$_2$H$_5$ | F |
| CCl | Cl | CF$_3$ | H | H | NHCH$_2$CH=CH$_2$ | CN |
| CCl | Cl | CF$_3$ | H | H | NHCH$_2$C≡CH | Br |
| CCl | Cl | CF$_3$ | H | H | NHCH$_2$C≡CH | Cl |
| CCl | Cl | CF$_3$ | H | H | NHCH$_2$C≡CH | F |
| CCl | Cl | CF$_3$ | H | H | NHCH(CH$_3$)CO$_2$CH$_3$ | CN |
| CCl | Cl | CF$_3$ | H | H | NHCH(CH$_3$)CO$_2$CH$_3$ | Cl |
| CCl | Cl | CF$_3$ | H | H | NHCH(CH$_3$)CO$_2$CH$_3$ | Br |
| CCl | Cl | CF$_3$ | H | H | NHCH(CH$_3$)CO$_2$CH$_3$ | F |
| CCl | Cl | CF$_3$ | H | H | NHSO$_2$CH$_3$ | CN |
| CCl | Cl | CF$_3$ | H | H | NHSO$_2$CH$_3$ | Cl |
| CCl | Cl | CF$_3$ | H | H | NHSO$_2$CH$_3$ | Br |
| CCl | Cl | CF$_3$ | H | H | NHSO$_2$CH$_3$ | F |
| CCl | Cl | CF$_3$ | H | H | SCH(CH$_3$)CO$_2$C$_2$H$_5$ | CN |
| CCl | Cl | CF$_3$ | H | H | SCH(CH$_3$)CO$_2$C$_2$H$_5$ | Cl |
| CCl | Cl | CF$_3$ | H | H | SCH(CH$_3$)CO$_2$C$_2$H$_5$ | Br |
| CCl | Cl | CF$_3$ | H | H | SCH(CH$_3$)CO$_2$C$_2$H$_5$ | F |
| CCl | Cl | CF$_3$ | H | H | CO$_2$C$_2$H$_5$ | CN |
| CCl | Cl | CF$_3$ | H | H | CO$_2$C$_2$H$_5$ | Br |
| CCl | Cl | CF$_3$ | H | H | CO$_2$C$_2$H$_5$ | Cl |
| CCl | Cl | CF$_3$ | H | H | CO$_2$C$_2$H$_5$ | F |
| CCl | Cl | CF$_3$ | H | H | NO$_2$ | NO$_2$ |
| CCl | Cl | CF$_3$ | H | H | CN | NO$_2$ |
| CCl | F | CF$_3$ | H | H | OCH(CH$_3$)CO$_2$CH$_3$ | H |
| CCl | F | CF$_3$ | H | H | OCH(CH$_3$)CO$_2$C$_2$H$_5$ | H |
| CCl | F | CF$_3$ | H | H | OCH(CH$_3$)CO$_2$C$_3$H$_7$ | H |
| CCl | F | CF$_3$ | H | H | OCH(CH$_3$)CO$_2$C$_4$H$_9$ | H |
| CCl | F | CF$_3$ | H | H | OCH(CH$_3$)CO$_2$C$_5$H$_{11}$ | H |
| CCl | F | CF$_3$ | H | H | OCH(CH$_3$)CO$_2$H | H |
| CCl | F | CF$_3$ | H | H | OCH(CH$_3$)CO$_2$K | H |
| CCl | F | CF$_3$ | H | H | OCH(CH$_3$)CO$_2$Na | H |
| CCl | F | CF$_3$ | H | H | OCH(CH$_3$)CO$_2$NH$_4$ | H |
| CCl | F | CF$_3$ | H | H | OCH(CH$_3$)CO$_2$CH$_2$CH=CH$_2$ | H |
| CCl | F | CF$_3$ | H | H | OCH(CH$_3$)CO$_2$CH$_2$C≡CH | H |
| CCl | F | CF$_3$ | H | H | OCH(CH$_3$)CO$_2$CH$_2$OCH$_3$ | H |
| CCl | F | CF$_3$ | H | H | OCH(CH$_3$)CO$_2$-cyclopentyl | H |
| CCl | F | CF$_3$ | H | H | OCH(CH$_3$)CO$_2$-cyclohexyl | H |
| CCl | F | CF$_3$ | H | H | OCH(CH$_3$)CO$_2$CH$_2$F | H |
| CCl | F | CF$_3$ | H | H | SCH(CH$_3$)CO$_2$CH$_3$ | H |
| CCl | F | CF$_3$ | H | H | SCH(CH$_3$)CO$_2$C$_5$H$_{11}$ | H |
| CCl | F | CF$_3$ | H | H | SCH(CH$_3$)CO$_2$H | H |
| CCl | F | CF$_3$ | H | H | OCH$_2$CO$_2$H | H |
| CCl | F | CF$_3$ | H | H | OCH$_2$CO$_2$CH$_3$ | H |
| CCl | F | CF$_3$ | H | H | OCH$_2$CO$_2$C$_5$H$_{11}$ | H |
| CCl | F | CF$_3$ | H | H | OCH$_3$ | H |
| CCl | F | CF$_3$ | H | H | OC$_2$H$_5$ | H |
| CCl | F | CF$_3$ | H | H | OC$_3$H$_7$ | H |
| CCl | F | CF$_3$ | H | H | OC$_4$H$_9$ | H |
| CCl | F | CF$_3$ | H | H | OC$_5$H$_{11}$ | H |
| CCl | F | CF$_3$ | H | H | OCH$_2$CH=CH$_2$ | H |
| CCl | F | CF$_3$ | H | H | OCH$_2$C≡CH | H |
| CCl | F | CF$_3$ | H | H | OCH$_2$OCH$_3$ | H |
| CCl | F | CF$_3$ | H | H | O-cyclopentyl | H |

TABLE 1-continued

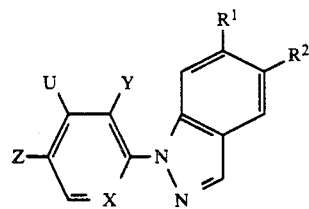

| X | Y | Z | U | V | R¹ | R² |
|---|---|---|---|---|---|---|
| CCl | F | CF$_3$ | H | H | O-cyclohexyl | H |
| CCl | F | CF$_3$ | H | H | OCOCH$_3$ | H |
| CCl | F | CF$_3$ | H | H | OCOC$_4$H$_9$ | H |
| CCl | F | CF$_3$ | H | H | OCO$_2$CH$_3$ | H |
| CCl | F | CF$_3$ | H | H | OCO$_2$C$_2$H$_5$ | H |
| CCl | F | CF$_3$ | H | H | OCO$_2$C$_3$H$_7$ | H |
| CCl | F | CF$_3$ | H | H | OCH(CH$_3$)CH$_2$OH | H |
| CCl | F | CF$_3$ | H | H | OCH$_2$CH$_2$OH | H |
| CCl | F | CF$_3$ | H | H | SCH$_2$CH=CH$_2$ | H |
| CCl | F | CF$_3$ | H | H | SCH$_2$C≡CH | H |
| CCl | F | CF$_3$ | H | H | SCH$_2$CO$_2$CH$_3$ | H |
| CCl | F | CF$_3$ | H | H | SCH$_2$CO$_2$C$_5$H$_{11}$ | H |
| CCl | F | CF$_3$ | H | H | NHCH(CH$_3$)CO$_2$CH$_3$ | H |
| CCl | F | CF$_3$ | H | H | NHCH(CH$_3$)CO$_2$C$_2$H$_5$ | H |
| CCl | F | CF$_3$ | H | H | NHCH(CH$_3$)CO$_2$C$_3$H$_7$ | H |
| CCl | F | CF$_3$ | H | H | NHCH(CH$_3$)CO$_2$C$_4$H$_9$ | H |
| CCl | F | CF$_3$ | H | H | NHCH(CH$_3$)CO$_2$C$_5$H$_{11}$ | H |
| CCl | F | CF$_3$ | H | H | NHCH(CH$_3$)CO$_2$H | H |
| CCl | F | CF$_3$ | H | H | NHCH(CH$_3$)CO$_2$CH$_2$CH=CH$_2$ | H |
| CCl | F | CF$_3$ | H | H | NHCH(CH$_3$)CO$_2$CH$_2$C≡CH | H |
| CCl | F | CF$_3$ | H | H | NHCH(CH$_3$)CO$_2$-cyclopentyl | H |
| CCl | F | CF$_3$ | H | H | NHCH(CH$_3$)CO$_2$-cyclohexyl | H |
| CCl | F | CF$_3$ | H | H | NHCH$_3$ | H |
| CCl | F | CF$_3$ | H | H | NHC$_2$H$_5$ | H |
| CCl | F | CF$_3$ | H | H | NHC$_3$H$_7$ | H |
| CCl | F | CF$_3$ | H | H | NHC$_4$H$_9$ | H |
| CCl | F | CF$_3$ | H | H | NHC$_5$H$_{11}$ | H |
| CCl | F | CF$_3$ | H | H | NHCH$_2$CH=CH$_2$ | H |
| CCl | F | CF$_3$ | H | H | NHCH$_2$C≡CH | H |
| CCl | F | CF$_3$ | H | H | NHCH$_2$OCH$_3$ | H |
| CCl | F | CF$_3$ | H | H | NHCH$_2$CH$_2$F | H |
| CCl | F | CF$_3$ | H | H | NH-cyclopentyl | H |
| CCl | F | CF$_3$ | H | H | NH-cyclohexyl | H |
| CCl | F | CF$_3$ | H | H | NHCH(OCH$_3$)CO$_2$CH$_3$ | H |
| CCl | F | CF$_3$ | H | H | NHCH(OCH$_3$)CO$_2$C$_5$H$_{11}$ | H |
| CCl | F | CF$_3$ | H | H | NHCH$_2$CO$_2$H | H |
| CCl | F | CF$_3$ | H | H | NHCH$_2$CO$_2$CH$_3$ | H |
| CCl | F | CF$_3$ | H | H | NHCH$_2$CO$_2$C$_2$H$_5$ | H |
| CCl | F | CF$_3$ | H | H | NHCH$_2$CO$_2$C$_3$H$_7$ | H |
| CCl | F | CF$_3$ | H | H | NHCH$_2$CO$_2$C$_4$H$_9$ | H |
| CCl | F | CF$_3$ | H | H | NHSO$_2$CH$_3$ | H |
| CCl | F | CF$_3$ | H | H | NHSO$_2$C$_2$H$_5$ | H |

TABLE 1-continued

[Structure: indazole with substituents R¹, R², and pyridine-like ring with U, Y, Z, X, V]

| X | Y | Z | U | V | R¹ | R² |
|---|---|---|---|---|---|---|
| CCl | F | CF₃ | H | H | NHSO₂C₃H₇ | H |
| CCl | F | CF₃ | H | H | NHSO₂C₄H₉ | H |
| CCl | F | CF₃ | H | H | NHSO₂CH₂Cl | H |
| CCl | F | CF₃ | H | H | NHSO₂CH₂CH₂Cl | H |
| CCl | F | CF₃ | H | H | NHSO₂CH₂CH₂CH₂Cl | H |
| CCl | F | CF₃ | H | H | NCH(CH₃)CO₂C₂H₅ \| SO₂CH₃ | H |
| CCl | F | CF₃ | H | H | NCH₂CH=CH₂ \| SO₂CH₃ | H |
| CCl | F | CF₃ | H | H | NCH₂C≡CH \| SO₂CH₃ | H |
| CCl | F | CF₃ | H | H | NCH(OCH₃)CO₂CH₃ \| SO₂CH₃ | H |
| CCl | F | CF₃ | H | H | N(SO₂CH₃)₂ | H |
| CCl | F | CF₃ | H | H | CO₂H | H |
| CCl | F | CF₃ | H | H | CO₂CH₃ | H |
| CCl | F | CF₃ | H | H | CO₂C₂H₅ | H |
| CCl | F | CF₃ | H | H | CO₂C₃H₇ | H |
| CCl | F | CF₃ | H | H | CO₂C₄H₉ | H |
| CCl | F | CF₃ | H | H | CO₂C₅H₁₁ | H |
| CCl | F | CF₃ | H | H | CO₂CH₂CH=CH₂ | H |
| CCl | F | CF₃ | H | H | CO₂CH₂C≡CH | H |
| CCl | F | CF₃ | H | H | CO₂CH₂OCH₃ | H |
| CCl | F | CF₃ | H | H | CO₂-cyclopentyl | H |
| CCl | F | CF₃ | H | H | CO₂-cyclohexyl | H |
| CCl | F | CF₃ | H | H | CO₂CH₂CH₂F | H |
| CCl | F | CF₃ | H | H | CHO | H |
| CCl | F | CF₃ | H | H | COCH₃ | H |
| CCl | F | CF₃ | H | H | COCH₂OCH₃ | H |
| CCl | F | CF₃ | H | H | CH₂OH | H |
| CCl | F | CF₃ | H | H | CH(OH)CH₃ | H |
| CCl | F | CF₃ | H | H | OCH(CH₃)CO₂CH₃ | NO₂ |
| CCl | F | CF₃ | H | H | OCH(CH₃)CO₂C₂H₅ | NO₂ |
| CCl | F | CF₃ | H | H | OCH(CH₃)CO₂C₃H₇ | NO₂ |
| CCl | F | CF₃ | H | H | OCH(CH₃)CO₂C₄H₉ | NO₂ |
| CCl | F | CF₃ | H | H | OCH(CH₃)CO₂C₅H₁₁ | NO₂ |
| CCl | F | CF₃ | H | H | OCH(CH₃)CO₂H | NO₂ |
| CCl | F | CF₃ | H | H | OCH(CH₃)CO₂K | NO₂ |
| CCl | F | CF₃ | H | H | OCH(CH₃)CO₂Na | NO₂ |
| CCl | F | CF₃ | H | H | OCH(CH₃)CO₂NH₄ | NO₂ |
| CCl | F | CF₃ | H | H | OCH(CH₃)CO₂CH₂CH=CH₂ | NO₂ |
| CCl | F | CF₃ | H | H | OCH(CH₃)CO₂CH₂C≡CH | NO₂ |
| CCl | F | CF₃ | H | H | OCH(CH₃)CO₂CH₂OCH₃ | NO₂ |
| CCl | F | CF₃ | H | H | OCH(CH₃)CO₂-cyclopentyl | NO₂ |

TABLE 1-continued

| X | Y | Z | U | V | R¹ | R² |
|---|---|---|---|---|---|---|
| CCl | F | CF₃ | H | H | OCH(CH₃)CO₂-cyclohexyl | NO₂ |
| CCl | F | CF₃ | H | H | OCH(CH₃)CO₂CH₂F | NO₂ |
| CCl | F | CF₃ | H | H | SCH(CH₃)CO₂CH₃ | NO₂ |
| CCl | F | CF₃ | H | H | SCH(CH₃)CO₂C₅H₁₁ | NO₂ |
| CCl | F | CF₃ | H | H | SCH(CH₃)CO₂H | NO₂ |
| CCl | F | CF₃ | H | H | OCH₂CO₂H | NO₂ |
| CCl | F | CF₃ | H | H | OCH₂CO₂CH₃ | NO₂ |
| CCl | F | CF₃ | H | H | OCH₂CO₂C₅H₁₁ | NO₂ |
| CCl | F | CF₃ | H | H | OCH₃ | NO₂ |
| CCl | F | CF₃ | H | H | OC₂H₅ | NO₂ |
| CCl | F | CF₃ | H | H | OC₃H₇ | NO₂ |
| CCl | F | CF₃ | H | H | OC₄H₉ | NO₂ |
| CCl | F | CF₃ | H | H | OC₅H₁₁ | NO₂ |
| CCl | F | CF₃ | H | H | OCH₂CH=CH₂ | NO₂ |
| CCl | F | CF₃ | H | H | OCH₂C≡CH | NO₂ |
| CCl | F | CF₃ | H | H | OCH₂OCH₃ | NO₂ |
| CCl | F | CF₃ | H | H | O-cyclopentyl | NO₂ |
| CCl | F | CF₃ | H | H | O-cyclohexyl | NO₂ |
| CCl | F | CF₃ | H | H | OCOCH₃ | NO₂ |
| CCl | F | CF₃ | H | H | OCOC₄H₉ | NO₂ |
| CCl | F | CF₃ | H | H | OCO₂CH₃ | NO₂ |
| CCl | F | CF₃ | H | H | OCO₂C₂H₅ | NO₂ |
| CCl | F | CF₃ | H | H | OCO₂C₃H₇ | NO₂ |
| CCl | F | CF₃ | H | H | OCH(CH₃)CH₂OH | NO₂ |
| CCl | F | CF₃ | H | H | OCH₂CH₂OH | NO₂ |
| CCl | F | CF₃ | H | H | SCH₂CH=CH₂ | NO₂ |
| CCl | F | CF₃ | H | H | SCH₂C≡CH | NO₂ |
| CCl | F | CF₃ | H | H | SCH₂CO₂CH₃ | NO₂ |
| CCl | F | CF₃ | H | H | SCH₂CO₂C₅H₁₁ | NO₂ |
| CCl | F | CF₃ | H | H | NHCH(CH₃)CO₂CH₃ | NO₂ |
| CCl | F | CF₃ | H | H | NHCH(CH₃)CO₂C₂H₅ | NO₂ |
| CCl | F | CF₃ | H | H | NHCH(CH₃)CO₂C₃H₇ | NO₂ |
| CCl | F | CF₃ | H | H | NHCH(CH₃)CO₂C₄H₉ | NO₂ |
| CCl | F | CF₃ | H | H | NHCH(CH₃)CO₂C₅H₁₁ | NO₂ |
| CCl | F | CF₃ | H | H | NHCH(CH₃)CO₂H | NO₂ |
| CCl | F | CF₃ | H | H | NHCH(CH₃)CO₂CH₂CH=CH₂ | NO₂ |
| CCl | F | CF₃ | H | H | NHCH(CH₃)CO₂CH₂C≡CH | NO₂ |
| CCl | F | CF₃ | H | H | NHCH(CH₃)CO₂-cyclopentyl | NO₂ |
| CCl | F | CF₃ | H | H | NHCH(CH₃)CO₂-cyclohexyl | NO₂ |
| CCl | F | CF₃ | H | H | NHCH₃ | NO₂ |
| CCl | F | CF₃ | H | H | NHC₂H₅ | NO₂ |
| CCl | F | CF₃ | H | H | NHC₃H₇ | NO₂ |

TABLE 1-continued

[Structure: pyrazole fused to benzene ring with R¹, R² substituents, connected via N to pyridine-like ring with substituents X, Y, Z, U, V]

| X | Y | Z | U | V | R¹ | R² |
|---|---|---|---|---|-----|-----|
| CCl | F | CF$_3$ | H | H | NHC$_4$H$_9$ | NO$_2$ |
| CCl | F | CF$_3$ | H | H | NHC$_5$H$_{11}$ | NO$_2$ |
| CCl | F | CF$_3$ | H | H | NHCH$_2$CH=CH$_2$ | NO$_2$ |
| CCl | F | CF$_3$ | H | H | NHCH$_2$C≡CH | NO$_2$ |
| CCl | F | CF$_3$ | H | H | NHCH$_2$OCH$_3$ | NO$_2$ |
| CCl | F | CF$_3$ | H | H | NHCH$_2$CH$_2$F | NO$_2$ |
| CCl | F | CF$_3$ | H | H | NH-cyclopentyl | NO$_2$ |
| CCl | F | CF$_3$ | H | H | NH-cyclohexyl | NO$_2$ |
| CCl | F | CF$_3$ | H | H | NHCH(OCH$_3$)CO$_2$CH$_3$ | NO$_2$ |
| CCl | F | CF$_3$ | H | H | NHCH(OCH$_3$)CO$_2$C$_5$H$_{11}$ | NO$_2$ |
| CCl | F | CF$_3$ | H | H | NHCH$_2$CO$_2$H | NO$_2$ |
| CCl | F | CF$_3$ | H | H | NHCH$_2$CO$_2$CH$_3$ | NO$_2$ |
| CCl | F | CF$_3$ | H | H | NHCH$_2$CO$_2$C$_2$H$_5$ | NO$_2$ |
| CCl | F | CF$_3$ | H | H | NHCH$_2$CO$_2$C$_3$H$_7$ | NO$_2$ |
| CCl | F | CF$_3$ | H | H | NHCH$_2$CO$_2$C$_4$H$_9$ | NO$_2$ |
| CCl | F | CF$_3$ | H | H | NHSO$_2$CH$_3$ | NO$_2$ |
| CCl | F | CF$_3$ | H | H | NHSO$_2$C$_2$H$_5$ | NO$_2$ |
| CCl | F | CF$_3$ | H | H | NHSO$_2$C$_3$H$_7$ | NO$_2$ |
| CCl | F | CF$_3$ | H | H | NHSO$_2$C$_4$H$_9$ | NO$_2$ |
| CCl | F | CF$_3$ | H | H | NHSO$_2$CH$_2$Cl | NO$_2$ |
| CCl | F | CF$_3$ | H | H | NHSO$_2$CH$_2$CH$_2$Cl | NO$_2$ |
| CCl | F | CF$_3$ | H | H | NHSO$_2$CH$_2$CH$_2$CH$_2$Cl | NO$_2$ |
| CCl | F | CF$_3$ | H | H | N(CH(CH$_3$)CO$_2$C$_2$H$_5$)(SO$_2$CH$_3$) | NO$_2$ |
| CCl | F | CF$_3$ | H | H | N(CH$_2$CH=CH$_2$)(SO$_2$CH$_3$) | NO$_2$ |
| CCl | F | CF$_3$ | H | H | N(CH$_2$C≡CH)(SO$_2$CH$_3$) | NO$_2$ |
| CCl | F | CF$_3$ | H | H | N(CH(OCH$_3$)CO$_2$CH$_3$)(SO$_2$CH$_3$) | NO$_2$ |
| CCl | F | CF$_3$ | H | H | N(SO$_2$CH$_3$)$_2$ | NO$_2$ |
| CCl | F | CF$_3$ | H | H | CO$_2$H | NO$_2$ |
| CCl | F | CF$_3$ | H | H | CO$_2$CH$_3$ | NO$_2$ |
| CCl | F | CF$_3$ | H | H | CO$_2$C$_2$H$_5$ | NO$_2$ |
| CCl | F | CF$_3$ | H | H | CO$_2$C$_3$H$_7$ | NO$_2$ |
| CCl | F | CF$_3$ | H | H | CO$_2$C$_4$H$_9$ | NO$_2$ |
| CCl | F | CF$_3$ | H | H | CO$_2$C$_5$H$_{11}$ | NO$_2$ |
| CCl | F | CF$_3$ | H | H | CO$_2$CH$_2$CH=CH$_2$ | NO$_2$ |
| CCl | F | CF$_3$ | H | H | CO$_2$CH$_2$C≡CH | NO$_2$ |
| CCl | F | CF$_3$ | H | H | CO$_2$CH$_2$OCH$_3$ | NO$_2$ |
| CCl | F | CF$_3$ | H | H | CO$_2$-cyclopentyl | NO$_2$ |

TABLE 1-continued

| X | Y | Z | U | V | R¹ | R² |
|---|---|---|---|---|---|---|
| CCl | F | CF₃ | H | H | (cyclohexyl-O-CO-) CO₂-cyclohexyl | NO₂ |
| CCl | F | CF₃ | H | H | CO₂CH₂CH₂F | NO₂ |
| CCl | F | CF₃ | H | H | CHO | NO₂ |
| CCl | F | CF₃ | H | H | COCH₃ | NO₂ |
| CCl | F | CF₃ | H | H | COCH₂OCH₃ | NO₂ |
| CCl | F | CF₃ | H | H | CH₂OH | NO₂ |
| CCl | F | CF₃ | H | H | CH(OH)CH₃ | NO₂ |
| CCl | F | CF₃ | H | H | Cl | NO₂ |
| CCl | F | CF₃ | H | H | OCH₃ | CN |
| CCl | F | CF₃ | H | H | OC₂H₅ | CN |
| CCl | F | CF₃ | H | H | OC₃H₇ | CN |
| CCl | F | CF₃ | H | H | OCH₃ | Cl |
| CCl | F | CF₃ | H | H | OC₂H₅ | Cl |
| CCl | F | CF₃ | H | H | OC₃H₇ | Cl |
| CCl | F | CF₃ | H | H | OCH₃ | Br |
| CCl | F | CF₃ | H | H | OCH₃ | F |
| CCl | F | CF₃ | H | H | OCH₂CH=CH₂ | CN |
| CCl | F | CF₃ | H | H | OCH₂CH=CH₂ | Cl |
| CCl | F | CF₃ | H | H | OCH₂CH=CH₂ | Br |
| CCl | F | CF₃ | H | H | OCH₂CH=CH₂ | F |
| CCl | F | CF₃ | H | H | OCH₂C≡CH | CN |
| CCl | F | CF₃ | H | H | OCH₂C≡CH | Cl |
| CCl | F | CF₃ | H | H | OCH₂C≡CH | Br |
| CCl | F | CF₃ | H | H | OCH₂C≡CH | F |
| CCl | F | CF₃ | H | H | OCH(CH₃)CO₂C₂H₅ | CN |
| CCl | F | CF₃ | H | H | OCH(CH₃)CO₂C₂H₅ | Cl |
| CCl | F | CF₃ | H | H | OCH(CH₃)CO₂C₂H₅ | Br |
| CCl | F | CF₃ | H | H | OCH(CH₃)CO₂C₂H₅ | F |
| CCl | F | CF₃ | H | H | NHCH₂CH=CH₂ | CN |
| CCl | F | CF₃ | H | H | NHCH₂C≡CH | Br |
| CCl | F | CF₃ | H | H | NHCH₂C≡CH | Cl |
| CCl | F | CF₃ | H | H | NHCH₂C≡CH | F |
| CCl | F | CF₃ | H | H | NHCH(CH₃)CO₂CH₃ | CN |
| CCl | F | CF₃ | H | H | NHCH(CH₃)CO₂CH₃ | Cl |
| CCl | F | CF₃ | H | H | NHCH(CH₃)CO₂CH₃ | Br |
| CCl | F | CF₃ | H | H | NHCH(CH₃)CO₂CH₃ | F |
| CCl | F | CF₃ | H | H | NHSO₂CH₃ | CN |
| CCl | F | CF₃ | H | H | NHSO₂CH₃ | Cl |
| CCl | F | CF₃ | H | H | NHSO₂CH₃ | Br |
| CCl | F | CF₃ | H | H | NHSO₂CH₃ | F |
| CCl | F | CF₃ | H | H | SCH(CH₃)CO₂C₂H₅ | CN |
| CCl | F | CF₃ | H | H | SCH(CH₃)CO₂C₂H₅ | Cl |
| CCl | F | CF₃ | H | H | SCH(CH₃)CO₂C₂H₅ | Br |
| CCl | F | CF₃ | H | H | SCH(CH₃)CO₂C₂H₅ | F |
| CCl | F | CF₃ | H | H | CO₂C₂H₅ | CN |
| CCl | F | CF₃ | H | H | CO₂C₂H₅ | Br |
| CCl | F | CF₃ | H | H | CO₂C₂H₅ | Cl |
| CCl | F | CF₃ | H | H | CO₂C₂H₅ | F |
| CCl | F | CF₃ | H | H | NO₂ | NO₂ |
| CCl | F | CF₃ | H | H | CN | NO₂ |
| CF | F | CF₃ | H | H | OCH(CH₃)CO₂CH₃ | H |
| CF | F | CF₃ | H | H | OCH(CH₃)CO₂C₂H₅ | H |
| CF | F | CF₃ | H | H | OCH(CH₃)CO₂C₃H₇ | H |
| CF | F | CF₃ | H | H | OCH(CH₃)CO₂C₄H₉ | H |
| CF | F | CF₃ | H | H | OCH(CH₃)CO₂C₅H₁₁ | H |
| CF | F | CF₃ | H | H | OCH(CH₃)CO₂H | H |
| CF | F | CF₃ | H | H | OCH(CH₃)CO₂K | H |
| CF | F | CF₃ | H | H | OCH(CH₃)CO₂Na | H |
| CF | F | CF₃ | H | H | OCH(CH₃)CO₂NH₄ | H |
| CF | F | CF₃ | H | H | OCH(CH₃)CO₂CH₂CH=CH₂ | H |
| CF | F | CF₃ | H | H | OCH(CH₃)CO₂CH₂C≡CH | H |
| CF | F | CF₃ | H | H | OCH(CH₃)CO₂CH₂OCH₃ | H |

TABLE 1-continued

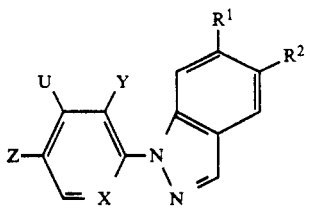

| X | Y | Z | U | V | R¹ | R² |
|---|---|---|---|---|---|---|
| CF | F | CF$_3$ | H | H | OCH(CH$_3$)CO$_2$—  | H |
| CF | F | CF$_3$ | H | H | OCH(CH$_3$)CO$_2$—  | H |
| CF | F | CF$_3$ | H | H | OCH(CH$_3$)CO$_2$CH$_2$F | H |
| CF | F | CF$_3$ | H | H | SCH(CH$_3$)CO$_2$CH$_3$ | H |
| CF | F | CF$_3$ | H | H | SCH(CH$_3$)CO$_2$C$_5$H$_{11}$ | H |
| CF | F | CF$_3$ | H | H | SCH(CH$_3$)CO$_2$H | H |
| CF | F | CF$_3$ | H | H | OCH$_2$CO$_2$H | H |
| CF | F | CF$_3$ | H | H | OCH$_2$CO$_2$CH$_3$ | H |
| CF | F | CF$_3$ | H | H | OCH$_2$CO$_2$C$_5$H$_{11}$ | H |
| CF | F | CF$_3$ | H | H | OCH$_3$ | H |
| CF | F | CF$_3$ | H | H | OC$_2$H$_5$ | H |
| CF | F | CF$_3$ | H | H | OC$_3$H$_7$ | H |
| CF | F | CF$_3$ | H | H | OC$_4$H$_9$ | H |
| CF | F | CF$_3$ | H | H | OC$_5$H$_{11}$ | H |
| CF | F | CF$_3$ | H | H | OCH$_2$CH=CH$_2$ | H |
| CF | F | CF$_3$ | H | H | OCH$_2$C≡CH | H |
| CF | F | CF$_3$ | H | H | OCH$_2$OCH$_3$ | H |
| CF | F | CF$_3$ | H | H | 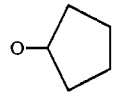 | H |
| CF | F | CF$_3$ | H | H | 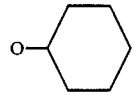 | H |
| CF | F | CF$_3$ | H | H | OCOCH$_3$ | H |
| CF | F | CF$_3$ | H | H | OCOC$_4$H$_9$ | H |
| CF | F | CF$_3$ | H | H | OCO$_2$CH$_3$ | H |
| CF | F | CF$_3$ | H | H | OCO$_2$C$_2$H$_5$ | H |
| CF | F | CF$_3$ | H | H | OCO$_2$C$_3$H$_7$ | H |
| CF | F | CF$_3$ | H | H | OCH(CH$_3$)CH$_2$OH | H |
| CF | F | CF$_3$ | H | H | OCH$_2$CH$_2$OH | H |
| CF | F | CF$_3$ | H | H | SCH$_2$CH=CH$_2$ | H |
| CF | F | CF$_3$ | H | H | SCH$_2$C≡CH | H |
| CF | F | CF$_3$ | H | H | SCH$_2$CO$_2$CH$_3$ | H |
| CF | F | CF$_3$ | H | H | SCH$_2$CO$_2$C$_5$H$_{11}$ | H |
| CF | F | CF$_3$ | H | H | NHCH(CH$_3$)CO$_2$CH$_3$ | H |
| CF | F | CF$_3$ | H | H | NHCH(CH$_3$)CO$_2$C$_2$H$_5$ | H |
| CF | F | CF$_3$ | H | H | NHCH(CH$_3$)CO$_2$C$_3$H$_7$ | H |
| CF | F | CF$_3$ | H | H | NHCH(CH$_3$)CO$_2$C$_4$H$_9$ | H |
| CF | F | CF$_3$ | H | H | NHCH(CH$_3$)CO$_2$C$_5$H$_{11}$ | H |
| CF | F | CF$_3$ | H | H | NHCH(CH$_3$)CO$_2$H | H |
| CF | F | CF$_3$ | H | H | NHCH(CH$_3$)CO$_2$CH$_2$CH=CH$_2$ | H |
| CF | F | CF$_3$ | H | H | NHCH(CH$_3$)CO$_2$CH$_2$C≡CH | H |
| CF | F | CF$_3$ | H | H | NHCH(CH$_3$)CO$_2$— 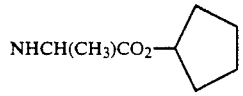 | H |

TABLE 1-continued

[Structure diagram of substituted pyrazole-indazole with positions U, Y, Z, X, V, R¹, R²]

| X | Y | Z | U | V | R¹ | R² |
|---|---|---|---|---|---|---|
| CF | F | CF$_3$ | H | H | NHCH(CH$_3$)CO$_2$-cyclohexyl | H |
| CF | F | CF$_3$ | H | H | NHCH$_3$ | H |
| CF | F | CF$_3$ | H | H | NHC$_2$H$_5$ | H |
| CF | F | CF$_3$ | H | H | NHC$_3$H$_7$ | H |
| CF | F | CF$_3$ | H | H | NHC$_4$H$_9$ | H |
| CF | F | CF$_3$ | H | H | NHC$_5$H$_{11}$ | H |
| CF | F | CF$_3$ | H | H | NHCH$_2$CH=CH$_2$ | H |
| CF | F | CF$_3$ | H | H | NHCH$_2$C≡CH | H |
| CF | F | CF$_3$ | H | H | NHCH$_2$OCH$_3$ | H |
| CF | F | CF$_3$ | H | H | NHCH$_2$CH$_2$F | H |
| CF | F | CF$_3$ | H | H | NH-cyclopentyl | H |
| CF | F | CF$_3$ | H | H | NH-cyclohexyl | H |
| CF | F | CF$_3$ | H | H | NHCH(OCH$_3$)CO$_2$CH$_3$ | H |
| CF | F | CF$_3$ | H | H | NHCH(OCH$_3$)CO$_2$C$_5$H$_{11}$ | H |
| CF | F | CF$_3$ | H | H | NHCH$_2$CO$_2$H | H |
| CF | F | CF$_3$ | H | H | NHCH$_2$CO$_2$CH$_3$ | H |
| CF | F | CF$_3$ | H | H | NHCH$_2$CO$_2$C$_2$H$_5$ | H |
| CF | F | CF$_3$ | H | H | NHCH$_2$CO$_2$C$_3$H$_7$ | H |
| CF | F | CF$_3$ | H | H | NHCH$_2$CO$_2$C$_4$H$_9$ | H |
| CF | F | CF$_3$ | H | H | NHSO$_2$CH$_3$ | H |
| CF | F | CF$_3$ | H | H | NHSO$_2$C$_2$H$_5$ | H |
| CF | F | CF$_3$ | H | H | NHSO$_2$C$_3$H$_7$ | H |
| CF | F | CF$_3$ | H | H | NHSO$_2$C$_4$H$_9$ | H |
| CF | F | CF$_3$ | H | H | NHSO$_2$CH$_2$Cl | H |
| CF | F | CF$_3$ | H | H | NHSO$_2$CH$_2$CH$_2$Cl | H |
| CF | F | CF$_3$ | H | H | NHSO$_2$CH$_2$CH$_2$CH$_2$Cl | H |
| CF | F | CF$_3$ | H | H | N(SO$_2$CH$_3$)CH(CH$_3$)CO$_2$C$_2$H$_5$ | H |
| CF | F | CF$_3$ | H | H | N(SO$_2$CH$_3$)CH$_2$CH=CH$_2$ | H |
| CF | F | CF$_3$ | H | H | N(SO$_2$CH$_3$)CH$_2$C≡CH | H |
| CF | F | CF$_3$ | H | H | N(SO$_2$CH$_3$)CH(OCH$_3$)CO$_2$CH$_3$ | H |
| CF | F | CF$_3$ | H | H | N(SO$_2$CH$_3$)$_2$ | H |
| CF | F | CF$_3$ | H | H | CO$_2$H | H |
| CF | F | CF$_3$ | H | H | CO$_2$CH$_3$ | H |
| CF | F | CF$_3$ | H | H | CO$_2$C$_2$H$_5$ | H |
| CF | F | CF$_3$ | H | H | CO$_2$C$_3$H$_7$ | H |
| CF | F | CF$_3$ | H | H | CO$_2$C$_4$H$_9$ | H |
| CF | F | CF$_3$ | H | H | CO$_2$C$_5$H$_{11}$ | H |
| CF | F | CF$_3$ | H | H | CO$_2$CH$_2$CH=CH$_2$ | H |
| CF | F | CF$_3$ | H | H | CO$_2$CH$_2$C≡CH | H |
| CF | F | CF$_3$ | H | H | CO$_2$CH$_2$OCH$_3$ | H |

TABLE 1-continued

[Structure: pyrazole-fused bicyclic with substituents X, Y, Z, U, V on one ring and R¹, R² on indazole]

| X | Y | Z | U | V | R¹ | R² |
|---|---|---|---|---|---|---|
| CF | F | $CF_3$ | H | H | $CO_2$-cyclopentyl | H |
| CF | F | $CF_3$ | H | H | $CO_2$-cyclohexyl | H |
| CF | F | $CF_3$ | H | H | $CO_2CH_2CH_2F$ | H |
| CF | F | $CF_3$ | H | H | CHO | H |
| CF | F | $CF_3$ | H | H | $COCH_3$ | H |
| CF | F | $CF_3$ | H | H | $COCH_2OCH_3$ | H |
| CF | F | $CF_3$ | H | H | $CH_2OH$ | H |
| CF | F | $CF_3$ | H | H | $CH(OH)CH_3$ | H |
| CF | F | $CF_3$ | H | H | $OCH(CH_3)CO_2CH_3$ | $NO_2$ |
| CF | F | $CF_3$ | H | H | $OCH(CH_3)CO_2C_2H_5$ | $NO_2$ |
| CF | F | $CF_3$ | H | H | $OCH(CH_3)CO_2C_3H_7$ | $NO_2$ |
| CF | F | $CF_3$ | H | H | $OCH(CH_3)CO_2C_4H_9$ | $NO_2$ |
| CF | F | $CF_3$ | H | H | $OCH(CH_3)CO_2C_5H_{11}$ | $NO_2$ |
| CF | F | $CF_3$ | H | H | $OCH(CH_3)CO_2H$ | $NO_2$ |
| CF | F | $CF_3$ | H | H | $OCH(CH_3)CO_2K$ | $NO_2$ |
| CF | F | $CF_3$ | H | H | $OCH(CH_3)CO_2Na$ | $NO_2$ |
| CF | F | $CF_3$ | H | H | $OCH(CH_3)CO_2NH_4$ | $NO_2$ |
| CF | F | $CF_3$ | H | H | $OCH(CH_3)CO_2CH_2CH=CH_2$ | $NO_2$ |
| CF | F | $CF_3$ | H | H | $OCH(CH_3)CO_2CH_2C\equiv CH$ | $NO_2$ |
| CF | F | $CF_3$ | H | H | $OCH(CH_3)CO_2CH_2OCH_3$ | $NO_2$ |
| CF | F | $CF_3$ | H | H | $OCH(CH_3)CO_2$-cyclopentyl | $NO_2$ |
| CF | F | $CF_3$ | H | H | $OCH(CH_3)CO_2$-cyclohexyl | $NO_2$ |
| CF | F | $CF_3$ | H | H | $OCH(CH_3)CO_2CH_2F$ | $NO_2$ |
| CF | F | $CF_3$ | H | H | $SCH(CH_3)CO_2CH_3$ | $NO_2$ |
| CF | F | $CF_3$ | H | H | $SCH(CH_3)CO_2C_5H_{11}$ | $NO_2$ |
| CF | F | $CF_3$ | H | H | $SCH(CH_3)CO_2H$ | $NO_2$ |
| CF | F | $CF_3$ | H | H | $OCH_2CO_2H$ | $NO_2$ |
| CF | F | $CF_3$ | H | H | $OCH_2CO_2CH_3$ | $NO_2$ |
| CF | F | $CF_3$ | H | H | $OCH_2CO_2C_5H_{11}$ | $NO_2$ |
| CF | F | $CF_3$ | H | H | $OCH_3$ | $NO_2$ |
| CF | F | $CF_3$ | H | H | $OC_2H_5$ | $NO_2$ |
| CF | F | $CF_3$ | H | H | $OC_3H_7$ | $NO_2$ |
| CF | F | $CF_3$ | H | H | $OC_4H_9$ | $NO_2$ |
| CF | F | $CF_3$ | H | H | $OC_5H_{11}$ | $NO_2$ |
| CF | F | $CF_3$ | H | H | $OCH_2CH=CH_2$ | $NO_2$ |
| CF | F | $CF_3$ | H | H | $OCH_2C\equiv CH$ | $NO_2$ |
| CF | F | $CF_3$ | H | H | $OCH_2OCH_3$ | $NO_2$ |
| CF | F | $CF_3$ | H | H | O-cyclopentyl | $NO_2$ |

TABLE 1-continued

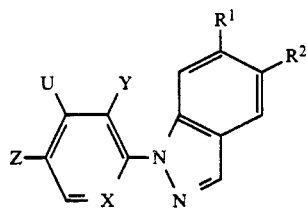

| X | Y | Z | U | V | R¹ | R² |
|---|---|---|---|---|---|---|
| CF | F | CF₃ | H | H | O-cyclohexyl | NO₂ |
| CF | F | CF₃ | H | H | OCOCH₃ | NO₂ |
| CF | F | CF₃ | H | H | OCOC₄H₉ | NO₂ |
| CF | F | CF₃ | H | H | OCO₂CH₃ | NO₂ |
| CF | F | CF₃ | H | H | OCO₂C₂H₅ | NO₂ |
| CF | F | CF₃ | H | H | OCO₂C₃H₇ | NO₂ |
| CF | F | CF₃ | H | H | OCH(CH₃)CH₂OH | NO₂ |
| CF | F | CF₃ | H | H | OCH₂CH₂OH | NO₂ |
| CF | F | CF₃ | H | H | SCH₂CH=CH₂ | NO₂ |
| CF | F | CF₃ | H | H | SCH₂C≡CH | NO₂ |
| CF | F | CF₃ | H | H | SCH₂CO₂CH₃ | NO₂ |
| CF | F | CF₃ | H | H | SCH₂CO₂C₅H₁₁ | NO₂ |
| CF | F | CF₃ | H | H | NHCH(CH₃)CO₂CH₃ | NO₂ |
| CF | F | CF₃ | H | H | NHCH(CH₃)CO₂C₂H₅ | NO₂ |
| CF | F | CF₃ | H | H | NHCH(CH₃)CO₂C₃H₇ | NO₂ |
| CF | F | CF₃ | H | H | NHCH(CH₃)CO₂C₄H₉ | NO₂ |
| CF | F | CF₃ | H | H | NHCH(CH₃)CO₂C₅H₁₁ | NO₂ |
| CF | F | CF₃ | H | H | NHCH(CH₃)CO₂H | NO₂ |
| CF | F | CF₃ | H | H | NHCH(CH₃)CO₂CH₂CH=CH₂ | NO₂ |
| CF | F | CF₃ | H | H | NHCH(CH₃)CO₂CH₂C≡CH | NO₂ |
| CF | F | CF₃ | H | H | NHCH(CH₃)CO₂-cyclopentyl | NO₂ |
| CF | F | CF₃ | H | H | NHCH(CH₃)CO₂-cyclohexyl | NO₂ |
| CF | F | CF₃ | H | H | NHCH₃ | NO₂ |
| CF | F | CF₃ | H | H | NHC₂H₅ | NO₂ |
| CF | F | CF₃ | H | H | NHC₃H₇ | NO₂ |
| CF | F | CF₃ | H | H | NHC₄H₉ | NO₂ |
| CF | F | CF₃ | H | H | NHC₅H₁₁ | NO₂ |
| CF | F | CF₃ | H | H | NHCH₂CH=CH₂ | NO₂ |
| CF | F | CF₃ | H | H | NHCH₂C≡CH | NO₂ |
| CF | F | CF₃ | H | H | NHCH₂OCH₃ | NO₂ |
| CF | F | CF₃ | H | H | NHCH₂CH₂F | NO₂ |
| CF | F | CF₃ | H | H | NH-cyclopentyl | NO₂ |
| CF | F | CF₃ | H | H | NH-cyclohexyl | NO₂ |
| CF | F | CF₃ | H | H | NHCH(OCH₃)CO₂CH₃ | NO₂ |
| CF | F | CF₃ | H | H | NHCH(OCH₃)CO₂C₅H₁₁ | NO₂ |
| CF | F | CF₃ | H | H | NHCH₂CO₂H | NO₂ |
| CF | F | CF₃ | H | H | NHCH₂CO₂CH₃ | NO₂ |
| CF | F | CF₃ | H | H | NHCH₂CO₂C₂H₅ | NO₂ |
| CF | F | CF₃ | H | H | NHCH₂CO₂C₃H₇ | NO₂ |
| CF | F | CF₃ | H | H | NHCH₂CO₂C₄H₉ | NO₂ |
| CF | F | CF₃ | H | H | NHSO₂CH₃ | NO₂ |
| CF | F | CF₃ | H | H | NHSO₂C₂H₅ | NO₂ |
| CF | F | CF₃ | H | H | NHSO₂C₃H₇ | NO₂ |

TABLE 1-continued

| X | Y | Z | U | V | R¹ | R² |
|---|---|---|---|---|---|---|
| CF | F | CF₃ | H | H | NHSO₂C₄H₉ | NO₂ |
| CF | F | CF₃ | H | H | NHSO₂CH₂Cl | NO₂ |
| CF | F | CF₃ | H | H | NHSO₂CH₂CH₂Cl | NO₂ |
| CF | F | CF₃ | H | H | NHSO₂CH₂CH₂CH₂Cl | NO₂ |
| CF | F | CF₃ | H | H | NCH(CH₃)CO₂C₂H₅<br>\|<br>SO₂CH₃ | NO₂ |
| CF | F | CF₃ | H | H | NCH₂CH=CH₂<br>\|<br>SO₂CH₃ | NO₂ |
| CF | F | CF₃ | H | H | NCH₂C≡CH<br>\|<br>SO₂CH₃ | NO₂ |
| CF | F | CF₃ | H | H | NCH(OCH₃)CO₂CH₃<br>\|<br>SO₂CH₃ | NO₂ |
| CF | F | CF₃ | H | H | N(SO₂CH₃)₂ | NO₂ |
| CF | F | CF₃ | H | H | CO₂H | NO₂ |
| CF | F | CF₃ | H | H | CO₂CH₃ | NO₂ |
| CF | F | CF₃ | H | H | CO₂C₂H₅ | NO₂ |
| CF | F | CF₃ | H | H | CO₂C₃H₇ | NO₂ |
| CF | F | CF₃ | H | H | CO₂C₄H₉ | NO₂ |
| CF | F | CF₃ | H | H | CO₂C₅H₁₁ | NO₂ |
| CF | F | CF₃ | H | H | CO₂CH₂CH=CH₂ | NO₂ |
| CF | F | CF₃ | H | H | CO₂CH₂C≡CH | NO₂ |
| CF | F | CF₃ | H | H | CO₂CH₂OCH₃ | NO₂ |
| CF | F | CF₃ | H | H | CO₂-cyclopentyl | NO₂ |
| CF | F | CF₃ | H | H | CO₂-cyclohexyl | NO₂ |
| CF | F | CF₃ | H | H | CO₂CH₂CH₂F | NO₂ |
| CF | F | CF₃ | H | H | CHO | NO₂ |
| CF | F | CF₃ | H | H | COCH₃ | NO₂ |
| CF | F | CF₃ | H | H | COCH₂OCH₃ | NO₂ |
| CF | F | CF₃ | H | H | CH₂OH | NO₂ |
| CF | F | CF₃ | H | H | CH(OH)CH₃ | NO₂ |
| CF | F | CF₃ | H | H | Cl | NO₂ |
| CF | F | CF₃ | H | H | OCH₃ | CN |
| CF | F | CF₃ | H | H | OC₂H₅ | CN |
| CF | F | CF₃ | H | H | OC₃H₇ | CN |
| CF | F | CF₃ | H | H | OCH₃ | Cl |
| CF | F | CF₃ | H | H | OC₂H₅ | Cl |
| CF | F | CF₃ | H | H | OC₃H₇ | Cl |
| CF | F | CF₃ | H | H | OCH₃ | Br |
| CF | F | CF₃ | H | H | OCH₃ | F |
| CF | F | CF₃ | H | H | OCH₂CH=CH₂ | CN |
| CF | F | CF₃ | H | H | OCH₂CH=CH₂ | Cl |
| CF | F | CF₃ | H | H | OCH₂CH=CH₂ | Br |
| CF | F | CF₃ | H | H | OCH₂CH=CH₂ | F |
| CF | F | CF₃ | H | H | OCH₂C≡CH | CN |
| CF | F | CF₃ | H | H | OCH₂C≡CH | Cl |
| CF | F | CF₃ | H | H | OCH₂C≡CH | Br |
| CF | F | CF₃ | H | H | OCH₂C≡CH | F |
| CF | F | CF₃ | H | H | OCH(CH₃)CO₂C₂H₅ | CN |
| CF | F | CF₃ | H | H | OCH(CH₃)CO₂C₂H₅ | Cl |

TABLE 1-continued

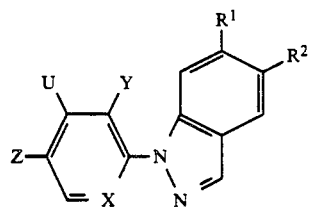

| X | Y | Z | U | V | R$^1$ | R$^2$ |
|---|---|---|---|---|---|---|
| CF | F | CF$_3$ | H | H | OCH(CH$_3$)CO$_2$C$_2$H$_5$ | Br |
| CF | F | CF$_3$ | H | H | OCH(CH$_3$)CO$_2$C$_2$H$_5$ | F |
| CF | F | CF$_3$ | H | H | CHCH$_2$CH=CH$_2$ | CN |
| CF | F | CF | H | H | NHCH$_2$C≡CH | Br |
| CF | F | CF | H | H | NHCH$_2$C≡CH | Cl |
| CF | F | CF | H | H | NHCH$_2$C≡CH | F |
| CF | F | CF$_3$ | H | H | NHCH(CH$_3$)CO$_2$CH$_3$ | CN |
| CF | F | CF$_3$ | H | H | NHCH(CH$_3$)CO$_2$CH$_3$ | Cl |
| CF | F | CF$_3$ | H | H | NHCH(CH$_3$)CO$_2$CH$_3$ | Br |
| CF | F | CF$_3$ | H | H | NHCH(CH$_3$)CO$_2$CH$_3$ | F |
| CF | F | CF$_3$ | H | H | NHSO$_2$CH$_3$ | CN |
| CF | F | CF$_3$ | H | H | NHSO$_2$CH$_3$ | Cl |
| CF | F | CF$_3$ | H | H | NHSO$_2$CH$_3$ | Br |
| CF | F | CF$_3$ | H | H | NHSO$_2$CH$_3$ | F |
| CF | F | CF$_3$ | H | H | SCH(CH$_3$)CO$_2$C$_2$H$_5$ | CN |
| CF | F | CF$_3$ | H | H | SCH(CH$_3$)CO$_2$C$_2$H$_5$ | Cl |
| CF | F | CF$_3$ | H | H | SCH(CH$_3$)CO$_2$C$_2$H$_5$ | Br |
| CF | F | CF$_3$ | H | H | SCH(CH$_3$)CO$_2$C$_2$H$_5$ | F |
| CF | F | CF$_3$ | H | H | CO$_2$C$_2$H$_5$ | CN |
| CF | F | CF$_3$ | H | H | CO$_2$C$_2$H$_5$ | Br |
| CF | F | CF$_3$ | H | H | CO$_2$C$_2$H$_5$ | Cl |
| CF | F | CF$_3$ | H | H | CO$_2$C$_2$H$_5$ | F |
| CF | F | CF$_3$ | H | H | NO$_2$ | NO$_2$ |
| CF | F | CF$_3$ | H | H | CN | NO$_2$ |
| CH | Cl | CF$_3$ | H | H | OCH(CH$_3$)CO$_2$CH$_3$ | CN |
| CH | Cl | CF$_3$ | H | H | OCH(CH$_3$)CO$_2$C$_2$H$_5$ | Cl |
| CH | Cl | CF$_3$ | H | H | OCH(CH$_3$)CO$_2$CH$_3$ | Br |
| CH | Cl | CF$_3$ | H | H | OCH(CH$_3$)CO$_2$C$_2$H$_5$ | F |
| CH | Cl | CF$_3$ | H | H | OCH(CH$_3$)CO$_2$CH$_3$ | H |
| CH | Cl | CF$_3$ | H | H | OCH(CH$_3$)CO$_2$C$_2$H$_5$ | NO$_2$ |
| CH | Cl | CF$_3$ | H | H | NHCH(CH$_3$)CO$_2$CH$_3$ | H |
| CH | Cl | CF$_3$ | H | H | NHCH(CH$_3$)CO$_2$CH$_3$ | Cl |
| CH | Cl | CF$_3$ | H | H | NHCH(CH$_3$)CO$_2$C$_2$H$_5$ | Br |
| CH | Cl | CF$_3$ | H | H | NHCH(CH$_3$)CO$_2$CH$_3$ | F |
| CH | Cl | CF$_3$ | H | H | NHCH(CH$_3$)CO$_2$C$_2$H$_5$ | CN |
| CH | Cl | CF$_3$ | H | H | NHCH(CH$_3$)CO$_2$CH$_3$ | NO$_2$ |
| CH | Cl | CF$_3$ | H | H | CO$_2$C$_2$H$_5$ | CN |
| CH | Cl | CF$_3$ | H | H | CO$_2$C$_2$H$_5$ | Cl |
| CH | Cl | CF$_3$ | H | H | CO$_2$C$_2$H$_5$ | Br |
| CH | Cl | CF$_3$ | H | H | CO$_2$C$_2$H$_5$ | F |
| CH | Cl | CF$_3$ | H | H | CO$_2$C$_2$H$_5$ | H |
| CH | Cl | CF$_3$ | H | H | CO$_2$C$_2$H$_5$ | NO$_2$ |
| CH | Cl | CF$_3$ | H | H | OCH$_3$ | NO$_2$ |
| CH | Cl | CF$_3$ | H | H | OC$_2$H$_5$ | NO$_2$ |
| CH | Cl | CF$_3$ | H | H | OC$_3$H$_7$ | NO$_2$ |
| CH | Cl | CF$_3$ | H | H | OCH$_2$CH=CH$_2$ | NO$_2$ |
| CH | Cl | CF$_3$ | H | H | OCH$_2$C≡CH | NO$_2$ |
| CH | Cl | CF$_3$ | H | H | OCH(OCH$_3$)CO$_2$CH$_3$ | NO$_2$ |
| CH | Cl | CF$_3$ | H | H | NHSO$_2$CH$_3$ | NO$_2$ |
| CH | Cl | CF$_3$ | H | H | NHSO$_2$CH$_2$Cl | NO$_2$ |
| CH | Cl | CF$_3$ | H | H | NHCH$_2$CH=CH$_2$ | NO$_2$ |
| CH | Cl | CF$_3$ | H | H | NHCH$_2$CH=CH$_2$ | CN |
| CH | Cl | CF$_3$ | H | H | NHCH$_2$C≡CH | NO$_2$ |
| CH | Cl | CF$_3$ | H | H | NHCH$_2$C≡CH | CN |
| CH | Cl | CF$_3$ | H | H | NHCH$_3$ | NO$_2$ |
| CH | Cl | CF$_3$ | H | H | NHCH$_3$ | CN |
| CH | Cl | CF$_3$ | H | H | NHC$_2$H$_5$ | NO$_2$ |
| CH | Cl | CF$_3$ | H | H | NHC$_2$H$_5$ | CN |
| CH | Cl | CF$_3$ | H | H | OCH$_3$ | CN |
| CH | Cl | CF$_3$ | H | H | OC$_2$H$_5$ | CN |
| CH | Cl | CF$_3$ | H | H | OC$_3$H$_7$ | CN |
| CH | Cl | CF$_3$ | H | H | OCH$_2$CH=CH$_2$ | CN |
| CH | Cl | CF$_3$ | H | H | OCH$_2$C≡CH | CN |
| CH | Cl | CF$_3$ | H | H | OCH$_3$ | Cl |
| CH | Cl | CF$_3$ | H | H | OCH$_2$CH=CH$_2$ | Cl |
| CH | Cl | CF$_3$ | H | H | OCH$_2$C≡CH | Cl |
| CCl | F | CF$_3$ | H | CH$_3$ | OCH(CH$_3$)CO$_2$CH$_3$ | CN |
| CCl | F | CF$_3$ | H | CH$_3$ | OCH(CH$_3$)CO$_2$C$_2$H$_5$ | Cl |
| CCl | F | CF$_3$ | H | CH$_3$ | OCH(CH$_3$)CO$_2$CH$_3$ | Br |
| CCl | F | CF$_3$ | H | CH$_3$ | OCH(CH$_3$)CO$_2$C$_2$H$_5$ | F |

TABLE 1-continued

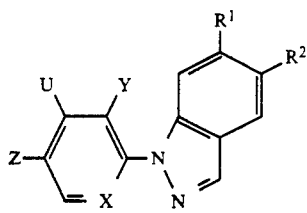

| X | Y | Z | U | V | R¹ | R² |
|---|---|---|---|---|---|---|
| CCl | F | CF₃ | H | CH₃ | OCH(CH₃)CO₂CH₃ | H |
| CCl | F | CF₃ | H | CH₃ | OCH(CH₃)CO₂C₂H₅ | NO₂ |
| CCl | F | CF₃ | H | CH₃ | NHCH(CH₃)CO₂CH₃ | H |
| CCl | F | CF₃ | H | CH₃ | NHCH(CH₃)CO₂CH₃ | Cl |
| CCl | F | CF₃ | H | CH₃ | NHCH(CH₃)CO₂C₂H₅ | Br |
| CCl | F | CF₃ | H | CH₃ | NHCH(CH₃)CO₂CH₃ | F |
| CCl | F | CF₃ | H | CH₃ | NHCH(CH₃)CO₂C₂H₅ | CN |
| CCl | F | CF₃ | H | CH₃ | NHCH(CH₃)CO₂CH₃ | NO₂ |
| CCl | F | CF₃ | H | CH₃ | CO₂C₂H₅ | CN |
| CCl | F | CF₃ | H | CH₃ | CO₂C₂H₅ | Cl |
| CCl | F | CF₃ | H | CH₃ | CO₂C₂H₅ | Br |
| CCl | F | CF₃ | H | CH₃ | CO₂C₂H₅ | F |
| CCl | F | CF₃ | H | CH₃ | CO₂C₂H₅ | H |
| CCl | F | CF₃ | H | CH₃ | CO₂C₂H₅ | NO₂ |
| CCl | F | CF₃ | H | CH₃ | OCH₃ | NO₂ |
| CCl | F | CF₃ | H | CH₃ | OC₂H₅ | NO₂ |
| CCl | F | CF₃ | H | CH₃ | OC₃H₇ | NO₂ |
| CCl | F | CF₃ | H | CH₃ | OCH₂CH=CH₂ | NO₂ |
| CCl | F | CF₃ | H | CH₃ | OCH₂C≡CH | NO₂ |
| CCl | F | CF₃ | H | CH₃ | OCH(OCH₃)CO₂CH₃ | NO₂ |
| CCl | F | CF₃ | H | CH₃ | NHSO₂CH₃ | NO₂ |
| CCl | F | CF₃ | H | CH₃ | NHSO₂CH₂Cl | NO₂ |
| CCl | F | CF₃ | H | CH₃ | NHCH₂CH=CH₂ | NO₂ |
| CCl | F | CF₃ | H | CH₃ | NHCH₂CH=CH₂ | CN |
| CCl | F | CF₃ | H | CH₃ | NHCH₂C≡CH | NO₂ |
| CCl | F | CF₃ | H | CH₃ | NHCH₂C≡CH | CN |
| CCl | F | CF₃ | H | CH₃ | NHCH₃ | NO₂ |
| CCl | F | CF₃ | H | CH₃ | NHCH₃ | CN |
| CCl | F | CF₃ | H | CH₃ | NHC₂H₅ | NO₂ |
| CCl | F | CF₃ | H | CH₃ | NHC₂H₅ | CN |
| CCl | F | CF₃ | H | CH₃ | OCH₃ | CN |
| CCl | F | CF₃ | H | CH₃ | OC₂H₅ | CN |
| CCl | F | CF₃ | H | CH₃ | OC₃H₇ | CN |
| CCl | F | CF₃ | H | CH₃ | OCH₂CH=CH₂ | CN |
| CCl | F | CF₃ | H | CH₃ | OCH₂C≡CH | CN |
| CCl | F | CF₃ | H | CH₃ | OCH₃ | Cl |
| CCl | F | CF₃ | H | CH₃ | OCH₂CH=CH₂ | Cl |
| CCl | F | CF₃ | H | CH₃ | OCH₂C≡CH | Cl |
| CCl | Cl | CF₃ | CH₃ | H | OCH(CH₃)CO₂CH₃ | CN |
| CCl | Cl | CF₃ | CH₃ | H | OCH(CH₃)CO₂C₂H₅ | Cl |
| CCl | Cl | CF₃ | CH₃ | H | OCH(CH₃)CO₂CH₃ | Br |
| CCl | Cl | CF₃ | CH₃ | H | OCH(CH₃)CO₂C₂H₅ | F |
| CCl | Cl | CF₃ | CH₃ | H | OCH(CH₃)CO₂CH₃ | H |
| CCl | Cl | CF₃ | CH₃ | H | OCH(CH₃)CO₂C₂H₅ | NO₂ |
| CCl | Cl | CF₃ | CH₃ | H | NHCH(CH₃)CO₂CH₃ | H |
| CCl | Cl | CF₃ | CH₃ | H | NHCH(CH₃)CO₂CH₃ | Cl |
| CCl | Cl | CF₃ | CH₃ | H | NHCH(CH₃)CO₂C₂H₅ | Br |
| CCl | Cl | CF₃ | CH₃ | H | NHCH(CH₃)CO₂CH₃ | F |
| CCl | Cl | CF₃ | CH₃ | H | NHCH(CH₃)CO₂C₂H₅ | CN |
| CCl | Cl | CF₃ | CH₃ | H | NHCH(CH₃)CO₂CH₃ | NO₂ |
| CCl | Cl | CF₃ | CH₃ | H | CO₂C₂H₅ | CN |
| CCl | Cl | CF₃ | CH₃ | H | CO₂C₂H₅ | Cl |
| CCl | Cl | CF₃ | CH₃ | H | CO₂C₂H₅ | Br |
| CCl | Cl | CF₃ | CH₃ | H | CO₂C₂H₅ | F |
| CCl | Cl | CF₃ | CH₃ | H | CO₂C₂H₅ | H |
| CCl | Cl | CF₃ | CH₃ | H | CO₂C₂H₅ | NO₂ |
| CCl | Cl | CF₃ | CH₃ | H | OCH₃ | NO₂ |
| CCl | Cl | CF₃ | CH₃ | H | OC₂H₅ | NO₂ |
| CCl | Cl | CF₃ | CH₃ | H | OC₃H₇ | NO₂ |
| CCl | Cl | CF₃ | CH₃ | H | OCH₂CH=CH₂ | NO₂ |
| CCl | Cl | CF₃ | CH₃ | H | OCH₂C≡CH | NO₂ |
| CCl | Cl | CF₃ | CH₃ | H | OCH(OCH₃)CO₂CH₃ | NO₂ |
| CCl | Cl | CF₃ | CH₃ | H | NHSO₂CH₃ | NO₂ |
| CCl | Cl | CF₃ | CH₃ | H | NHSO₂CH₂Cl | NO₂ |
| CCl | Cl | CF₃ | CH₃ | H | NHCH₂CH=CH₂ | NO₂ |
| CCl | Cl | CF₃ | CH₃ | H | NHCH₂CH=CH₂ | CN |
| CCl | Cl | CF₃ | CH₃ | H | NHCH₂C≡CH | NO₂ |
| CCl | Cl | CF₃ | CH₃ | H | NHCH₂C≡CH | CN |
| CCl | Cl | CF₃ | CH₃ | H | NHCH₃ | NO₂ |
| CCl | Cl | CF₃ | CH₃ | H | NHCH₃ | CN |

TABLE 1-continued

| X | Y | Z | U | V | R$^1$ | R$^2$ |
|---|---|---|---|---|---|---|
| CCl | Cl | CF$_3$ | CH$_3$ | H | NHC$_2$H$_5$ | NO$_2$ |
| CCl | Cl | CF$_3$ | CH$_3$ | H | NHC$_2$H$_5$ | CN |
| CCl | Cl | CF$_3$ | CH$_3$ | H | OCH$_3$ | CN |
| CCl | Cl | CF$_3$ | CH$_3$ | H | OC$_2$H$_5$ | CN |
| CCl | Cl | CF$_3$ | CH$_3$ | H | OC$_3$H$_7$ | CN |
| CCl | Cl | CF$_3$ | CH$_3$ | H | OCH$_2$CH=CH$_2$ | CN |
| CCl | Cl | CF$_3$ | CH$_3$ | H | OCH$_2$C≡CH | CN |
| CCl | Cl | CF$_3$ | CH$_3$ | H | OCH$_3$ | Cl |
| CCl | Cl | CF$_3$ | CH$_3$ | H | OCH$_2$CH=CH$_2$ | Cl |
| CCl | Cl | CF$_3$ | CH$_3$ | H | OCH$_2$C≡CH | Cl |
| CCl | Cl | C$_2$F$_5$ | H | H | OCH(CH$_3$)CO$_2$CH$_3$ | CN |
| CCl | Cl | C$_2$F$_5$ | H | H | OCH(CH$_3$)CO$_2$C$_2$H$_5$ | Cl |
| CCl | Cl | C$_2$F$_5$ | H | H | OCH(CH$_3$)CO$_2$CH$_3$ | Br |
| CCl | Cl | C$_2$F$_5$ | H | H | OCH(CH$_3$)CO$_2$C$_2$H$_5$ | F |
| CCl | Cl | C$_2$F$_5$ | H | H | OCH(CH$_3$)CO$_2$CH$_3$ | H |
| CCl | Cl | C$_2$F$_5$ | H | H | OCH(CH$_3$)CO$_2$C$_2$H$_5$ | NO$_2$ |
| CCl | Cl | C$_2$F$_5$ | H | H | NHCH(CH$_3$)CO$_2$CH$_3$ | H |
| CCl | Cl | C$_2$F$_5$ | H | H | NHCH(CH$_3$)CO$_2$CH$_3$ | Cl |
| CCl | Cl | C$_2$F$_5$ | H | H | NHCH(CH$_3$)CO$_2$C$_2$H$_5$ | Br |
| CCl | Cl | C$_2$F$_5$ | H | H | NHCH(CH$_3$)CO$_2$CH$_3$ | F |
| CCl | Cl | C$_2$F$_5$ | H | H | NHCH(CH$_3$)CO$_2$C$_2$H$_5$ | CN |
| CCl | Cl | C$_2$F$_5$ | H | H | NHCH(CH$_3$)CO$_2$CH$_3$ | NO$_2$ |
| CCl | Cl | C$_2$F$_5$ | H | H | CO$_2$C$_2$H$_5$ | CN |
| CCl | Cl | C$_2$F$_5$ | H | H | CO$_2$C$_2$H$_5$ | Cl |
| CCl | Cl | C$_2$F$_5$ | H | H | CO$_2$C$_2$H$_5$ | Br |
| CCl | Cl | C$_2$F$_5$ | H | H | CO$_2$C$_2$H$_5$ | F |
| CCl | Cl | C$_2$F$_5$ | H | H | CO$_2$C$_2$H$_5$ | H |
| CCl | Cl | C$_2$F$_5$ | H | H | CO$_2$C$_2$H$_5$ | NO$_2$ |
| CCl | Cl | C$_2$F$_5$ | H | H | OCH$_3$ | NO$_2$ |
| CCl | Cl | C$_2$F$_5$ | H | H | OC$_2$H$_5$ | NO$_2$ |
| CCl | Cl | C$_2$F$_5$ | H | H | OC$_3$H$_7$ | NO$_2$ |
| CCl | Cl | C$_2$F$_5$ | H | H | OCH$_2$CH=CH$_2$ | NO$_2$ |
| CCl | Cl | C$_2$F$_5$ | H | H | OCH$_2$C≡CH | NO$_2$ |
| CCl | Cl | C$_2$F$_5$ | H | H | OCH(OCH$_3$)CO$_2$CH$_3$ | NO$_2$ |
| CCl | Cl | C$_2$F$_5$ | H | H | NHSO$_2$CH$_3$ | NO$_2$ |
| CCl | Cl | C$_2$F$_5$ | H | H | NHSO$_2$CH$_2$Cl | NO$_2$ |
| CCl | Cl | C$_2$F$_5$ | H | H | NHCH$_2$CH=CH$_2$ | NO$_2$ |
| CCl | Cl | C$_2$F$_5$ | H | H | NHCH$_2$CH=CH$_2$ | CN |
| CCl | Cl | C$_2$F$_5$ | H | H | NHCH$_2$C≡CH | NO$_2$ |
| CCl | Cl | C$_2$F$_5$ | H | H | NHCH$_2$C≡CH | CN |
| CCl | Cl | C$_2$F$_5$ | H | H | NHCH$_3$ | NO$_2$ |
| CCl | Cl | C$_2$F$_5$ | H | H | NHCH$_3$ | CN |
| CCl | Cl | C$_2$F$_5$ | H | H | NHC$_2$H$_5$ | NO$_2$ |
| CCl | Cl | C$_2$F$_5$ | H | H | NHC$_2$H$_5$ | CN |
| CCl | Cl | C$_2$F$_5$ | H | H | OCH$_3$ | CN |
| CCl | Cl | C$_2$F$_5$ | H | H | OC$_2$H$_5$ | CN |
| CCl | Cl | C$_2$F$_5$ | H | H | OC$_3$H$_7$ | CN |
| CCl | Cl | C$_2$F$_5$ | H | H | OCH$_2$CH=CH$_2$ | CN |
| CCl | Cl | C$_2$F$_5$ | H | H | OCH$_2$C≡CH | CN |
| CCl | Cl | C$_2$F$_5$ | H | H | OCH$_3$ | Cl |
| CCl | Cl | C$_2$F$_5$ | H | H | OCH$_2$CH=CH$_2$ | Cl |
| CCl | Cl | C$_2$F$_5$ | H | H | OCH$_2$C≡CH | Cl |

The present invention will hereinafter be further illustrated by reference to the following examples which are not to be construed to limit the scope thereof.

Example 1

Preparation of Compound No. 2

To a solution of 5-nitroindazole (1.63 g) in N,N-dimethylformamide (10 ml), 60% sodium hydride (0.5 g) was added, and the resultant mixture was stirred while cooling with ice. After 10 minutes, 2,3-dichloro-5-trifluoromethylpyridine (2.1 g) was added thereto, and the resultant mixture was stirred at room temperature for 30 minutes. After completion of the reaction, the reaction mixture was poured into water and extracted with ethyl acetate. The extract was dried over magnesium sulfate and concentrated under reduced pressure. The residue was purified by silica gel column chromatography with hexane-ethyl acetate (4:1) to give 1-(3-chloro-5-trifluoromethylpyridin-2-yl)-5-nitroindazole (1.8 g)

Example 2

Preparation of Compound No. 4

To a suspension of iron powder (5 g) in acetic acid (10 g), 1-(3-chloro-5-trifluoromethylpyridin-2-yl)-6-nitroindazole [Compound No. 3] (3 g) and water (10 g) were added, and the resultant mixture was refluxed for 3 hours. After completion of the reaction, the reaction mixture was filtered through celite, and the filtrate was poured into water and extracted with ethyl acetate. The extract was dried over magnesium sulfate and concentrated under reduced pressure. The residue was purified by silica gel column chromatography with hexane-ethyl acetate (4:1) to give 1-(3-chloro-5-trifluoromethylpyridin-2-yl)-6-aminoindazole (1.8 g).

Example 3

Preparation of Compound No. 10

To a solution of 1-(3-chloro-5-trifluoromethylpyridin-2-yl)-6-hydroxyindazole [Compound No. 6] (3.14 g) in N,N-dimethylformamide (10 ml), 60% sodium hydride (0.5 g) was added, and the resultant mixture was stirred while cooling with ice. After 10 minutes, ethyl 2-bromopropionate (1.6 g) was added thereto, and the resultant mixture was stirred at room temperature for 30 minutes. After completion of the reaction, the reaction mixture was poured into water and extracted with diethyl ether. The extract was dried over magnesium sulfate and concentrated under reduced pressure. The residue was purified by silica gel column chromatography with hexane-ethyl acetate (4:1) to give ethyl 2-[1-(3-chloro-5-trifluoromethylpyridin-2-yl)indazol-6-yloxy] propionate (3.2 g)

Example 4

Preparation of Compound No. 11

To a solution of 1-(3-chloro-5-trifluoromethylpyridin-2-yl)-5-aminoindazole [Compound No. 7] (3.0 g) in conc. hydrochloric acid (30 g), the solution of sodium nitrite (0.6 g) in water (1 ml) was added dropwise while cooling with ice, and the resultant mixture was stirred at room temperature. After 30 minutes, cuprous chloride (CuCl) (3 g) was added thereto, and the resultant mixture was stirred for 1 hour. After completion of the reaction, the reaction mixture was poured into water and extracted with diethyl ether. The extract was washed with water, dried over magnesium sulfate and concentrated under reduced pressure. The residue was purified by silica gel column chromatography with hexane-ethyl acetate (4:1) to give 1-(3-chloro-5-trifluoromethylpyridin-2-yl)-5-chloroindazole (2.0 g).

Example 5

Preparation of Compound No. 24

To a solution of 1-(2,6-dichloro-4-trifluoromethylphenyl)-6-aminoindazole [Compound No. 47] (3.13 g) in N,N-dimethylformamide (10 ml), 60% sodium hydride (0.5 g) was added, and the resultant mixture was stirred while cooling with ice. After 10 minutes, ethyl 2-bromopropionate (1.6 g) was added thereto, and the resultant mixture was stirred at room temperature for 30 minutes. After completion of the reaction, the reaction mixture was poured into water and extracted with diethyl ether. The extract was dried over magnesium sulfate and concentrated under reduced pressure. The residue was purified by silica gel column chromatography with hexane-ethyl acetate (4:1) to give ethyl 2-[1-(2,6-dichloro-4-trifluoromethylphenyl)indazol-6-ylamino] propionate (1.2 g).

Example 6

Preparation of Compound No. 28

To a solution of 1-(3-chloro-5-trifluoromethylpyridin-2-yl)-6-nitroindazole [Compound No. 3] (10 g) in conc. sulfuric acid (100 g), fuming nitric acid (3.2 g) was added dropwise while cooling with ice, and the resultant mixture was stirred at room temperature for 3 hours. After completion of the reaction, the reaction mixture was poured into ice water, and precipitated crystals were collected by filtration, washed and dried. The crystals were purified by silica gel column chromatography with hexane-ethyl acetate (4:1) to give 1-(3-chloro-5-trifluoromethylpyridin-2-yl)-5,6-dinitroindazole (8.0 g).

Example 7

Preparation of Compound No. 30

To a solution of 1-(2,6-dichloro-4-trifluoromethylphenyl)-6-hydroxyindazole [Compound No. 80] (10 g) in dichloromethane (30 ml), triethylamine (5 g) and methoxycarbonyl chloride (7 g) were added, and the resultant mixture was refluxed for 3 hours. After completion of the reaction, the reaction mixture was poured into water and extracted with diethyl ether. The extract was washed with water, dried over magnesium sulfate and concentrated under reduced pressure. The residue was purified by silica gel column chromatography with hexane-ethyl acetate (4:1) to give methyl 1-(2,6-dichloro-4-trifluoromethylphenyl)indazol-6-yl carbonate (11 g).

Example 8

Preparation of Compound No. 31

To a solution of methyl 1-(2,6-dichloro-4-trifluoromethylphenyl)-5-nitroindazol-6-yl carbonate (8 g) in ethanol (100 g), 30% sulfuric acid (20 ml) was added, and the resultant mixture was refluxed for 6 hours. After completion of the reaction, the reaction mixture was poured into water and extracted with diethyl ether. The extract was dried over magnesium sulfate and concentrated under reduced pressure. The residue was purified by silica gel column chromatography with hexane-ethyl acetate (4:1) to give 1-(2,6-dichloro-4-trifluoromethylphenyl)-6-hydroxy-5-nitroindazole (4.1 g).

Example 9

Preparation of Compound No. 34

To a solution of 1-(2,6-dichloro-4-trifluoromethylphenyl)-6-hydroxy-5-nitroindazole [Compound No. 31] (3 g) in N,N-dimethylformamide, 60% sodium hydride (0.5 g) was added, and the resultant mixture was stirred while cooling with ice. After 10 minutes, propargyl bromide (1.2 g) was added thereto, and the resultant mixture was stirred at room temperature for 30 minutes. After completion of the reaction, the reaction mixture was poured into water and extracted with diethyl ether. The extract was dried over magnesium sulfate and concentrated under reduced pressure. The residue was purified by silica gel column chromatography with hexane-ethyl acetate (4:1) to give 1-(2,6-dichloro-4-trifluoromethylphenyl)-5-nitro-6-propargyloxyindazole (2.8 g).

Example 10

Preparation of Compound No. 41

To a solution of methyl 1-(3-chloro-5-trifluoromethylpyridin-2-yl)indazol-6-yl carbonate [Compound No. 39] (10 g) in conc. sulfuric acid (100 g), fuming nitric acid (3.5 g) was added dropwise while cooling with ice, and the resultant mixture was stirred at room temperature for 3 hours. After completion of the reaction, the reaction mixture was poured into ice water, and the precipitated crystals were collected by filtration, washed and dried. The crystals were purified by silica gel column chromatography with hexane-ethyl acetate (4:1) to give methyl 1-(3-chloro-5-trifluoromethylpyridin-2-yl)-5-nitroindazol-6-yl carbonate (8.2 g).

Example 11

Preparation of Compound No. 48

To a solution of 1-(3-chloro-5-trifluoromethylpyridin-2-yl)-5,6-diaminoindazole [Compound No. 81] (5.0 g) in acetic acid (20 g), a solution of sodium nitrite (0.9 g) in water (3 ml) was added dropwise at room temperature. After completion of the reaction, the reaction mixture was poured into water, and the precipitated crystals were collected by filtration, washed and dried. The crystals were purified by silica gel column chromatography with hexane-ethyl acetate (4:1) to give 5-(3-chloro-5-trifluoromethylpyridin-2-yl)[1,2,3]triazolo[4,5-f]indazole (5.0 g).

Example 12

Preparation of Compound Nos. 53 and 64

To a solution of 5-(3-chloro-5-trifluoromethylpyridin-2-yl)[1,2,3]triazolo[4,5-f]indazole [Compound No. 48] (1.0 g) in N,N-dimethylformamide (10 g), methyl 2-bromopropionate (0.5 g) and potassium carbonate (1 g) were added, and the resultant mixture was stirred at 40° C. for 3 hours. After completion of the reaction, the reaction mixture was poured into water and extracted with ethyl acetate. The extract was washed, dried over magnesium sulfate and concentrated under reduced pressure. The residue was purified by silica gel column chromatography with hexane-ethyl acetate (4:1) to give 5-(3-chloro-5-trifluoromethylpyridin-2-yl)-3-(1-methoxycarbonylethyl)[1,2,3]triazolo[4,5-f]indazole (0.3 g) and 5-(3-chloro-5-trifluoromethylpyridin-2-yl)-1-(1-methoxycarbonylethyl)[1,2,3]triazolo[4,5-f]indazole (0.1 g).

Example 13

Preparation of Compound No. 61

To a solution of ethyl 1-(2,6-dichloro-4-trifluoromethylphenyl)indazol-6-yl carboxylate [Compound No. 62] (3 g) in conc. sulfuric acid (20 g), fuming nitric acid (0.7 g) was added dropwise while cooling with ice, and the resultant mixture was stirred at room temperature for 3 hours. After completion of the reaction, the reaction mixture was poured into ice water, and the precipitated crystals were collected by filtration, washed and dried. The crystals were purified by silica gel column chromatography with hexane-ethyl acetate (4:1) to give ethyl 1-(2,6-dichloro-4-trifluoromethylphenyl)-5-nitroindazol-6-yl carboxylate (2.1 g).

Example 14

Preparation of Compound No. 62

To a solution of ethyl indazol-6-yl carboxylate (1.8 g) in N,N-dimethylformamide (10 ml), 60% sodium hydride (0.5 g) was added, and the resultant mixture was stirred while cooling with ice. After 10 minutes, 3,5-dichloro-4-fluorobenztrifluoride (2.2 g) was added thereto, and the resultant mixture was stirred at room temperature for 30 minutes. After completion of the reaction, the reaction mixture was poured into water and extracted with ethyl acetate. The extract was dried over magnesium sulfate and concentrated under reduced pressure. The residue was purified by silica gel column chromatography with hexaneethyl acetate (4:1) to give ethyl 1-(2,6-dichloro-4-trifluoromethylphenyl)indazol-6-yl carboxylate (2.0 g).

Example 15

Preparation of Compound No. 77

To a solution of 5-nitroindazole in N,N-dimethylformamide (20 g), 60% sodium hydride (0.5 g) was added slowly, and the resultant mixture was stirred while cooling with ice for 30 minutes. To the mixture, 3,4-dichlorobenztrifluoride (2.2 g) was added, and the resultant mixture was stirred at 80° C. for 2 hours. After completion of the reaction, the reaction mixture was poured into water and extracted with ethyl acetate. The extract was concentrated and the residue was purified by silica gel column chromatography with hexane-ethyl acetate (4:1) to give 1-(2-chloro-4-trifluoromethylphenyl)-5-nitroindazole (2.1 g).

Example 16

Preparation of Compound No. 79

To a solution of 6-nitroindazole (1.63 g) in N,N-dimethylformamide (10 ml), 60% sodium hydride (0.5 g) was added, and the resultant mixture was stirred while cooling with ice. After 10 minutes, 3,5-dichloro-4-fluorobenztrifluoride (2.1 g) was added thereto, and the resultant mixture was stirred at room temperature for 30 minutes. After completion of the reaction, the reaction mixture was poured into water and extracted with ethyl acetate. The extract was dried over magnesium sulfate and concentrated under reduced pressure. The residue was purified by silica gel column chromatography with hexane-ethyl acetate (4:1) to give 1-(2,6-dichloro-4-trifluoromethylphenyl)-6-nitroindazole (1.3 g).

Example 17

Preparation of Compound No. 80

To a suspension of 1-(2,6-dichloro-4-trifluoromethylphenyl)-6-aminoindazole [Compound No. 47] (10 g) in 50% sulfuric acid (30 g), a solution of sodium nitrite (3 g) in water (10 g) was added dropwise while cooling with ice, and the resultant mixture was stirred. After 1 hour, the mixture was added dropwise for 1 hour to 10% sulfuric acid heated at 100° C. to 110° C., and the resultant mixture was refluxed for 30 minutes. After completion of the reaction, the reaction mixture was cooled and extracted with ethyl acetate. The extract was dried over magnesium sulfate and concentrated under reduced pressure. The residue was purified by silica gel column chromatography with hexaneethyl acetate (4:1) to give 1-(2,6-dichloro-4-trifluoromethylphenyl)-6-hydroxyindazole (6 g).

Example 18

Preparation of Compound No. 81

1-(3-Chloro-5-trifluoromethylpyridin-2-yl) -5,6-dinitroindazole [Compound No. 28] (8.0 g) was dissolved in ethyl acetate (100 g) and reduced with 10% Pd-C (0.1 g) at ordinary temperature under atmospheric pressure for 8 hours. After completion of the reaction, the reaction mixture was filtered to remove the Pd-C, and the filtrate was concentrated under reduced pressure to give 1-(3-chloro-5-trifluoromethylpyridin-2-yl)-5,6-diaminoindazole (7.2 g).

In the same manner as described above, various compounds (1) as shown in Table 2 were obtained.

TABLE 2

| No. | X | Y | Z | U | V | R$^1$ | R$^2$ | Melting point (°C.) |
|---|---|---|---|---|---|---|---|---|
| 1 | N | Cl | CF$_3$ | H | H | H | H | 72–73 |
| 2 | N | Cl | CF$_3$ | H | H | H | NO$_2$ | 124–125 |
| 3 | N | Cl | CF$_3$ | H | H | NO$_2$ | H | 163–164 |
| 4 | N | Cl | CF$_3$ | H | H | NH$_2$ | H | 172–173 |
| 5 | N | Cl | CF$_3$ | H | H | OCH(CH$_3$)CO$_2$CH$_3$ | H | 103–104 |
| 6 | N | Cl | CF$_3$ | H | H | OH | H | 159–160 |
| 7 | N | Cl | CF$_3$ | H | H | H | NH$_2$ | 140–141 (dec.) |
| 8 | N | Cl | CF$_3$ | H | H | OCH(CH$_3$)CO$_2$C$_2$H$_5$ | NO$_2$ | 133–135 |
| 9 | CCl | Cl | CF$_3$ | H | H | H | NO$_2$ | 128–129 |
| 10 | N | Cl | CF$_3$ | H | H | OCH(CH$_3$)CO$_2$C$_2$H$_5$ | H | 84–85 |
| 11 | N | Cl | CF$_3$ | H | H | H | Cl | 135–136 |
| 12 | CH | Cl | CF$_3$ | H | H | NO$_2$ | H | 125–126 |
| 13 | N | Cl | CF$_3$ | H | H | OCH$_2$CO$_2$CH$_3$ | H | 72–73 |
| 14 | N | Cl | CF$_3$ | H | H | OCH$_2$C≡CH | H | 72–73 |
| 15 | CCl | Cl | CF$_3$ | H | H | OCH(CH$_3$)CO$_2$CH$_3$ | H | 112–113 |
| 16 | CCl | Cl | CF$_3$ | H | H | OCH(CH$_3$)CO$_2$C$_4$H$_9$-(n) | H | 80–81 |
| 17 | N | Cl | CF$_3$ | H | H | NHSO$_2$CH$_3$ | H | resinous |
| 18 | CCl | Cl | CF$_3$ | H | H | OCHCO$_2$CH$_3$ (↑ CH$_3$) | H | 108–110 |
| 19 | N | Cl | CF$_3$ | H | H | OCH(OCH$_3$)CO$_2$CH$_3$ | H | 88–89 |
| 20 | CCl | Cl | CF$_3$ | H | H | OCH(CH$_3$)CO$_2$C$_3$H$_7$-(i) | H | 93–94 |
| 21 | CCl | Cl | CF$_3$ | H | H | OCH(CH$_3$)CO$_2$C$_2$H$_5$ | H | 77–78 |
| 22 | CCl | Cl | CF$_3$ | H | H | NHSO$_2$CH$_3$ | H | 172–173 |
| 23 | CF | Cl | CF$_3$ | H | H | H | NO$_2$ | 148–149 |
| 24 | CCl | Cl | CF$_3$ | H | H | NHCH(CH$_3$)CO$_2$C$_2$H$_5$ | H | 136–137 |
| 25 | CF | Cl | CF$_3$ | H | H | NO$_2$ | H | 178–181 |
| 26 | CH | Cl | CF$_3$ | H | H | OH | H | 161–163 |
| 27 | CH | Cl | CF$_3$ | H | H | OCH(CH$_3$)CO$_2$C$_2$H$_5$ | H | 118–120 |
| 28 | N | Cl | CF$_3$ | H | H | NO$_2$ | NO$_2$ | 181–183 |
| 29 | N | Cl | CF$_3$ | H | H | NHCH$_2$CH=CH$_2$ | NO$_2$ | 136–137 |
| 30 | CCl | Cl | CF$_3$ | H | H | OCOOCH$_3$ | H | 128–129 |
| 31 | CCl | Cl | CF$_3$ | H | H | OH | NO$_2$ | 150–151 |
| 32 | CCl | Cl | CF$_3$ | H | H | OCH$_3$ | NO$_2$ | 218–219 |
| 33 | CCl | Cl | CF$_3$ | H | H | OCH$_2$CH=CH$_2$ | NO$_2$ | 118–119 |
| 34 | CCl | Cl | CF$_3$ | H | H | OCH$_2$C≡CH | NO$_2$ | 218–220 |
| 35 | CCl | Cl | CF$_3$ | H | H | OCH(CH$_3$)CO$_2$CH$_3$ | NO$_2$ | 112–113 |
| 36 | CCl | Cl | CF$_3$ | H | H | OCH(CH$_3$)CO$_2$C$_3$H$_7$-(i) | NO$_2$ | 114–115 |
| 37 | CCl | Cl | CF$_3$ | H | H | OCH(CH$_3$)CO$_2$C$_5$H$_{11}$-(n) | NO$_2$ | resinous |
| 38 | CF | F | CF$_3$ | H | H | H | NO$_2$ | 97–98 |
| 39 | N | Cl | CF$_3$ | H | H | OCOOCH$_3$ | H | 140–141 |
| 40 | CCl | Cl | CF$_3$ | H | H | OCOOCH$_3$ | NH$_2$ | 165–166 |
| 41 | N | Cl | CF$_3$ | H | H | OCOOCH$_3$ | NO$_2$ | 123–124 |
| 42 | N | Cl | CF$_3$ | H | H | OH | NO$_2$ | 107–108 |
| 43 | N | Cl | CF$_3$ | H | H | OCH$_2$CH=CH$_2$ | NO$_2$ | 150–151 |
| 44 | N | Cl | CF$_3$ | H | H | OCH$_2$C≡CH | NO$_2$ | 132–133 |
| 45 | N | Cl | CF$_3$ | H | H | OCH$_3$ | NO$_2$ | 162–163 |
| 46 | CCl | Cl | CF$_3$ | H | H | OCH$_3$ | Cl | 130–132 |
| 47 | CCl | Cl | CF$_3$ | H | H | NH$_2$ | H | 175–177 |
| 48 | N | Cl | CF$_3$ | H | H | HN—N=N | | 270 (dec.) |
| 49 | N | Cl | CF$_3$ | H | H | H | Br | 131–132 |
| 50 | N | Cl | CF$_3$ | H | H | CO$_2$C$_2$H$_5$ | H | 101–102 |
| 51 | N | Cl | CF$_3$ | H | H | CO$_2$C$_2$H$_5$ | NO$_2$ | 150–151 |
| 52 | N | Cl | CF$_3$ | H | H | CO$_2$H | NO$_2$ | 251–253 |

TABLE 2-continued

[Structure with R1, R2 on indazole fused benzene ring; U, Y, Z, X, V on pyridine/benzene ring attached to N of indazole]

| No. | X | Y | Z | U | V | R¹ | R² | Melting point (°C.) |
|---|---|---|---|---|---|---|---|---|
| 53 | N | Cl | CF₃ | H | H | —N—N=N—<br>│<br>CH(CH₃)CO₂CH₃ |  | 179–180 |
| 54 | CF | Cl | CF₃ | H | H | CO₂C₂H₅ | H | 89–90 |
| 55 | CF | Cl | CF₃ | H | H | CO₂H | H | 281–282 |
| 56 | CF | F | CF₃ | H | H | CO₂C₂H₅ | H | 80–81 |
| 57 | CCl | Cl | CF₃ | H | H | OCH(CH₂)CO₂CH₃ | Cl | resinous |
| 58 | CH | Cl | CF₃ | H | H | CO₂C₂H₅ | H | 55–56 |
| 59 | CCl | Cl | CF₃ | H | H | OCH(CH₃)CO₂H | NO₂ | 191–192 |
| 60 | CCl | Cl | CF₃ | H | H | OCH(CH₃)CH₂OH | H | resinous |
| 61 | CCl | Cl | CF₃ | H | H | CO₂C₂H₅ | NO₂ | 125–126 |
| 62 | CCl | Cl | CF₃ | H | H | CO₂C₂H₅ | H | 103–104 |
| 63 | CCl | Cl | CF₃ | H | H | CO₂H | NO₂ | 137–138 |
| 64 | N | Cl | CF₃ | H | H | —N=N—N—<br>│<br>CH(CH₃)CO₂CH₃ |  | 136–137 |
| 65 | N | Cl | CF₃ | H | H | CH₂OH | H | resinous |
| 66 | N | Cl | CF₃ | H | H | CO₂CH₃ | H | 117–118 |
| 67 | N | Cl | CF₃ | H | H | CO₂CH₃ | NO₂ | 147–148 |
| 68 | N | Cl | CF₃ | H | H | CHO | H | 107–108 |
| 69 | CF | F | CF₃ | H | H | NO₂ | H | 138–139 |
| 70 | N | Cl | CF₃ | H | H | NCH(CH₃)CO₂CH₃<br>│<br>SO₂CH₃ | H | 181–183 |
| 71 | N | Cl | CF₃ | H | H | N(CH₃)—N=N |  | 199–200 |
| 72 | CF | Cl | CF₃ | H | H | NH₂ | H | 188–190 |
| 73 | CF | Cl | CF₃ | H | H | OCH(CH₃)CO₂CH₃ | H | 190–191 |
| 74 | N | Cl | CF₃ | H | H | NO₂ | Br | 171–173 |
| 75 | N | Cl | CF₃ | H | H | CH₂CHClCO₂CH₃ | H | resinous |
| 76 | N | Cl | CF₃ | H | H | NH₂ | Br | 128 (dec.) |
| 77 | CH | Cl | CF₃ | H | H | H | NO₂ | 138–139 |
| 78 | N | Cl | CF₃ | H | H | H | CN | 109–111 |
| 79 | CCl | Cl | CF₃ | H | H | NO₂ | H | 163–165 |
| 80 | CCl | Cl | CF₃ | H | H | OH | H | 233–234 |
| 81 | N | Cl | CF₃ | H | H | NH₂ | NH₂ | 125–127 (dec.) |

The starting compound (3) may be produced according to the following scheme:

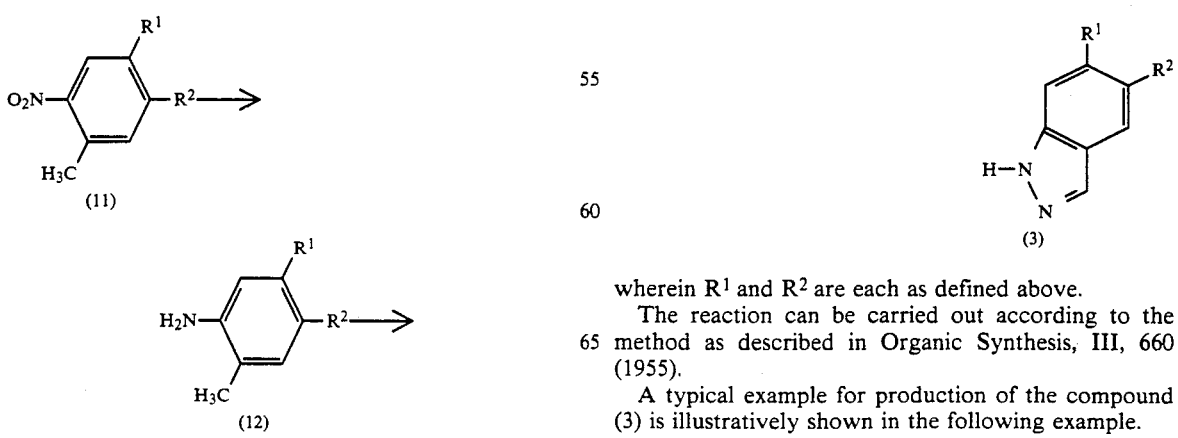

wherein R¹ and R² are each as defined above.

The reaction can be carried out according to the method as described in Organic Synthesis, III, 660 (1955).

A typical example for production of the compound (3) is illustratively shown in the following example.

Example 19

Ethyl 4-methyl-3-nitrobenzoate (105 g) was dissolved in glacial acetic acid (4 l), followed by stirring. To the solution, a solution of sodium nitrite (32 g) in water (80 ml) was added at once at a temperature of 10° C. to 15° C., and the resultant mixture was stirred at room temperature for 3 days. After completion of the reaction, the reaction mixture was evaporated under reduced pressure to remove acetic acid. Water was added to the residue, and the precipitated crystals were collected by filtration. The collected crystals were washed with water and dried. The obtained crystals was further washed with methanol and diethyl ether, and dried to give ethyl indazol-6-yl carboxylate (90 g), m.p. 125°-126° C.

The compounds (1) of the present invention produce a strong herbicidal activity against a wide variety of weeds including broad-leaved weeds, Graminaceous weeds, Commelinaceous weeds and Cyperaceous weeds in agricultural plowed fields by foliar or soil treatment. Some of the compounds (1) do not produce any material phytotoxicity on various agricultural crops such as corn, wheat, rice plant, soybean and cotton. Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursapastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), sun spurge (*Euphorbia helioscopia*) and spotted spurge (*Euphorbia maculata*). Examples of Graminaceous weeds include Japanese millet (*Echinochloa frumentacea*), barnyardgrass (*Echinochloa crusgalli*), green foxtail (*Setaria viridis*), large crabgrass (*Digitaria sanguinalis*), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), bermudagrass (*Cynodon dactylon*) and giant foxtail (*Setaria faberi*). Examples of the Commelinaceous weeds include asiatic dayflower (*Commelina communis*). Examples of the Cyperaceous weeds include rice flatsedge (*Cyperus iria*).

The compounds (1) of the present invention are also effective in exterminating paddy field weeds including Graminaceous weeds such as barnyardgrass (*Echinochloa oryzicola*); broad-leaved weeds such as common falsepimpernel (*Lindernia procumbens*), indian toothcup (*Rotala indica*) and waterwort (*Elatine triandra*); Cyperaceous weeds such as umbrella sedge (*Cyperus difformis*), hardstem bulrush (*Scirpus juncoides*) and needle spikerush (*Eleocharis acicularis*); and others such as monochoria (*Monochoria vaginalis*) and arrowhead (*Sagittaria pygmaea*). Some of the compounds (1) of the present invention do not produce any phytotoxicity to rice plants on flooding treatment.

Particularly, the compounds (1) of the present invention have an excellent herbicidal activity under the foliar treatment of upland fields and the flooding treatment of paddy fields.

For the practical usage of the compound (1), it is usually formulated with conventional solid or liquid carriers or diluents as well as surfactants or auxiliary agents into conventional preparation forms such as emulsifiable concentrates, wettable powders, flowables, granules and water-dispersible granules. The content of the compound (1) as the active ingredient in such preparation forms is normally within a range of 0.03% to 80% by weight, preferably of 0.05% to 70% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate. As the liquid carrier or diluent, there may be exemplified aromatic hydrocarbons (e.g., xylene, methylnaphthalene), alcohols (e.g., isopropanol, ethylene glycol, cellosolve), ketones (e.g., acetone, cyclohexanone, isophorone), vegetable oils (e.g., soybean oil, cotton seed oil), dimethylsulfoxide, N,N-dimethylformamide, acetonitrile and water.

Examples of the surfactant used for emulsification, dispersing or spreading are those of anionic type, such as alkylsulfates, alkylsulfonates, alkylarylsulfonates, dialkylsulfosuccinates and phosphates of polyoxyethylene alkylaryl ethers; and those of nonionic type, such as polyoxyethylene alkyl ethers, polyoxyethylene alkylaryl ethers, polyoxyethylene polyoxypropylene block copolymers, sorbitan fatty acid esters and polyoxyethylene sorbitan fatty acid esters.

Examples of the auxiliary agent are ligninsulfonates, alginates, polyvinyl alcohol, gum arabic, carboxymethyl cellulose (CMC) and isopropyl acid phosphate (PAP).

Practical embodiments of the herbicidal composition according to the present invention are illustratively shown in the following formulation examples wherein parts are by weight. The compound number of the active ingredient corresponds to the one in Table 2.

Formulation Example 1

Fifty parts of any one of Compound Nos. 1-16, 18-36, 38-56, 58, 59, 61-64, 66-74 and 76-81, 3 parts of calcium ligninsulfonate, 2 parts of sodium laurylsulfate and 45 parts of synthetic hydrous silicate are well mixed while being powdered to obtain a wettable powder.

Formulation Example 2

Five parts of any one of Compound Nos. 1-81, 14 parts of polyoxyethylenestyrylphenyl ether, 6 parts of calcium dodecylbenzenesulfonate, 25 parts of xylene and 50 parts of cyclohexanone are well mixed to obtain an emulsifiable concentrate.

Formulation Example 3

Two parts of any one of Compound Nos. 1-16, 18-36, 38-56, 58, 59, 61-64, 66-74 and 76-81, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

Formulation Example 4

Twenty-five parts of any one of Compound Nos. 1-16, 18-36, 38-56, 58, 59, 61-64, 66-74 and 76-81 are mixed with 3 parts of polyoxyethylene sorbitan monooleate, 3 parts of carboxymethyl cellulose and 69 parts of water, and pulverized until the particle size of the mixture becomes less than 5 microns to obtain a flowable.

The compound (1) thus formulated in any suitable formulation is used for pre-emergence or post-emergence control of undesired weeds by the soil or foliar treatment for upland fields and by the flooding treatment for paddy fields. The soil treatment includes soil surface treatment and soil incorporation. The foliar treatment is effected by application over the plants or by directed application to the weeds to keep any chemical off the crop foliage.

Further, the compound (1) of the present invention may be used together with any other herbicide to enhance its herbicidal activity. Moreover, it may also be used in admixture with insecticides, acaricides, nematocides, fungicides, plant growth regulators, fertilizers, soil improver and the like.

The compound (1) of the present invention can be used as an active ingredient of herbicides to be employed for paddy fields, upland fields, orchards, pasture lands, lawns, forests and non-agricultural fields.

When the compound (1) of the present invention is used as an active ingredient of herbicides, the dosage thereof is usually in the range of 0.01 to 80 grams, preferably 0.02 to 40 grams per are, although it may vary depending on the prevailing weather conditions, formulation type employed, application timing, type of application, soil involved, crop and weed species, and the like. A designated amount of the compound (1) formulated in the form of an emulsifiable concentrate, wettable powder, flowable or the like may usually be employed by diluting it with water at a volume of about 1 to 10 liters per are, if necessary, with addition of an adjuvant such as a spreading agent. The compound (1) formulated in the form of a flowable or granules may usually be applied without dilution.

Examples of the adjuvant include, in addition to the surfactants as described above, polyoxyethylene resin acids (esters), ligninsulfonates, abietates, dinaphthylmethanedisulfonates, crop oil concentrates, and crop oils such as soybean oil, corn oil, cotton seed oil and sunflower oil.

The compound (1) of the present invention can also be used as an active ingredient of harvestaid agents such as defoliants and desiccating agents for such as cotton (*Gossypium hirsutum*) and potato (*Solanum tuberosum*).

The biological data of the compound (1) as a herbicide will be illustratively shown in the following test examples wherein the phytotoxicity to crop plants and the herbicidal activity on weeds were determined by visual observation as to the degree of germination and the growth inhibition, and rated with an index 0, 1, 2, 3, 4 or 5, the numeral "0" indicating no material difference as seen in comparison with the untreated plants and the numeral "5" indicating the complete inhibition or death of the test plants.

Test Example 1

Cylindrical plastic pots (diameter, 10 cm; height, 10 cm) were filled with upland field soil, and the seeds of Japanese millet and velvetleaf were sowed therein and covered with soil. A designated amount of the test compound formulated in an emulsifiable concentrate as in Formulation Example 2 was diluted with water, and the dilution was sprayed onto the soil surface by means of a small sprayer at a spray volume of 10 liters per are. The test plants were grown in a greenhouse for 20 days, and the herbicidal activity was examined. The results are shown in Table 3.

TABLE 3

| Compound No. | Dosage (g/are) | Herbicidal activity | |
|---|---|---|---|
| | | Japanese millet | Velvet-leaf |
| 2 | 20 | 5 | 5 |
| 5 | 5 | 5 | 5 |
| 8 | 5 | 5 | 5 |
| 9 | 20 | 5 | 4 |
| 10 | 5 | 5 | 5 |
| 13 | 5 | 4 | 4 |
| 15 | 5 | 5 | 5 |
| 16 | 5 | 5 | 5 |
| 17 | 5 | 4 | 5 |
| 18 | 5 | 5 | 5 |
| 23 | 5 | 5 | 5 |
| 24 | 5 | 5 | 5 |
| 27 | 5 | 4 | 5 |
| 28 | 5 | 4 | 5 |
| 29 | 20 | 4 | 4 |
| 32 | 20 | 4 | 5 |
| 38 | 5 | 5 | 4 |
| 45 | 5 | 4 | 5 |
| 53 | 5 | 5 | 4 |
| 56 | 5 | 5 | 5 |
| 58 | 20 | 4 | 4 |
| 59 | 20 | 4 | 5 |
| 60 | 5 | 5 | 5 |
| 63 | 5 | 4 | 5 |
| 64 | 5 | 4 | 5 |
| 65 | 20 | 4 | 5 |
| 66 | 20 | 4 | 4 |
| 67 | 20 | 5 | 4 |
| 70 | 5 | 5 | 5 |
| 73 | 5 | 5 | 5 |

Test Example 2

Cylindrical plastic pots (diameter, 10 cm; height, 10 cm) were filled with upland field soil, and the seeds of Japanese millet, velvetleaf and tall morningglory were sowed therein, and cultivated in a greenhouse for 10 days. A designated amount of the test compound formulated in an emulsifiable concentrate as in Formulation Example 2 was diluted with water containing a spreading agent, and the dilution was sprayed over the foliage of the test plants by mean of a small sprayer at a spray volume of 10 liters per are. The test plants were further grown in the greenhouse for 20 days, and the herbicidal activity wa examined. The results are shown in Table 4.

TABLE 4

| Compound No. | Dosage (g/are) | Herbicidal activity | | |
|---|---|---|---|---|
| | | Japanese millet | Velvet-leaf | Tall morning-glory |
| 1 | 20 | — | 4 | 5 |
| 2 | 20 | 5 | 5 | 5 |
| 5 | 5 | 5 | 5 | 5 |
| 8 | 20 | 5 | 5 | 5 |
| 9 | 20 | 5 | 5 | 5 |
| | 5 | 5 | 5 | 5 |
| 10 | 5 | 5 | 5 | 5 |
| 11 | 20 | 5 | 5 | 5 |
| 13 | 5 | 5 | 5 | 5 |
| 14 | 5 | 5 | 5 | 5 |

TABLE 4-continued

| Compound No. | Dosage (g/are) | Herbicidal activity | | |
|---|---|---|---|---|
| | | Japanese millet | Velvet-leaf | Tall morning-glory |
| 16 | 5 | 5 | 5 | 5 |
| 17 | 5 | 4 | 5 | 5 |
| 18 | 5 | 5 | 5 | 5 |
| 20 | 5 | 5 | 5 | 5 |
| 21 | 5 | 5 | 5 | 5 |
| 22 | 20 | 5 | 5 | 5 |
| 23 | 5 | 5 | 5 | 5 |
| 25 | 20 | 4 | 5 | 5 |
| 27 | 5 | 4 | 5 | 5 |
| 29 | 20 | 5 | 5 | 5 |
| 32 | 20 | 5 | 5 | — |
| 33 | 5 | 5 | 5 | — |
| 34 | 5 | 5 | 5 | — |
| 35 | 5 | 5 | 5 | — |
| 36 | 5 | 5 | 5 | — |
| 37 | 5 | 5 | 5 | — |
| 38 | 5 | 5 | 5 | — |
| 43 | 5 | 5 | 5 | — |
| 44 | 5 | 5 | 5 | — |
| 45 | 5 | 5 | 5 | — |
| 47 | 20 | 5 | 5 | 5 |
| 48 | 20 | 5 | 5 | 5 |
| 49 | 20 | 4 | 5 | 5 |
| 50 | 5 | 5 | 5 | 5 |
| 51 | 5 | 5 | 5 | 5 |
| 52 | 5 | 5 | 5 | 5 |
| 53 | 20 | 5 | 5 | 5 |
| 54 | 20 | 5 | 5 | 5 |
| 55 | 20 | 5 | 5 | 5 |
| 56 | 5 | 5 | 5 | 5 |
| 57 | 20 | 5 | 5 | 5 |
| 58 | 20 | 5 | 5 | 5 |
| 59 | 5 | 5 | 5 | 5 |
| 60 | 20 | 5 | 5 | 5 |
| 61 | 5 | 5 | 5 | 5 |
| 62 | 5 | 5 | 5 | 5 |
| 63 | 5 | 5 | 5 | 5 |
| 64 | 5 | 4 | 5 | 5 |
| 65 | 5 | 5 | 4 | 5 |
| 66 | 20 | 5 | 5 | 5 |
| 67 | 5 | 5 | 5 | 5 |
| 68 | 5 | 4 | 5 | 5 |
| 69 | 20 | 5 | 5 | 5 |
| 70 | 20 | 5 | 5 | 5 |
| 71 | 5 | 5 | 5 | 5 |
| 72 | 20 | — | 5 | 5 |
| 73 | 5 | 5 | 5 | 5 |
| 74 | 20 | 4 | — | 5 |
| 75 | 5 | 4 | 5 | 5 |
| 76 | 20 | 5 | 5 | 5 |
| 77 | 20 | 5 | 5 | 5 |

Test Example 3

Cylindrical plastic pots (diameter, 8 cm; height, 12 cm) were filled with paddy field soil, and the seeds of barnyardgrass (*Echinochloa oryzicola*) were sowed in 1 to 2 cm depth. Water was poured therein to make a flooded condition, and rice seedlings of 2-leaf stage were transplanted therein, and the test plants were grown in a greenhouse. Six days (at that time weeds began to germinate) thereafter, a designated amount of the test compound formulated in an emulsifiable concentrate as in Formulation Example 2 was diluted with water (5 ml), and the dilution was applied to the water surface. The test plants were grown for an additional 20 days in the greenhouse, and the herbicidal activity and phytotoxicity were examined. The results are shown in Table 5.

TABLE 5

| Compound No. | Dosage (g/are) | Phytotoxicity Rice plant | Herbicidal activity Barnyard grass |
|---|---|---|---|
| 2 | 10 | 0 | 4 |
| 5 | 2.5 | 1 | 5 |
| 9 | 2.5 | 0 | 4 |
| 11 | 2.5 | 1 | 5 |
| 23 | 2.5 | 1 | 5 |
| 29 | 10 | 1 | 5 |
| | 2.5 | 1 | 5 |
| 50 | 2.5 | 0 | 5 |
| 52 | 2.5 | 1 | 5 |
| 64 | 10 | 1 | 5 |
| | 2.5 | 0 | 5 |
| 66 | 10 | 0 | 5 |
| | 2.5 | 0 | 5 |
| 67 | 2.5 | 1 | 5 |
| 70 | 2.5 | 0 | 5 |
| 71 | 2.5 | 0 | 5 |
| 77 | 10 | 0 | 5 |

Test Example 4

Vats (33 cm × 23 cm × 11 cm) were filled with upland field soil, and the seeds of soybean, corn, tall morningglory, velvetleaf and Johnsongrass were sowed therein and cultivated for 16 days in a greenhouse. A designated amount of the test compound formulated in an emulsifiable concentrate as in Formulation Example 2 was diluted with water, and the dilution was sprayed over the foliage of the test plants by means of a small sprayer at a spray volume of 10 liters per are. The test plants were further grown in the greehouse for 18 days, and the herbicidal activity and phytotoxicity were examined. At the time of the application, the test plants generally at the 1 to 4 leaf stage and in 2 to 12 cm height, although the growing stage of the test plants varied depending on their species. The results are shown in Table 6.

TABLE 6

| Compound No. | Dosage (g/are) | Phytotoxicity | | Herbicidal activity | | |
|---|---|---|---|---|---|---|
| | | Soybean | Corn | Tall morning-glory | Velvet-leaf | Johnson-grass |
| 2 | 1.25 | 1 | — | 5 | 4 | 4 |
| 9 | 0.16 | 1 | 1 | 5 | 5 | — |
| 14 | 0.16 | — | 1 | 5 | 4 | 4 |
| 16 | 0.16 | — | 1 | 5 | 5 | — |
| 17 | 0.63 | — | 1 | 4 | 5 | — |
| 18 | 0.04 | 1 | 1 | 5 | 5 | — |
| 20 | 0.04 | 1 | 1 | 4 | 5 | — |
| 24 | 0.63 | 1 | 1 | 4 | 4 | — |
| 28 | 0.08 | — | 1 | 5 | 4 | — |
| 33 | 0.02 | 1 | 1 | 5 | 4 | — |
| 38 | 0.08 | — | 1 | 5 | 5 | 5 |
| 44 | 0.16 | 1 | 1 | 4 | 5 | 4 |
| 37 | 0.08 | — | 1 | 5 | 5 | — |
| 77 | 2.5 | — | 1 | 5 | 5 | 4 |

Test Example 5

Vats (33 cm × 23 cm × 11 cm) were filled upland field soil, and the seeds of tall morningglory, velvetleaf, black nightshade, barnyardgrass and Johnsongrass were sowed therein and cultivated in a greenhouse for 16 days. A designated amount of the test compound formulated in an emulsifiable concentrate as in Formulation Example 2 was diluted with water, and the dilution was sprayed over the foliage of the test plants by means of a small sprayer at a spray volume of 10 liters per are. The test plants were further grown in the greenhouse for 18 days, and the herbicidal activity was examined. At the time of the application, the test plants were generally at the 1 to 4 leaf stage and in 2 to 12 cm height, although the growing stage of the test plants varied depending on their weed species. The results are shown in Table 7.

TABLE 7

| Compound No. | Dosage (g/are) | Herbicidal activity | | | | |
|---|---|---|---|---|---|---|
| | | Tall morning-glory | Velvet-leaf | Black-night-shade | Barn-yard grass | Johnson-grass |
| 10 | 0.32 | 5 | 5 | 5 | 5 | — |
| 13 | 0.16 | 5 | 5 | 5 | 5 | 5 |
| 14 | 0.16 | 5 | 4 | 4 | — | 4 |
| 15 | 0.16 | 5 | 5 | 5 | 5 | — |
| 16 | 0.16 | 5 | 5 | 5 | 4 | — |
| 21 | 0.16 | 5 | 5 | 5 | 4 | 4 |
| 23 | 0.63 | 5 | 5 | 5 | 4 | 5 |
| 29 | 0.32 | 5 | 4 | 5 | — | — |
| 34 | 0.32 | 5 | 5 | 5 | 5 | 4 |
| 35 | 0.32 | 5 | 5 | 5 | 5 | 5 |
| 43 | 0.63 | 5 | 5 | 5 | 5 | 5 |
| 57 | 0.32 | 5 | 5 | 5 | — | — |
| 73 | 0.63 | 5 | 5 | 5 | 5 | 5 |

What is claimed is:

1. A compound of the formula:

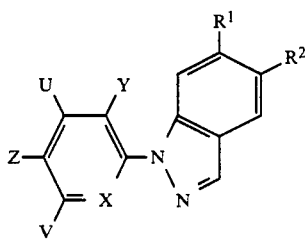

wherein X is CH, CCl or CF; Y is hydrogen or halogen; Z is $C_1$-$C_2$ perfluoroalkyl; U and V are the same or different and each is hydrogen, halogen or $C_1$-$C_2$ alkyl optionally substituted with halogen; $R^1$ is hydrogen, halogen, nitro, cyano, $C_1$-$C_5$ hydroxyalkyl, —$QB^1$ [wherein Q is oxygen or sulfur, and $B^1$ is hydrogen, $C_1$-$C_5$ alkyl, $C_2$-$C_4$ alkenyl, $C_3$-$C_5$ alkynyl, $C_3$-$C_6$ cycloalkyl, cyanomethyl, $C_1$-$C_4$ haloalkyl, $C_1$-$C_4$ alkylcarbonyl, $C_1$-$C_4$ alkoxycarbonyl, $C_1$-$C_4$ hydroxyalkyl, $C_1$-$C_3$ alkoxy($C_1$-$C_2$)alkyl or —$CHB^{21}CO_2B^{22}$ (wherein $B^{21}$ is hydrogen, halogen, $C_1$-$C_3$ alkyl or methoxy and $B^{22}$ is hydrogen, $C_1$-$C_5$ alkyl, $C_2$-$C_4$ alkenyl, $C_3$-$C_5$ alkynyl, $C_3$-$C_6$ cycloalkyl, $C_1$-$C_3$ haloalkyl or $C_1$-$C_3$ alkoxy($C_1$-$C_2$)alkyl)], —$CO_2B^{22}$ wherein $B^{22}$ is as defined above], —$ND^1D^2$ [wherein $D^1$ and $D^2$ are the same or different and each is hydrogen, $C_1$-$C_5$ alkyl, $C_2$-$C_4$ alkenyl, $C_3$-$C_5$ alkynyl, $C_3$-$C_6$ cycloalkyl, cyanomethyl, $C_1$-$C_4$ haloalkyl, $C_1$-$C_4$ hydroxyalkyl, $C_1$-$C_3$ alkoxy($C_1$-$C_2$)alkyl, —$(CH_2)_nCHB^{21}CO_2B^{22}$ (wherein n is an integer of 0, 1 or 2, and $B^{21}$ and $B^{22}$ are each as defined above) or —$SO_2B^{23}$ (wherein $B^{23}$ is $C_1$-$C_5$ alkyl optionally substituted with halogen)] or —$COD^{21}$ [wherein $D^{21}$ is hydorgen, $C_1$-$C_4$ alkyl, $C_1$-$C_3$ alkoxy($C_1$-$C_2$)alkyl]; $R^2$ is hydrogen, halogen, nitro, cyano or amino; or agrochemically acceptable salts thereof.

2. A compound according to claim 1, wherein $R^1$ is —$OB^1$.

3. A compound according to claim 1, wherein $R^1$ is —$OB^1$ (wherein $B^1$ is $C_1$-$C_5$ alkyl, $C_2$-$C_4$ alkenyl, $C_3$-$C_5$ alkynyl or —$CHB^{21}CO_2B^{22}$).

4. A compound according to claim 1, wherein $R^1$ is —$OCHB^{21}CO_2B^{22}$.

5. A compound according to claim 1, wherein $R^1$ is —$OCH(CH_3)CO_2B^{22}$.

6. A compound according to claim 1, wherein $R^1$ is —$OCH(CH_3)CO_2B^{22}$ (wherein $B^{22}$ is $C_1$-$C_5$ alkyl).

7. A compound according to claim 1, wherein $R^1$ is —$OB^1$ (wherein $B^1$ is $C_1$-$C_5$ alkyl, $C_2$-$C_4$ alkenyl or $C_3$-$C_5$ alkynyl).

8. A compound according to claim 1, wherein $R^1$ is —$OB^1$ and $R^2$ is hydrogen or nitro.

9. A compound according to claim 1, wherein $R^1$ is —$OB^1$ (wherein $B^1$ is $C_1$-$C_5$ alkyl, $C_2$-$C_4$ alkenyl, $C_3$-$C_5$ alkynyl or —$CHB^{21}CO_2B^{22}$) and $R^2$ is hydrogen or nitro.

10. A compound according to claim 1, wherein $R^1$ is —$OCHB^{21}CO_2B^{22}$ and $R^2$ is hydrogen or nitro.

11. A compound according to claim 1, wherein $R^1$ is —$OCH(CH_3)CO_2B^{22}$ and $R^2$ is hydrogen or nitro.

12. A compound according to claim 1, wherein $R^1$ is —$OCH(CH_3)CO_2B^{22}$ (wherein $B^{22}$ is $C_1$-$C_5$ alkyl) and $R^2$ is hydrogen or nitro.

13. A compound according to claim 1, wherein $R^1$ is —$OB^1$ (wherein $B^1$ is $C_1$-$C_5$ alkyl, $C_2$-$C_4$ alkenyl or $C_3$-$C_5$ alkynyl) and $R^2$ is nitro.

14. A compound according to claim 1, wherein $R^1$ is —$OCH(CH_3)CO_2B^{22}$ and $R^2$ is hydrogen.

15. A compound according to claim 1, wherein $R^1$ is —$OB^1$; X is CCl or CF; Y is chlorine or fluorine; Z is trifluoromethyl; U is hydrogen; and V is hydrogen.

16. A compound according to claim 1, wherein $R^1$ is —$OB^1$ (wherein $B^1$ is $C_1$-$C_5$ alkyl, $C_2$-$C_4$ alkenyl, $C_3$-$C_5$ alkynyl or —$CHB^{21}CO_2B^{22}$); X is CCl or CF; Y is chlorine or fluorine; Z is trifluoromethyl; U is hydrogen; and V is hydrogen.

17. A compound according to claim 1, wherein $R^1$ is —$OCHB^{21}CO_2B^{22}$; X is CCl or CF; Y is chlorine or fluorine; Z is trifluoromethyl; U is hydrogen; and V is hydrogen.

18. A compound according to claim 1, wherein $R^1$ is —$OCH(CH_3)CO_2B^{22}$; X is CCl or CF; Y is chlorine or fluorine; Z is trifluoromethyl; U is hydrogen; and V is hydrogen.

19. A compound according to claim 1, wherein $R^1$ is —$OCH(CH_3)CO_2B^{22}$ (wherein $B^{22}$ is $C_1$-$C_5$ alkyl); X is CCl or CF; Y is chlorine or fluorine; Z is trifluoromethyl; U is hydrogen; and V is hydrogen.

20. A compound according to claim 1, wherein $R^1$ is —$OB^1$ (wherein $B^1$ is $C_1$-$C_5$ alkyl, $C_2$-$C_4$ alkenyl or $C_3$-$C_5$ alkynyl); X is CCl or CF; Y is chlorine or fluorine; Z is trifluoromethyl; U is hydrogen; and V is hydrogen.

21. A compound according to claim 1, wherein $R^1$ is —$OB^1$; $R^2$ is hydrogen or nitro; X is CCl or CF; Y is chlorine or fluorine; Z is trifluoromethyl; U is hydrogen; and V is hydrogen.

22. A compound according to claim 1, wherein $R^1$ is —$OB^1$ (wherein $B^1$ is $C_1$-$C_5$ alkyl, $C_2$-$C_4$ alkenyl, $C_3$-$C_5$ alkynyl or —$CHB^{21}CO_2B^{22}$); $R^2$ is hydrogen or nitro; X is CCl or CF; Y is chlorine or fluorine; Z is trifluoromethyl; U is hydrogen; and V is hydrogen.

23. A compound according to claim 1, wherein $R^1$ is —$OCHB^{21}CO_2B^{22}$; $R^2$ is hydrogen or nitro; X is CCl or CF; Y is chlorine or fluorine; Z is trifluoromethyl; U is hydrogen; and V is hydrogen.

24. A compound according to claim 1, wherein $R^1$ is —$OCH(CH_3)CO_2B^{22}$; $R^2$ is hydrogen or nitro; X is CCl or CF; Y is chlorine or fluorine; Z is trifluoromethyl; U is hydrogen; and V is hydrogen.

25. A compound according to claim 1, wherein $R^1$ is $-OCH(CH_3)CO_2B^{22}$ (wherein $B^{22}$ is $C_1$-$C_5$ alkyl); $R^2$ is hydrogen or nitro; X is CCl or CF; Y is chlorine or fluorine; Z is trifluoromethyl; U is hydrogen; and V is hydrogen.

26. A compound according to claim 1, wherein $R^1$ is $-OB^1$ (wherein $B^{22}$ is $C_1$-$C_5$ alkyl, $C_2$-$C_4$ alkenyl or $C_3$-$C_5$ alkynyl); $R^2$ is nitro; X is CCl or CF; Y is chlorine or fluorine; Z is trifluoromethyl; U is hydrogen; and V is hydrogen.

27. A compound according to claim 1, wherein $R^1$ is $-OCH(CH_3)CO_2B^{22}$; $R^2$ is hydrogen; X is CCl or CF; Y is chlorine or fluorine; Z is trifluoromethyl; U is hydrogen; and V is hydrogen.

28. A compound according to claim 1, wherein X is CCl; Y is chlorine; Z is trifluoromethyl; U, V and $R^2$ are hydrogen; and $R^1$ is

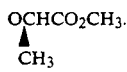

29. A compound according to claim 1, wherein X is CCl; Y is chlorine; Z is trifluoromethyl; U, V and $R^2$ are hydrogen; and $R^1$ is $OCH(CH_3)CO_2C_3H_7$—(i).

30. A compound according to claim 1, wherein X is CCl; Y is chlorine; Z is trifluoromethyl; U, V and $R^2$ are hydrogen; and $R^1$ is $OCH(CH_3)CO_2C_2H_5$.

31. A compound according to claim 1, wherein X is CH; Y is chlorine; Z is trifluoromethyl; U, V and $R^2$ are hydrogen; and $R^1$ is $OCH(CH_3)CO_2C_2H_5$.

32. A compound according to claim 1, wherein X is CCl; Y is chlorine; Z is trifluoromethyl; U and V are hydrogen; $R^1$ is $OCH(CH_3)CO_2CH_3$; and $R^2$ is nitro.

33. A compound according to claim 1, wherein X is CCl; Y is chlorine; Z is trifluoromethyl; U and V are hydrogen; $R^1$ is $OCH(CH_3)CO_2C_3H_7$—(i); and $R^2$ is nitro.

34. A compound according to claim 1, wherein X is CCl; Y is chlorine; Z is trifluoromethyl; U and V are hydrogen; $R^1$ is $OCH(CH_3)CO_2C_5H_{11}$—(n); and $R^2$ is nitro.

35. A herbicidal composition comprising as an active ingredient a herbicidally effective amount of the compound according to claim 1.

36. A method for exterminating undesired weeds, which comprises applying a herbicidally effective amount of the compound according to claim 1 to an area where the undesired weeds grow or will grow.

* * * * *